(12) United States Patent
Jeong et al.

(10) Patent No.: US 10,069,083 B2
(45) Date of Patent: Sep. 4, 2018

(54) CONDENSED CYCLIC COMPOUNDS AND ORGANIC LIGHT-EMITTING DEVICES INCLUDING THE SAME

(71) Applicant: SAMSUNG DISPLAY CO., LTD., Yongin, Gyeonggi-Do (KR)

(72) Inventors: Eun-Jae Jeong, Yongin (KR);
Young-Kook Kim, Yongin (KR);
Jun-Ha Park, Yongin (KR);
Eun-Young Lee, Yongin (KR);
Seok-Hwan Hwang, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 451 days.

(21) Appl. No.: 14/507,354

(22) Filed: Oct. 6, 2014

(65) Prior Publication Data

US 2015/0349275 A1 Dec. 3, 2015

(30) Foreign Application Priority Data

Jun. 2, 2014 (KR) ........................ 10-2014-0067062

(51) Int. Cl.
*H01L 51/00* (2006.01)
*C07D 401/04* (2006.01)
(Continued)

(52) U.S. Cl.
CPC ........ *H01L 51/0072* (2013.01); *C07D 401/04* (2013.01); *C07D 401/10* (2013.01); *H01L 51/0067* (2013.01); *H01L 51/5084* (2013.01)

(58) Field of Classification Search
None
See application file for complete search history.

(56) References Cited

U.S. PATENT DOCUMENTS 5,645,948 A 7/1997 Shi et al.
6,465,115 B2 10/2002 Shi et al.
(Continued)

FOREIGN PATENT DOCUMENTS

JP 10-17860 A 1/1998
JP 11-87067 A 3/1999
(Continued)

OTHER PUBLICATIONS

Tobisu et al. (Angew. Chem. Int. Ed. 2012, 51, p. 11363). Nov. 29, 2016.*
(Continued)

*Primary Examiner* — J. L. Yang
(74) *Attorney, Agent, or Firm* — Lee & Morse, P.C.

(57) ABSTRACT

A condensed cyclic compound and an organic light-emitting device including the same, the condensed cyclic compound being represented by Formula 1 below:
(Continued)

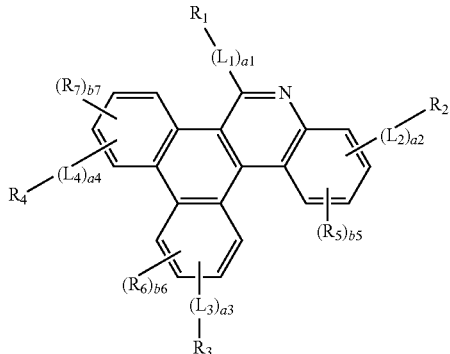

<Formula 1>

22 Claims, 1 Drawing Sheet

(51) Int. Cl.
  *C07D 401/10* (2006.01)
  *H01L 51/50* (2006.01)

(56) References Cited

U.S. PATENT DOCUMENTS

| 6,596,415 | B2 | 7/2003 | Shi et al. |
|---|---|---|---|
| 2003/0165715 | A1 | 9/2003 | Yoon et al. |
| 2012/0132899 | A1 | 5/2012 | Kawamura et al. |
| 2013/0001522 | A1 | 1/2013 | Lee et al. |
| 2013/0001527 | A1 | 1/2013 | Han et al. |
| 2013/0001529 | A1 | 1/2013 | Lim et al. |
| 2016/0204357 | A1* | 7/2016 | Jang .................... C07D 401/14 257/40 |

FOREIGN PATENT DOCUMENTS

| JP | 2012-28711 A | 2/2012 |
|---|---|---|
| KR | 10-0691543 B1 | 3/2007 |
| KR | 10-2012-0115083 A | 10/2012 |
| KR | 10-2013-0007047 A | 1/2013 |
| KR | 10-2013-0007160 A | 1/2013 |
| KR | 10-2013-0007162 A | 1/2013 |
| KR | 10-2013-0094628 A | 8/2013 |
| KR | 10-2014-0021294 A | 2/2014 |
| WO | WO-2015/199512 A1 * | 12/2015 |

OTHER PUBLICATIONS

Glinka (Roczn. Chem. 1977, 51(3), p. 577) abstract. Nov. 29, 2016.*
Zhang et al. (Org. Lett. 2014, 16, p. 250).*
Glinka (Pol. J. Chem. 1978, 52, p. 1039). Nov. 17, 2017.*
Fernando Portela-Cubillo, et al., Microwave-Assisted Syntheses of N-Heterocycles Using Alkenone-,Alkynone- and Aryl-carbonyl 0-Phenyl Oximes: Formal Synthesis of Neocryptolepine, J. Org. Chem. 2008, 73, 5558-5565.
C.W. Tang, et al., "Organic electroluminescent diodes", Appl. Phys. Lett., 51, No. 12, 913-915 (1987).
Chihaya Adachi, et al., "Confinement of charge carriers and molecular excitons within 5nmthick emitter layer in organic electroluminescent devices with a double heterostructure", Appl. Phys. Lett., 57, No. 6, 531-533, (1990).
Youichi Sakamoto, et al., "Synthesis, Characterization, and Electron-Transport Property of Perfluorinated Phenylene Dendrimers", J. Am. Chem. Soc., 2000, 122 (8), pp. 1832-1833.
Shigehiro Yamaguchi, et al., "Diphenylamino-Substituted 2,5-Diarylsiloles for Single-Layer Organic Electroluminescent Devices", Chemistry Letters (2001), p. 98-99.
Nicholas Johansson, et al., "Solid-State Amplified Spontaneous Emission in Some Spiro-Type Molecules: A New Concept for the Design of Solid-State Lasing Molecules", Adv. Mater. 10 (1998) 1136-1141.
Y.T. Tao, et al., "Sharp green electroluminescence from 1H-pyrazolo[3,4-b]quinoline-based light-emitting diodes", Appl. Phys. Lett. 77 (2000) 1575-1577.
CAS Registry No. _73013-73-7P.
Korean Office action dated May 1, 2017 in the examination of the corresponding Korean Patent Application No. 10-2014-0067062.
Yan, et al., "Palladium-catalyzed tandem N—H/C—H arylation: regioselective synthesis of N-heterocycle-fused phenanthridines as versatile blue-emitting luminophores," Org. Biomol. Chem., 2013, 11, 7966-7977.
Sun, et al. "Visible-Light-Mediated Fluoroalkylation of Isocyanides with Ethyl Bromofluoroacetates: Unified Synthesis of Mono- and Difluoromethylated Phenanthridine Derivatives," Org. Lett. 2014, 16, 2938-2941.
Korean Notice of Allowance dated Sep. 20, 2017 for corresponding Korean Patent Application No. 10-2014-0067062.

* cited by examiner

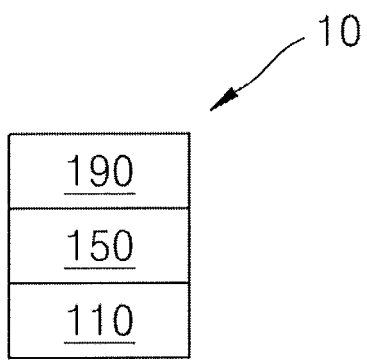

CONDENSED CYCLIC COMPOUNDS AND ORGANIC LIGHT-EMITTING DEVICES INCLUDING THE SAME

CROSS-REFERENCE TO RELATED APPLICATION

Korean Patent Application No. 10-2014-0067062, filed on Jun. 2, 2014, in the Korean Intellectual Property Office, and entitled: "Condensed Cyclic Compounds and Organic Light-Emitting Devices Including the Same," is incorporated by reference herein in its entirety.

BACKGROUND

1. Field

Embodiments relate to condensed cyclic compounds and organic light-emitting devices including the same.

2. Description of the Related Art

Organic light-emitting devices (OLEDs) are self-emitting devices that can provide multicolored images and may have advantages such as wide viewing angle, excellent contrast, quick response time, excellent brightness, low driving voltage, and excellent response speed characteristics.

An OLED may have a structure including a first electrode disposed on a substrate, and a hole transport region, an emission layer (EML), an electron transport region, and a second electrode sequentially formed on the first electrode. Holes injected from the first electrode move to the EML via the hole transport region, and electrons injected from the second electrode move to the EML via the electron transport region. Excitons may be generated when carriers such as holes and electrons recombine in the EML. When the excitons drop from an excited state to a ground state, light is emitted.

SUMMARY

Embodiments are directed to condensed cyclic compounds and organic light-emitting devices including the same.

According to one or more embodiments, provided is a condensed cyclic compound represented by Formula 1 below:

<Formula 1>

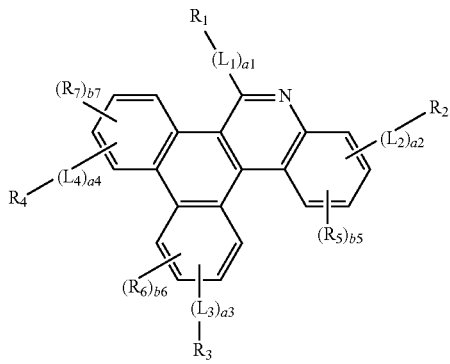

in Formula 1, $L_1$ to $L_4$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

a1 to a4 may be each independently selected from 0, 1, 2 and 3;

$R_1$ to $R_4$ may be each independently selected from hydrogen, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group (substituted or unsubstituted monovalent non-aromatic condensed polycyclic group) a substituted or unsubstituted monovalent non-aromatic condensed hetero-polycyclic group (substituted or unsubstituted monovalent non-aromatic hetero-condensed polycyclic group), —P(=O)($Q_1$)($Q_2$), and —S(=O)$_2$($Q_1$);

$R_5$ to $R_7$ may be each independently selected from hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arythio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed hetero-polycyclic group;

b2 to b4 may be each independently selected from 1, 2, 3 and 4;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arythio group, the substituted $C_2$-$C_{60}$ heteroaryl group, the substituted monovalent non-aromatic condensed polycyclic group, and the substituted monovalent non-aromatic condensed hetero-polycyclic group may be selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group and a monovalent non-aromatic condensed hetero-polycyclic group;

$C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group and a monovalent non-aromatic condensed hetero-polycyclic group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group; and —P(=O)($Q_{11}$)($Q_{12}$) and —S(=O)$_2$($Q_{11}$); wherein, $Q_1$, $Q_2$, $Q_{11}$ and $Q_{12}$ may be each independently selected from a $C_6$-$C_{60}$ aryl group, and a $C_2$-$C_{60}$ heteroaryl group.

According to another embodiment, provided is an organic light-emitting device including a first electrode; a second electrode; and an organic layer disposed between the first electrode and the second electrode, and including an emission layer, wherein the organic layer includes at least one type of condensed cyclic compound.

BRIEF DESCRIPTION OF THE DRAWING

Features will be apparent to those of skill in the art by describing in detail exemplary embodiments with reference to the attached drawings in which:

The FIGURE illustrates a schematic structure of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

The terms used in the present specification are merely used to describe exemplary embodiments, and are not intended to limit the present application. An expression used in the singular encompasses the expression of the plural, unless it has a clearly different meaning in the context.

In the present specification, it is to be understood that the terms such as "including", "having", and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

It will be understood that when a layer, region, or component is referred to as being "formed on" another layer, region, or component, it can be directly or indirectly formed on the other layer, region, or component. That is, for example, intervening layers, regions, or components may be present.

The condensed cyclic compound according to an embodiment may be represented by Formula 1 below:

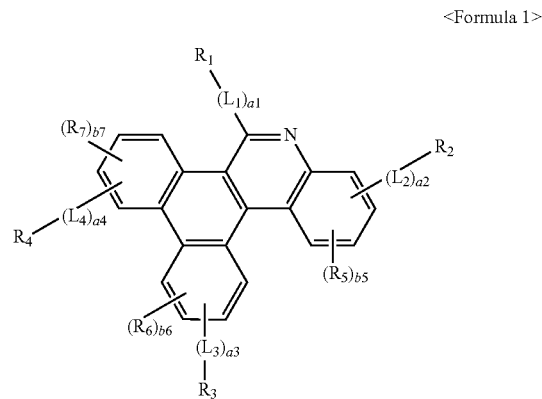

<Formula 1>

In Formula 1 above, $L_1$ to $L_4$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, and the substituted divalent non-aromatic hetero-condensed polycyclic group may be selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group; and —(=O)($Q_{11}$)($Q_{12}$) and —S(=O)$_2$($Q_{11}$); wherein, $Q_{11}$ and $Q_{12}$ may be each independently selected from a $C_6$-$C_{60}$ aryl group and a $C_2$-$C_{60}$ heteroaryl group.

For example, in Formula 1 above, $L_1$ to $L_4$ may be each independently a group selected from phenylene, pentalenylene, indenylene, naphthylene, azulenylene, heptalenylene, indacenylene, acenaphthylene, fluorenylene, spiro-fluorenylene, benzofluorenylene, dibenzofluorenylene, phenalenylene, phenanthrenylene, anthracenylene, fluoranthenylene, triphenylenylene, pyrenylene, chrysenylene, naphthacenylene, picenylene, perylenylene, pentaphenylene, hexacenylene, pentacenylene, rubicenylene, coronenylene, ovalenylene, pyrrolylene, thiophenylene, furanylene, imidazolylene, pyrazolylene, thiazolylene, isothiazolylene, oxazolylene, isooxazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzoimidazolylene, benzofuranylene, benzothiophenylene, isobenzothiazolylene, benzooxazolylene, isobenzooxazolylene, triazolylene, tetrazolylene, oxadiazolylene, triazinylene, dibenzofuranylene, dibenzothiophenylene, benzocarbazolylene, and dibenzocarbazolylene; and phenylene, pentalenylene, indenylene, naphthylene, azulenylene, heptalenylene, indacenylene, acenaphthylene, fluorenylene, spiro-fluorenylene, benzofluorenylene, dibenzofluorenylene, phenalenylene, phenanthrenylene, anthracenylene, fluoranthenylene, triphenylenylene, pyrenylene, chrysenylene, naphthacenylene, picenylene, perylenylene, pentaphenylene, hexacenylene, pentacenylene, rubicenylene, coronenylene, ovalenylene, pyrrolylene, thiophenylene, furanylene, imidazolylene, pyrazolylene, thiazolylene, isothiazolylene, oxazolylene, isooxazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzoimidazolylene, benzofuranylene, benzothiophenylene, isobenzothiazolylene, benzooxazolylene, isobenzooxazolylene, triazolylene, tetrazolylene, oxadiazolylene, triazinylene, dibenzofuranylene, dibenzothiophenylene, benzocarbazolylene, and dibenzocarbazolylene, each substituted with at least one group selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a cyclopentyl group, cyclohexyl, cycloheptyl, cyclopentenyl, cyclohexenyl, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, dibenzocarbazolyl, thiadiazolyl, and imidazopyridinyl, but they are not limited thereto.

In an implementation, in Formula 1, $L_1$ to $L_4$ may be each independently groups represented by any one of Formulae 3-1 to 3-30, but they are not limited thereto:

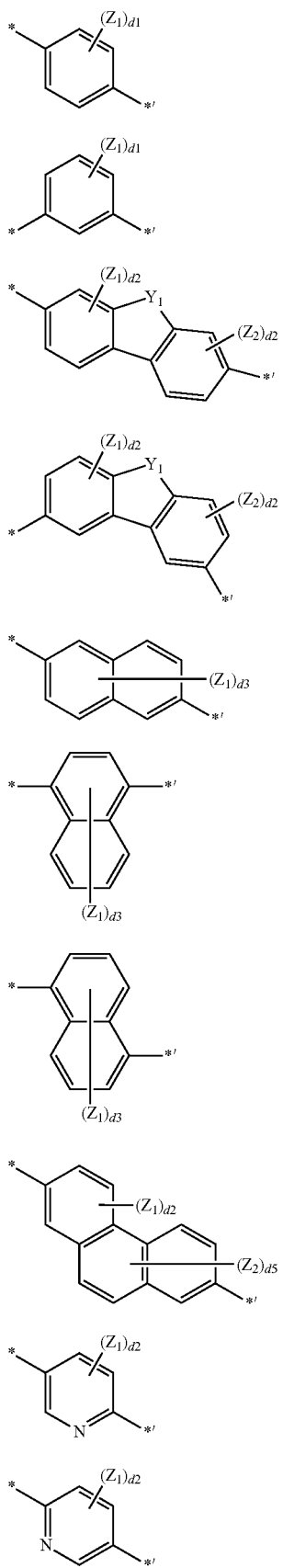

-continued 3-23
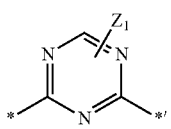

3-24
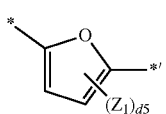

3-25
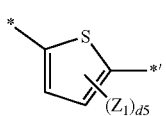

3-26
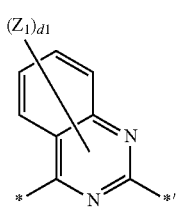

3-27
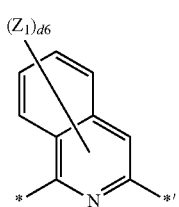

3-28
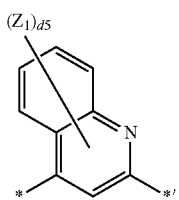

3-29
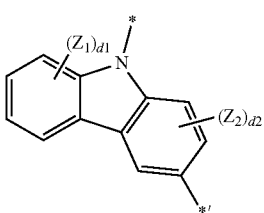

3-30
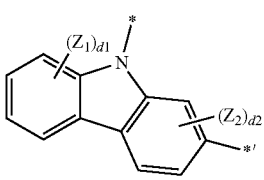

in Formulae 3-1 to 3-30, $Y_1$ may be O, S, a $C(Z_3)(Z_4)$, $N(Z_5)$, or $Si(Z_6)(Z_7)$;

$Z_1$ to $Z_7$ may be each independently selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer of 1 to 4;
d2 may be an integer of 1 to 3;
d3 may be an integer of 1 to 6;
d4 may be an integer of 1 to 8;
d5 may be 1 or 2; and
d6 may be an integer of 1 to 5. * and *' may be binding sites to neighboring atoms.

In an implementation, in Formula 1, $L_1$ to $L_4$ may be each independently groups selected from Formulae 4-1 to 4-21 below, but they are not limited thereto:

4-1
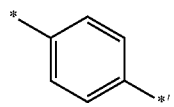

4-2
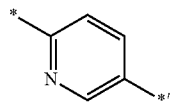

4-3
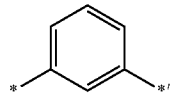

4-4
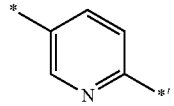

4-5
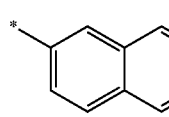

4-6
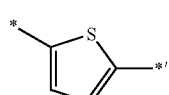

4-7
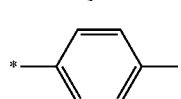

4-8
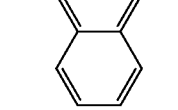

4-9
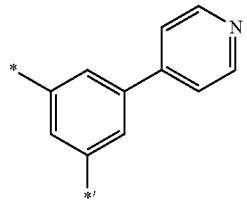

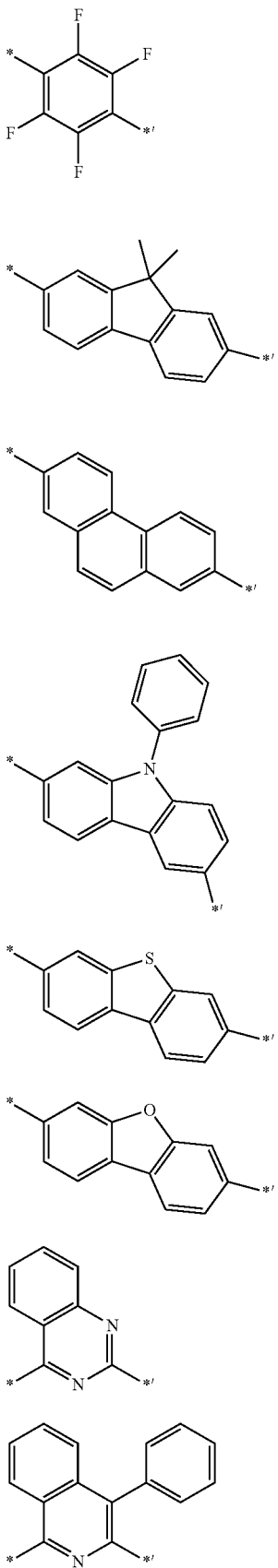
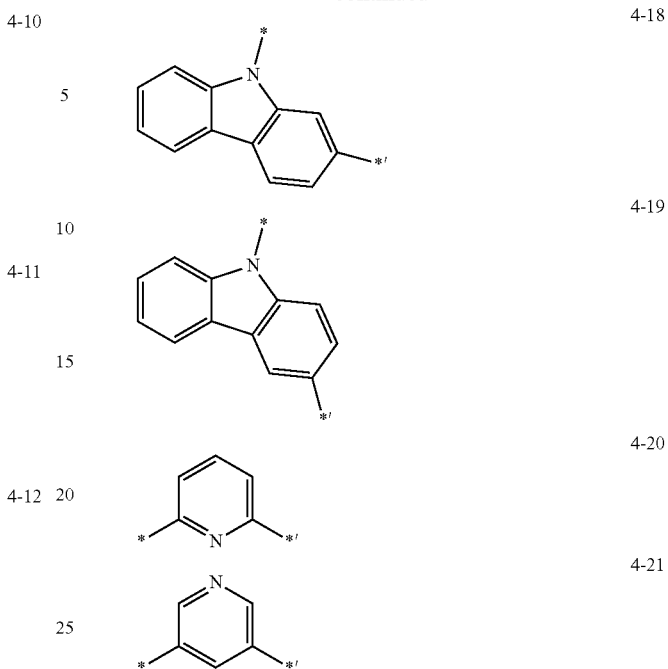

in Formulae 4-1 to 4-21, * and *' may be binding sites to neighboring atoms.

In Formula 1, a1 represents the number of $L_1$s and may be selected from 0, 1, 2, and 3. For example, in Formula 1, a1 may be selected from 0, 1, and 2, but it is not limited thereto. When a1 is an integer that is 2 or greater, a plurality of $L_1$s may be different from or the same as each other. When a1 is 0, $(L_1)_{a1}$ represents a direct bonding.

In Formula 1, a2 represents the number of $L_2$s and may be selected from 0, 1, 2, and 3. For example, in Formula 1, a2 may be selected from 0, 1, and 2, but it is not limited thereto. According to another embodiment, in Formula 1, a2 may be 0, but it is not limited thereto. When a2 is an integer that is 2 or greater, a plurality of $L_2$s may be the same as or different from each other. When a2 is 0, $(L_2)_{a2}$ represents direct bonding.

In Formula 1, a3 represents the number of $L_3$s, and may be selected from 0, 1, 2, and 3. For example, in Formula 1, a3 may be selected from 0, 1, and 2, but it is not limited thereto. According to another embodiment, in Formula 1, a3 may be 0, but it is not limited thereto. When a3 is an integer of 2 or greater, a plurality of $L_3$s may be the same as or different from each other. When a3 is 0, $(L_3)_{a3}$ represents a direct bonding.

In Formula 1, a4 represents the number of $L_4$s, and may be selected from 0, 1, 2, and 3. For example, in Formula 1, a4 may be selected from 0, 1, and 2, but it is not limited thereto. According to another embodiment, in Formula 1, a4 may be 0, but it is not limited thereto. When a4 is an integer of 2 or greater, a plurality of $L_4$s may be the same as or different from each other. When a4 is 0, $(L_4)_{a4}$ represents a direct bonding.

In Formula 1, $R_1$ to $R_4$ may be each independently selected from hydrogen, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed hetero-polycyclic group, —P(=O)($Q_1$)($Q_2$), and —S(=O)$_2$($Q_1$);

at least one substituent of the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{10}$ aryl group, the substituted $C_2$-$C_{60}$ heteroaryl group, the substituted monovalent non-aromatic condensed polycyclic group, and the substituted monovalent non-aromatic condensed hetero-polycyclic group may be selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group and a monovalent non-aromatic condensed hetero-polycyclic group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group; and —P(=O)($Q_{11}$)($Q_{12}$) and —S(=O)$_2$($Q_{11}$); wherein, $Q_1$, $Q_2$, $Q_{11}$ and $Q_{12}$ may be each independently selected from a $C_6$-$C_{60}$ aryl group, and a $C_2$-$C_{60}$ heteroaryl group.

In an implementation, in Formula 1, $R_1$ to $R_4$ may be each independently groups selected from hydrogen, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, a dibenzosilolyl group, benzocarbazolyl, dibenzocarbazolyl, and benzoxanthenyl, —P(=O)($Q_1$)($Q_2$), and —S(=O)$_2$($Q_1$); and phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, a dibenzosilolyl group, benzocarbazolyl, dibenzocarbazolyl, and benzoxanthenyl, each substituted with at least one selected from deuterium, —F, —Cl, —Br, —I, a hydroxyl group, a cyano group, a nitro group, a $C_1$-$C_{20}$ alkyl, a $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl; and $Q_1$ and $Q_2$ may be each independently selected from a $C_6$-$C_{60}$ aryl group, but they are not limited thereto.

In an implementation, in Formula 1, $R_1$ to $R_4$ may be each independently groups selected from hydrogen, phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl, benzoxanthenyl, —P(=O)($Q_1$)($Q_2$), and —S(=O)$_2$($Q_1$); and phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl and benzoxanthenyl, each substituted with at least one selected from deuterium, —F, —Cl, —Br, —I, a cyano group, a nitro group, methyl, ethyl, n-propyl, tert-butyl, methoxy, ethoxy, tert-butoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl; and $Q_1$ and $Q_2$ may be each independently selected from a phenyl group and a naphthyl group, but they are not limited thereto.

In an implementation, in Formula 1, $R_1$ to $R_4$ may be each independently selected from hydrogen, —P(=O)(Ph)$_2$ and —S(=O)$_2$(Ph) and a group represented by any one of Formulae 5-1 to 5-44, but they are not limited thereto:

5-1
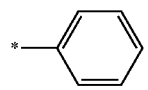

5-2
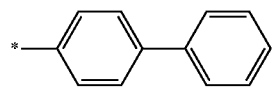

5-3
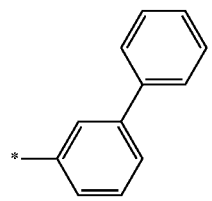

5-4
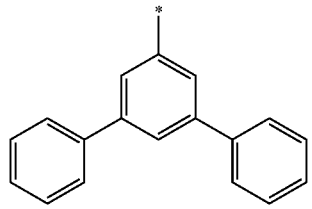

5-5
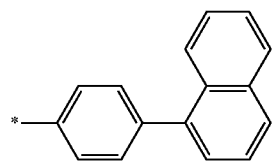

5-6
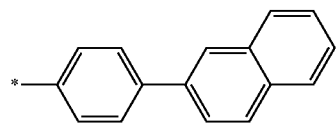

-continued 5-7
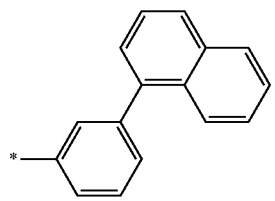

5-8
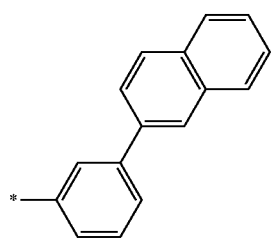

5-9
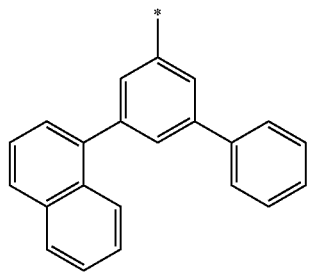

5-10
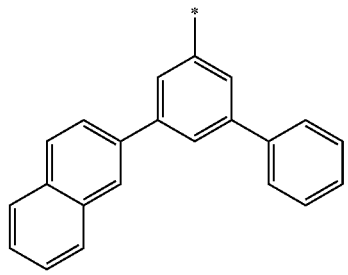

5-11
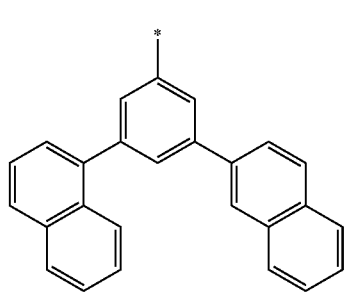

5-12
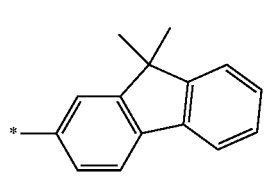

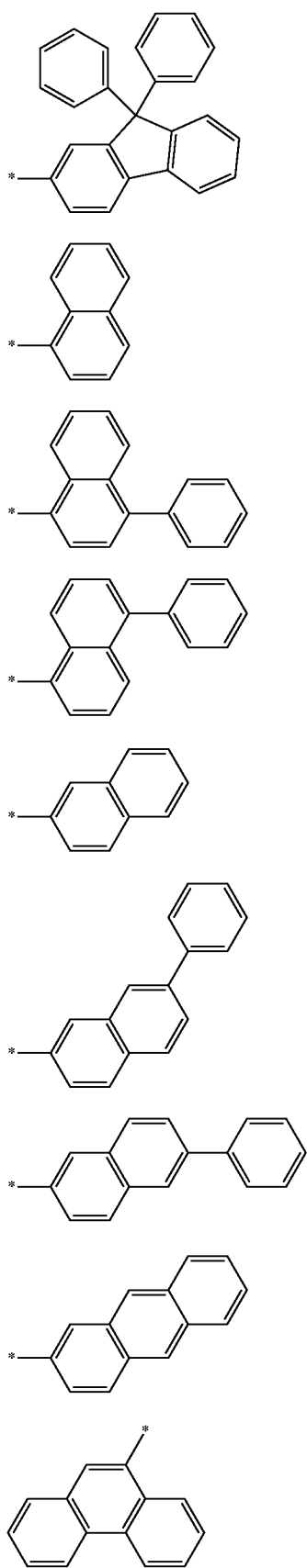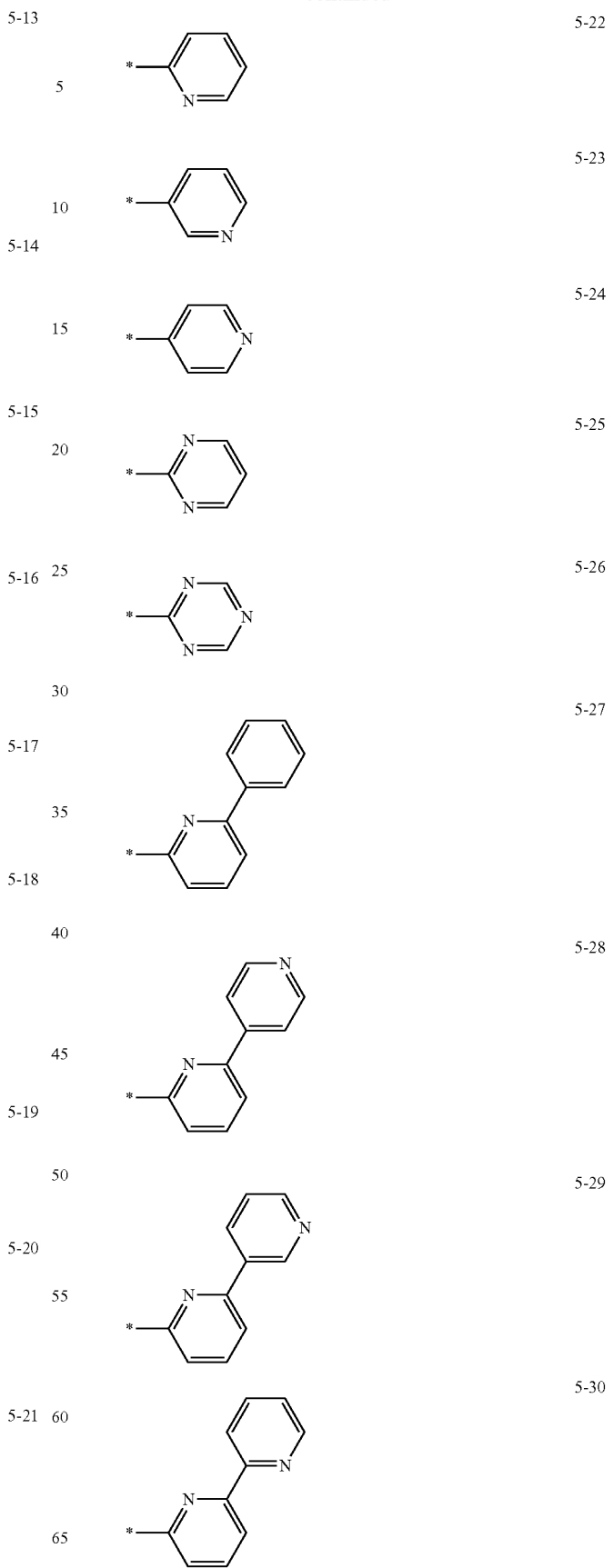

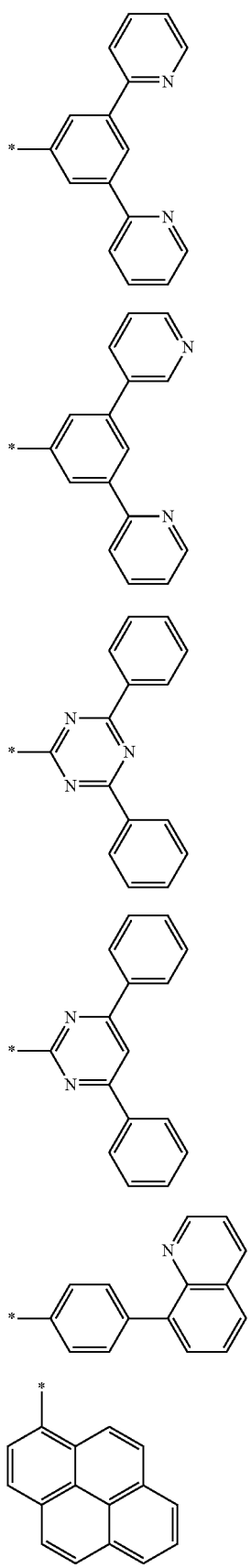
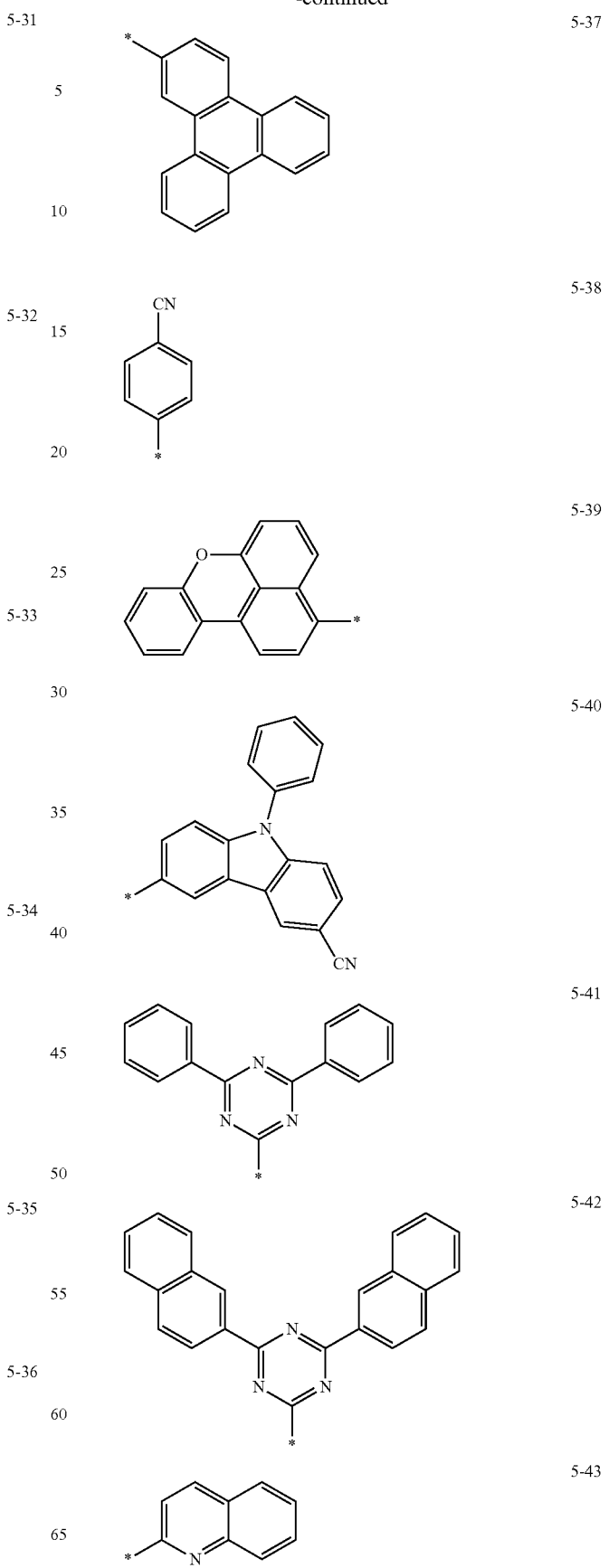

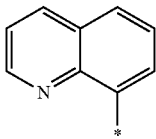

5-44 in Formulae 5-1 to 5-44, * is a binding site to neighboring atoms.

In Formula 1, $R_5$ to $R_7$ may be each independently selected from hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arythio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed hetero-polycyclic group;

at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arythio group, the substituted $C_2$-$C_{60}$ heteroaryl group, the substituted monovalent non-aromatic condensed polycyclic group, and the substituted monovalent non-aromatic condensed hetero-polycyclic group may be selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group and a monovalent non-aromatic condensed hetero-polycyclic group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group, but they are not limited thereto.

For example, in Formula 1, $R_5$ to $R_7$ may be each independently groups selected from hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl, a $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, dibenzosilolyl, benzocarbazolyl, dibenzocarbazolyl, and benzoxanthenyl; and phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl dibenzofuranyl, dibenzothiophenyl, a dibenzosilolyl group, benzocarbazolyl, dibenzocarbazolyl and benzoxanthenyl, each substituted with at least one selected from deuterium, —F, —Cl, —Br, —I, a hydroxyl group, a cyano group, a nitro group, a $C_1$-$C_{20}$ alkyl, a $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl, but they are not limited thereto.

According to another embodiment, in Formula 1, $R_5$ to $R_7$ may be each independently groups selected from hydrogen, deuterium, —F, —Cl, —Br, —I, a hydroxyl group, a cyano group, a nitro group, methyl, ethyl, n-propyl, tert-butyl, methoxy, ethoxy, phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl, and benzoxanthenyl; and phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl and benzoxanthenyl, each substituted with at least one selected from deuterium, —F, —Cl, —Br, —I, a cyano group, a nitro group, methyl, ethyl, n-propyl, tert-butyl, methoxy, ethoxy, tert-butoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl.

According to another embodiment, in Formula 1, $R_5$ to $R_7$ may be each independently selected from hydrogen, deuterium, a cyano group, a nitro group and a group represented by any one of Formulae 5-1 to 5-44 below, but they are not limited thereto:

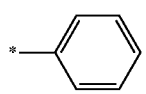
5-1

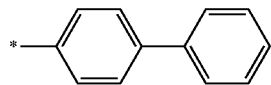
5-2

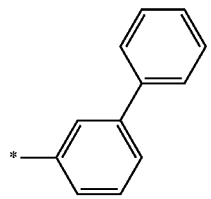
5-3

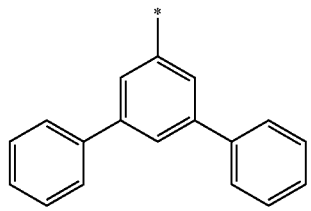
5-4

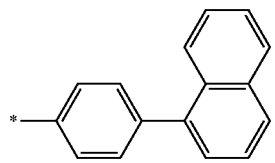
5-5

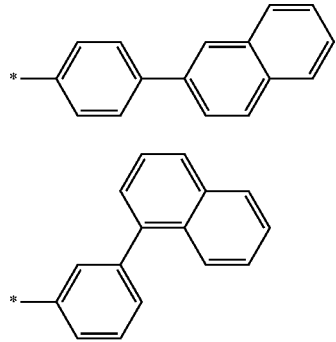
5-6

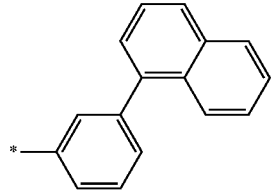
5-7

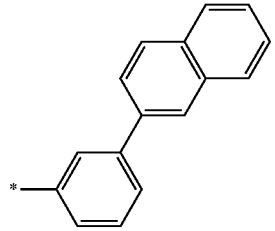
5-8

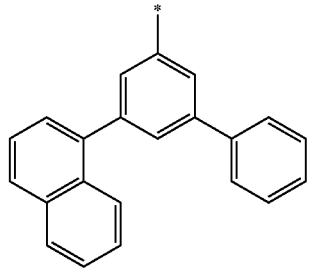
5-9

-continued
5-10 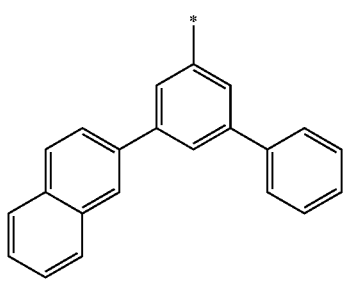
5-11 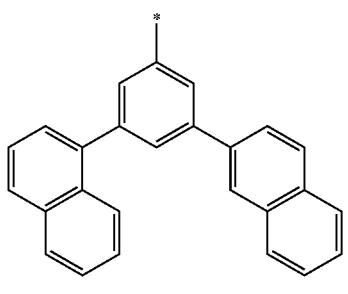
5-12 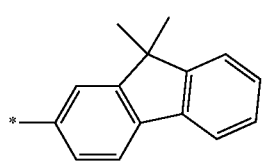
5-13 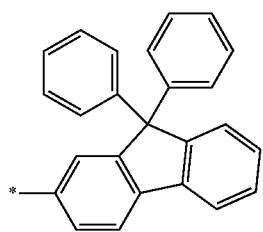
5-14 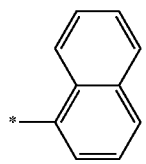
5-15 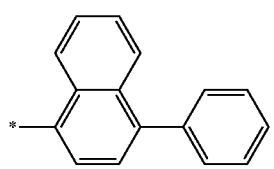
5-16 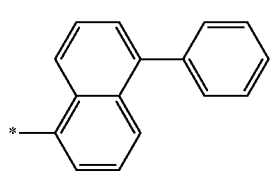
5-17 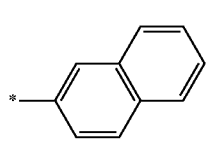
-continued
5-18 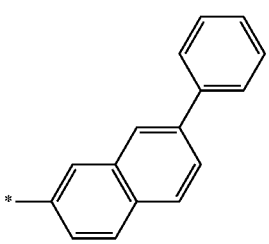
5-19 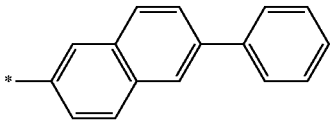
5-20 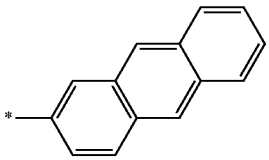
5-21 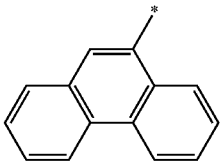
5-22 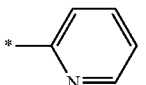
5-23 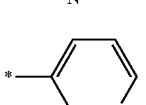
5-24 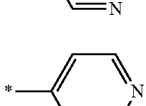
5-25 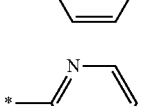
5-26 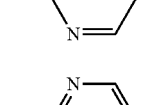
5-27 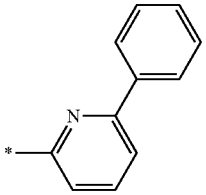

5-28 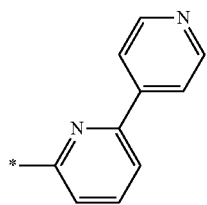
5-29 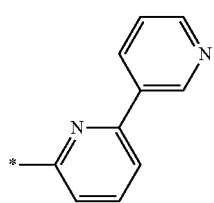
5-30 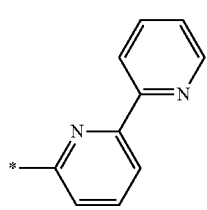
5-31 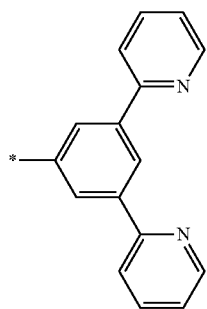
5-32 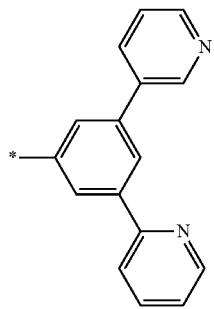
5-33 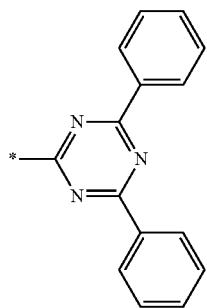
5-34 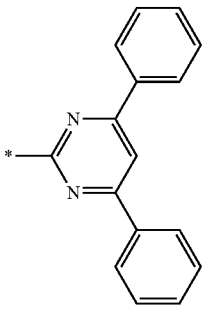
5-35 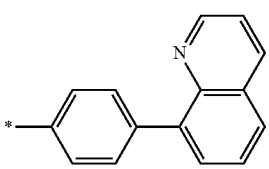
5-36 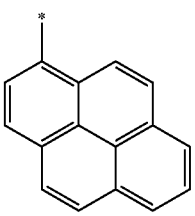
5-37 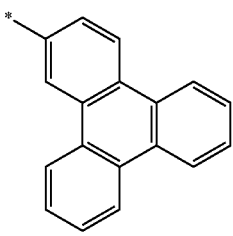
5-38 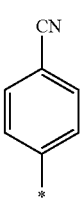
5-39 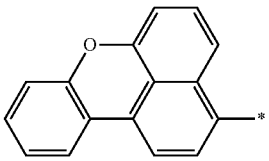
5-40 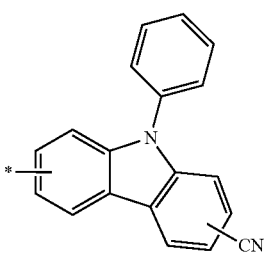

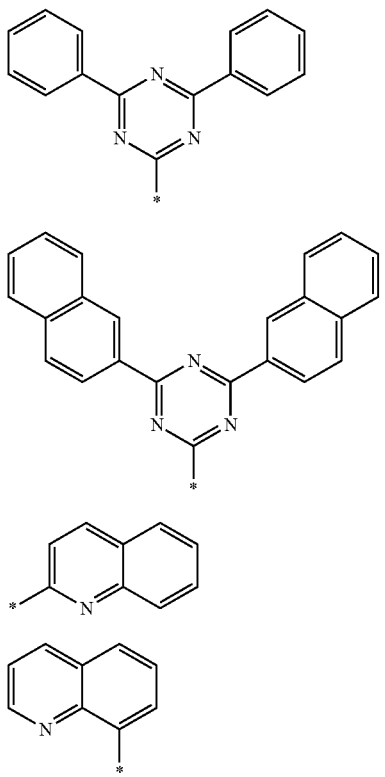

in Formulae 5-1 to 5-44, * is a binding site to neighboring atoms.

In Formula 1, b5 represents the number of $R_5$s and may be selected from 1, 2, and 3. When b5 is an integer of 2 or greater, a plurality of $R_5$s may be the same or different.

In Formula 1, b6 represents the number of $R_6$s and may be selected from 1, 2, and 3. When b6 is an integer of 2 or greater, a plurality of $R_6$s may be the same or different from each other.

In Formula 1, b7 represents the number of $R_7$s, and may be selected from 1, 2, and 3. When b7 is an integer of 2 or greater, a plurality of $R_7$s may be the same as or different from each other.

According to an embodiment, the condensed cyclic compound, e.g., represented by Formula 1, may be represented by any one of Formulae 1A to 1D, but they are not limited thereto.

<Formula 1A>

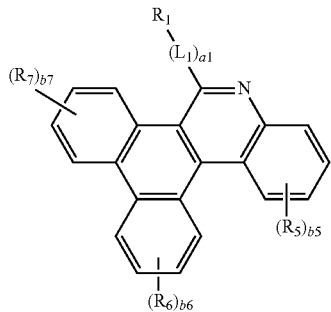

<Formula 1B>

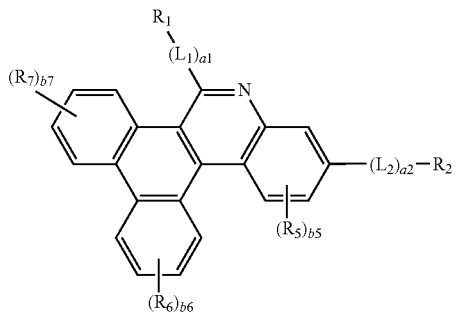

<Formula 1C>

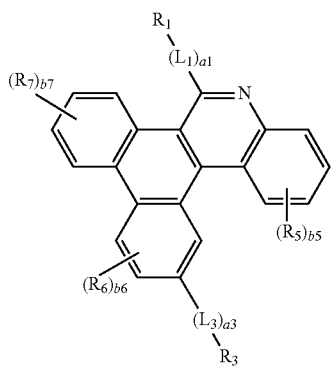

<Formula 1D>

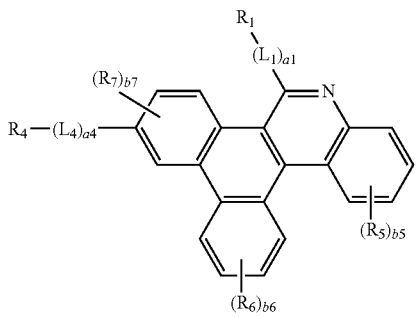

In Formulae 1A to 1D, descriptions of $L_1$ to $L_4$, a1 to a4, $R_1$ to $R_7$, and b5 to b7 may be the same as described above, e.g., as described with respect to Formula 1.

According to another embodiment, the condensed cyclic compound, e.g., represented by Formula 1, may be represented by any one of Formulae 1E to 1H, but they are not limited thereto.

<Formula 1E>

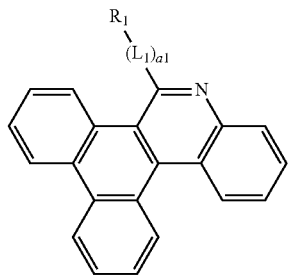

<Formula 1F>

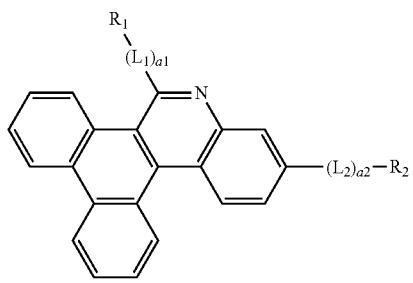

<Formula 1G>

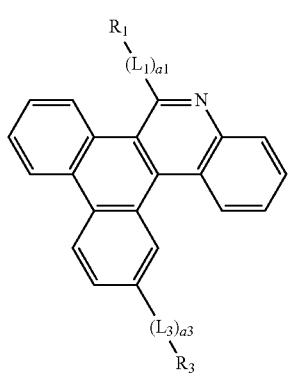

<Formula 1H>

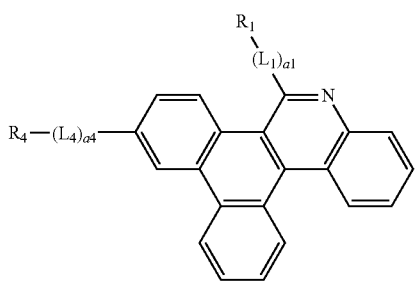

in Formulae 1E to 1H, descriptions of $L_1$ to $L_4$, a1 to a4 and $R_1$ to $R_4$ may be the same as described above, e.g., with respect to Formula 1.

When the condensed cyclic compound is represented by any one of Formulae 1E to 1H, $L_1$ to $L_4$ may be each independently selected from groups represented by Formulae 4-1 to 4-21, and a1 may be selected from 0, 1, and 2, but they are not limited thereto.

When the condensed cyclic compound is represented by any one of Formulae 1E to 1H, $R_1$ to $R_4$ may be each independently selected from hydrogen and any one of groups represented by Formulae 5-1 to 5-44, but they are not limited thereto.

According to another embodiment, the condensed cyclic compound, e.g., represented by Formula 1, may be selected from Compounds 1 to 82 below, but they are not limited thereto.

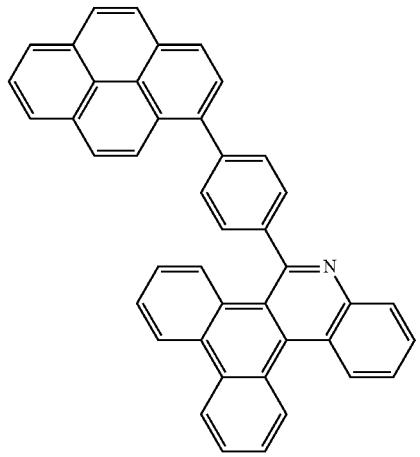

1

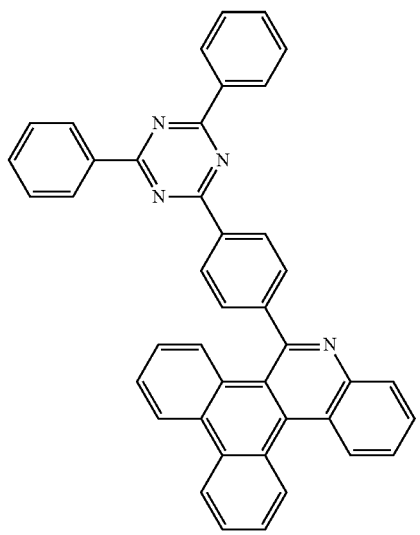

2

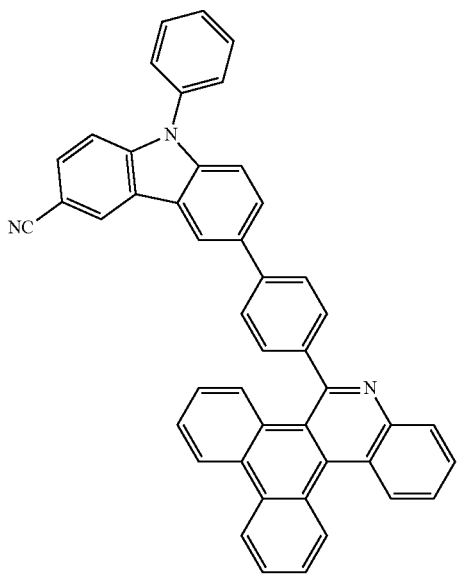

3

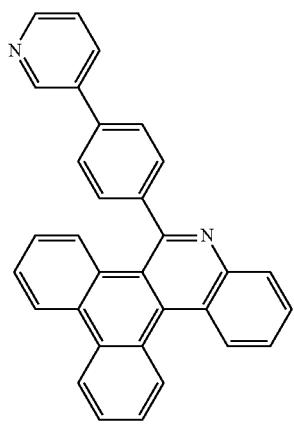
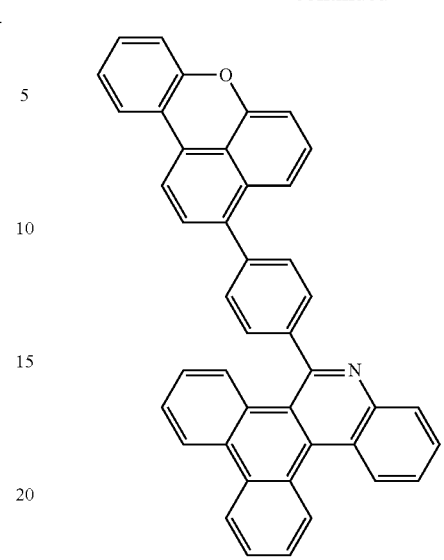
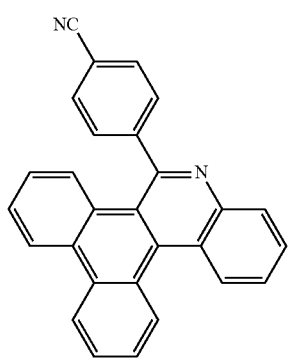
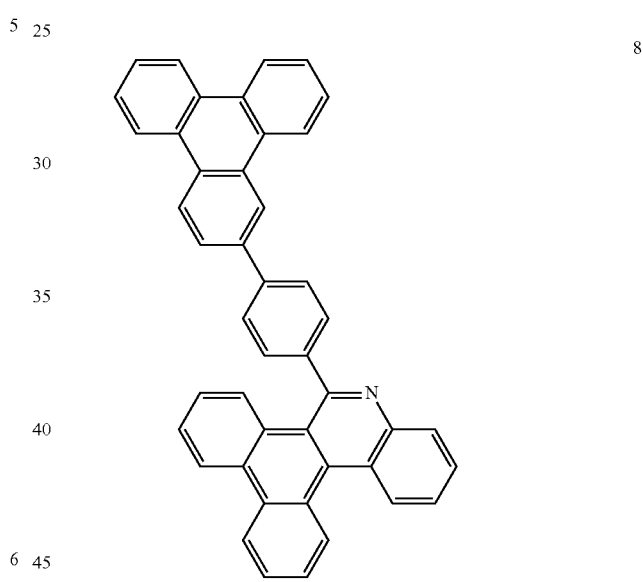
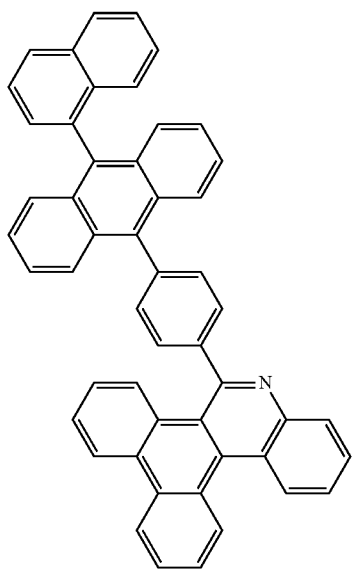
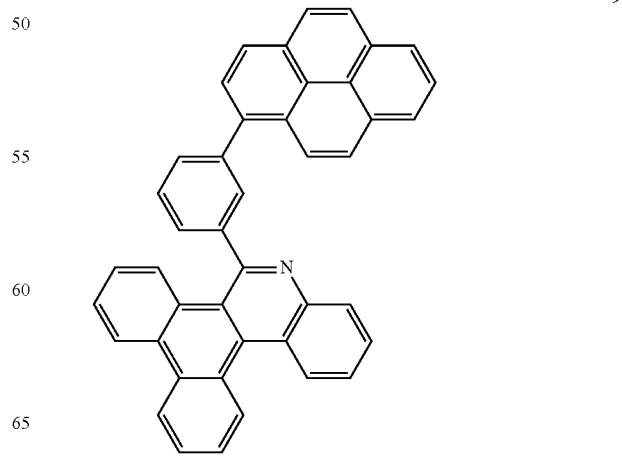

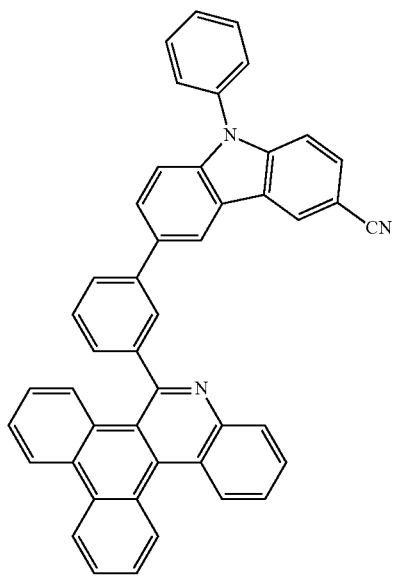
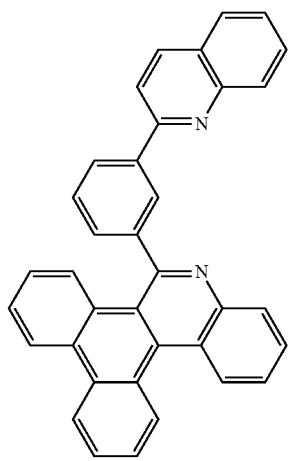
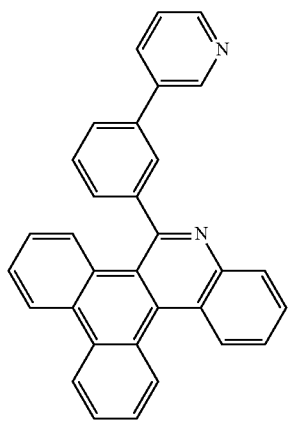
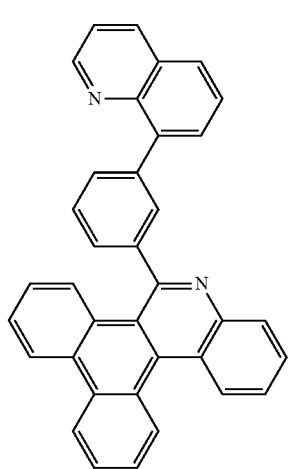
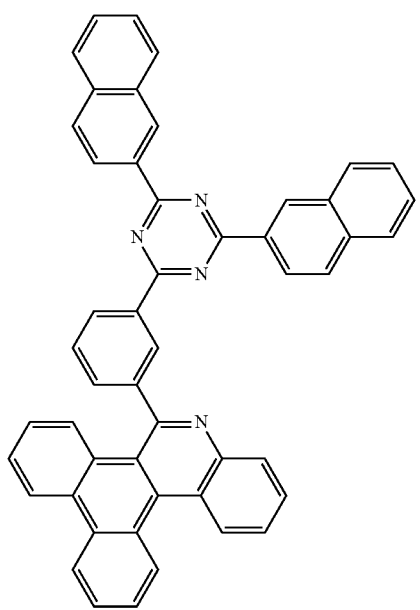
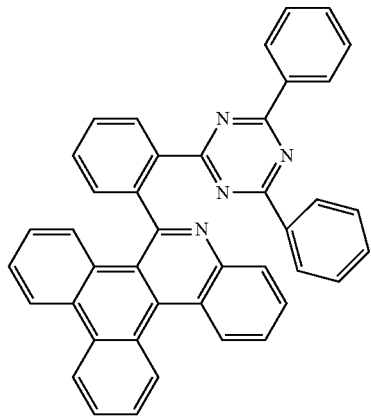

16
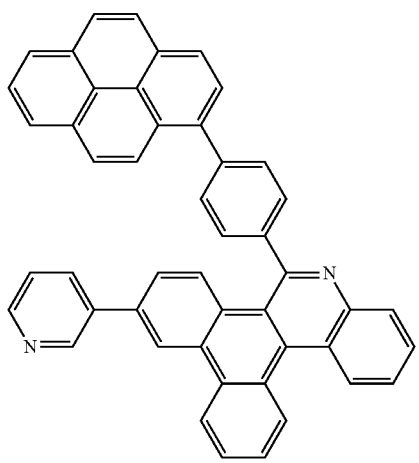
17
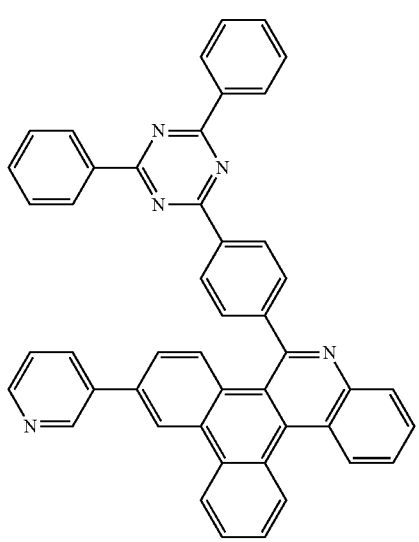
18
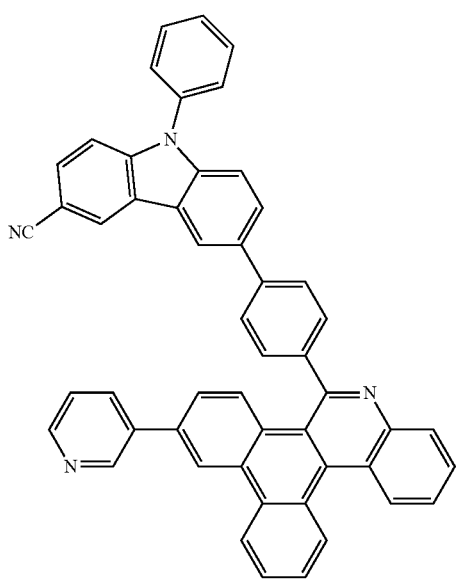
19
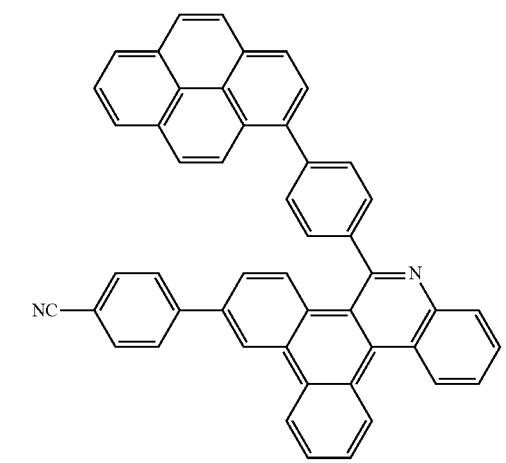
20
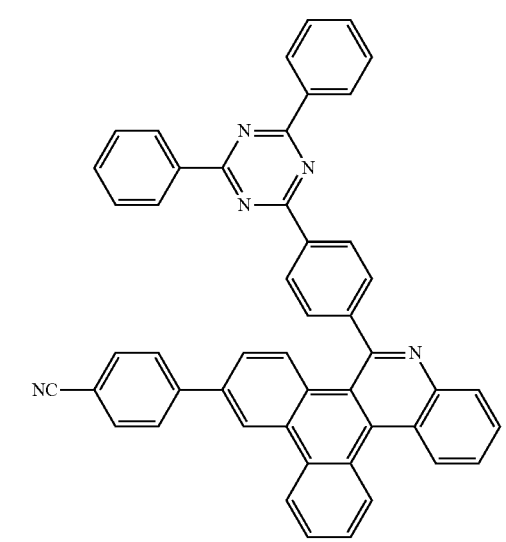
21

22
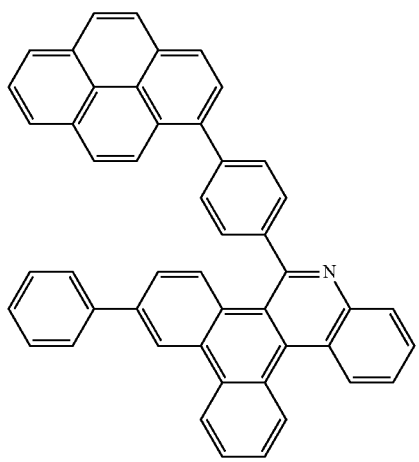
23
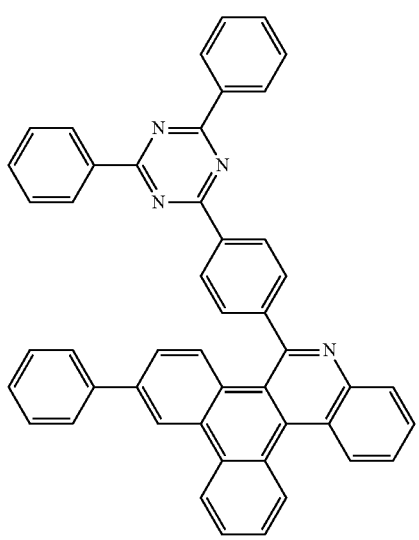
24
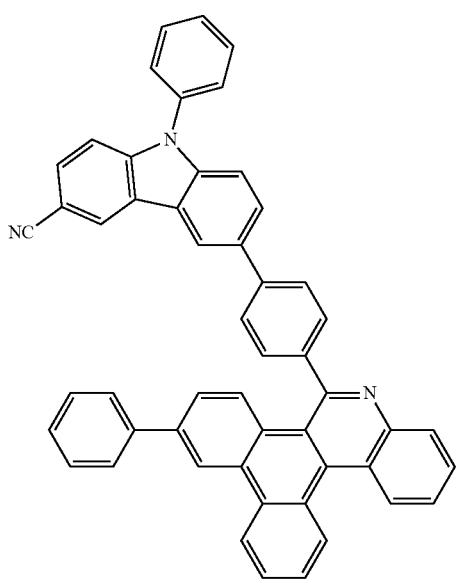
25
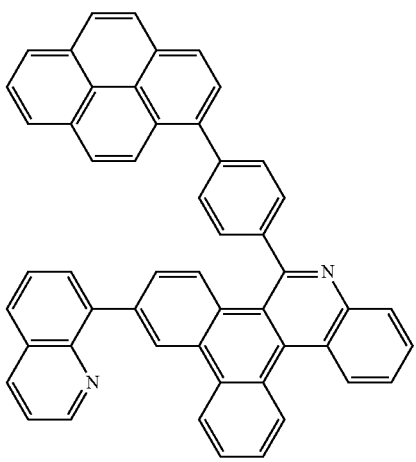
26
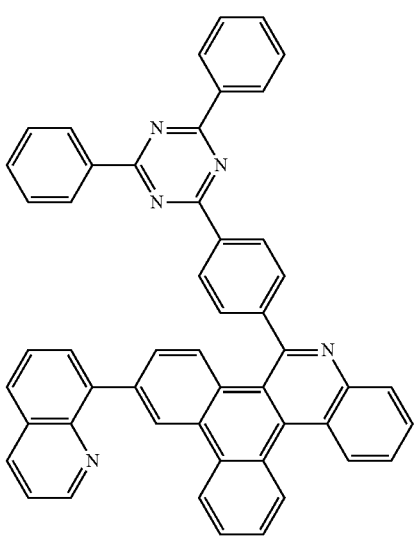
27
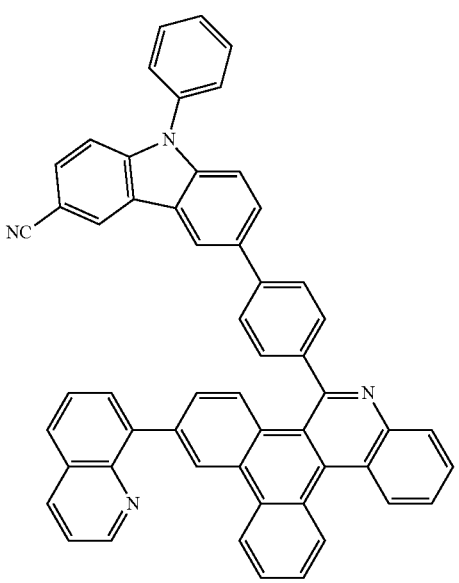

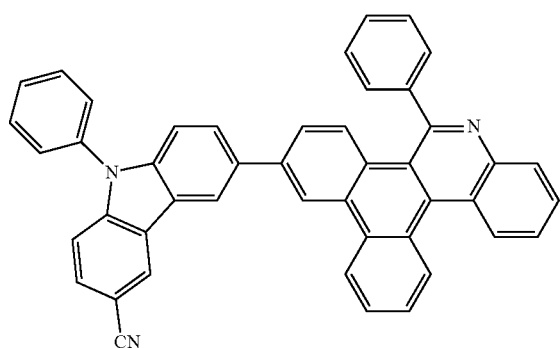
28
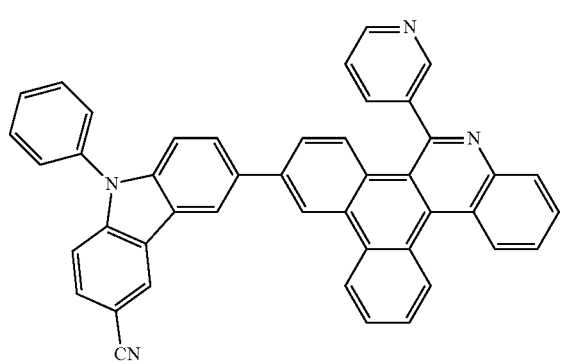
29
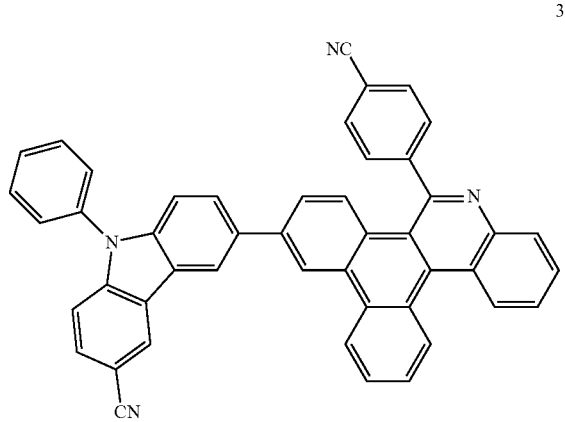
30
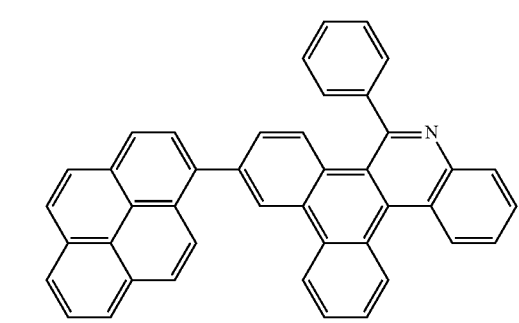
31
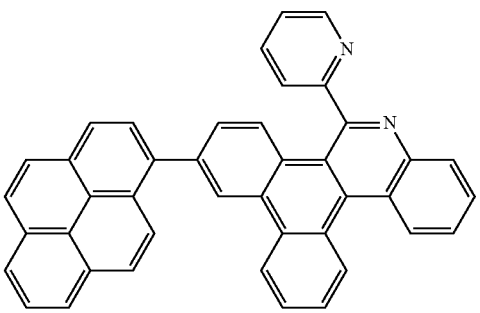
32
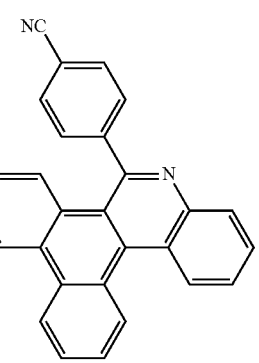
33
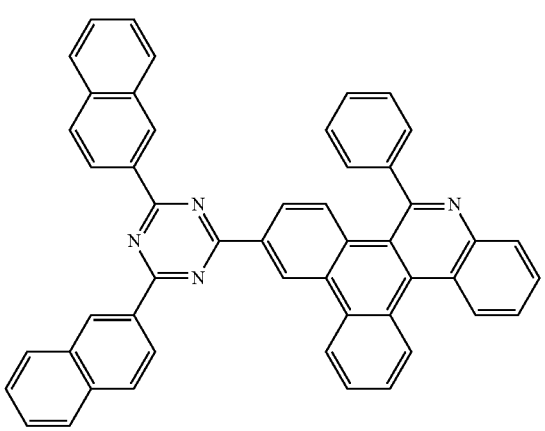
34
35

36
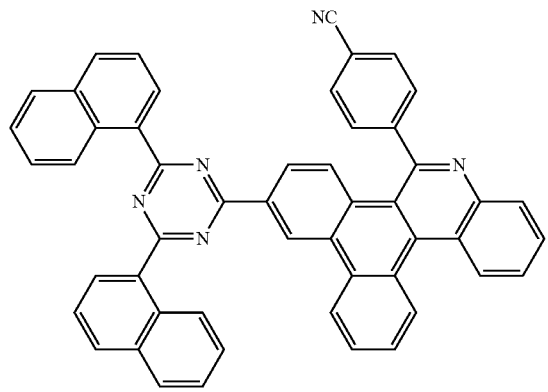
37
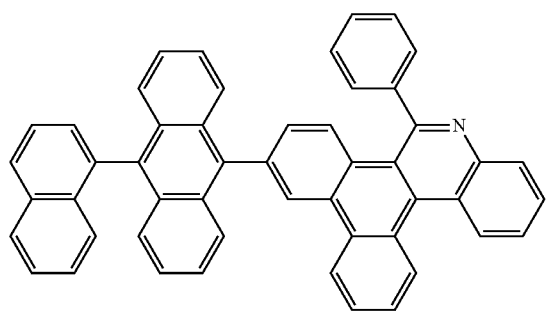
38
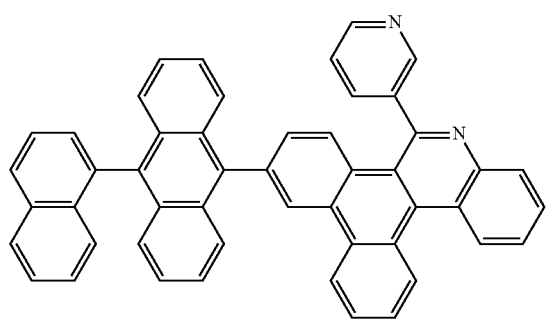
39
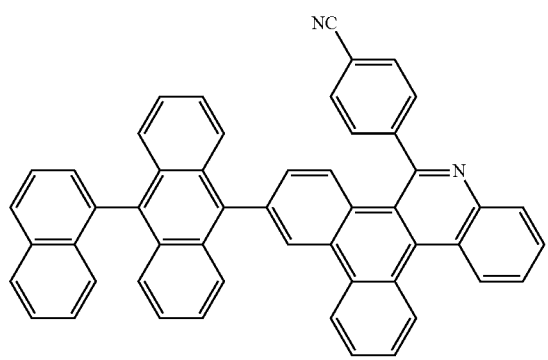
40
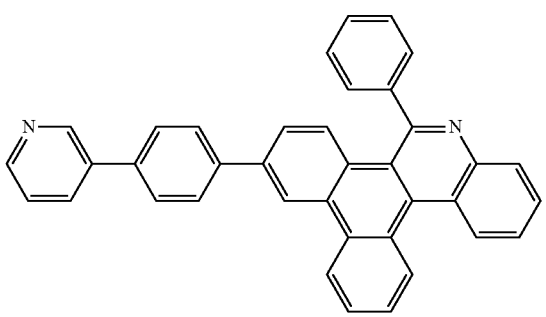
41
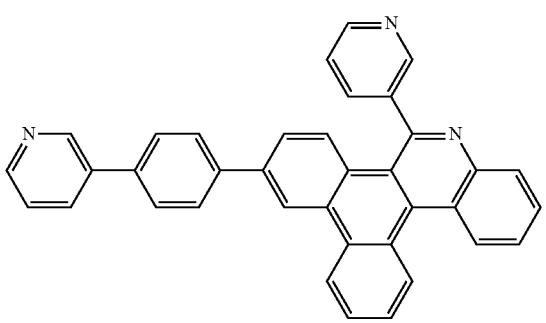
42
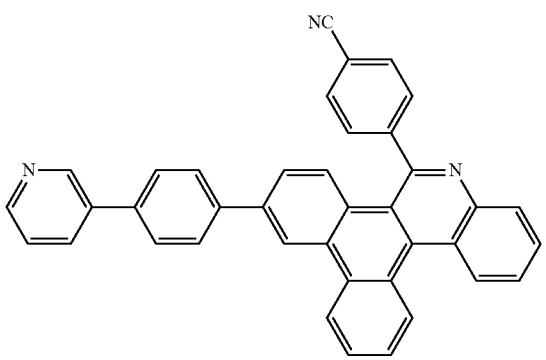
43
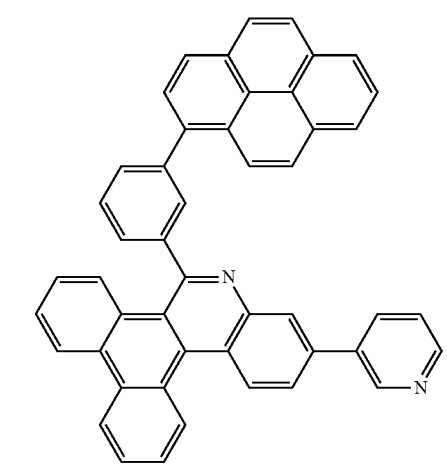

44
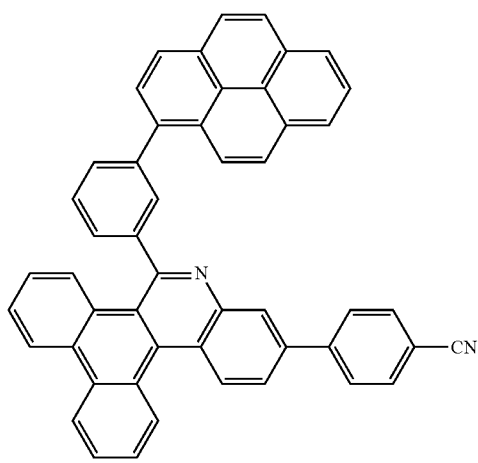
45
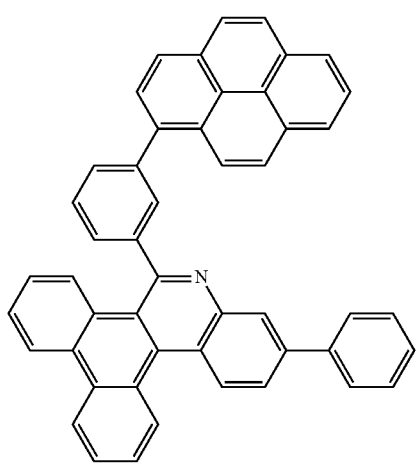
46
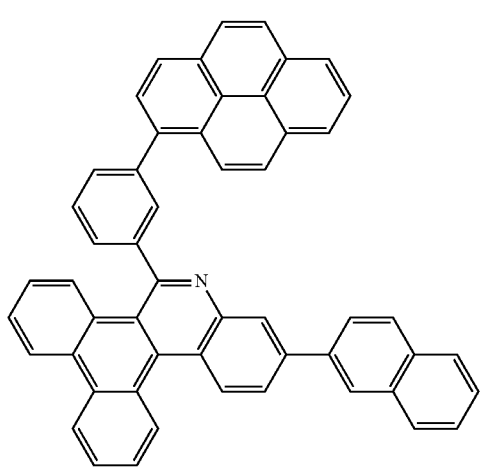
47
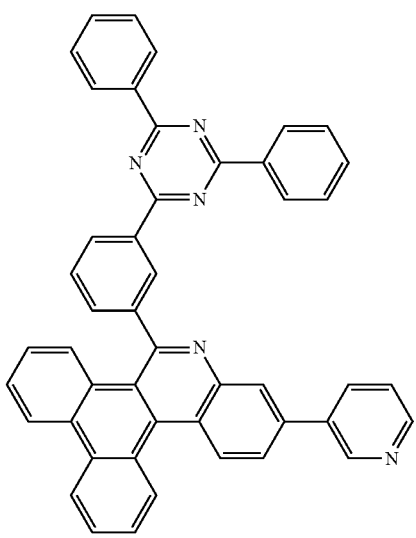
48
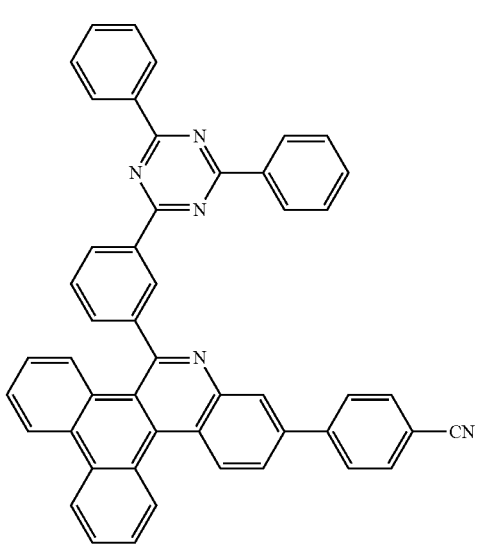
49
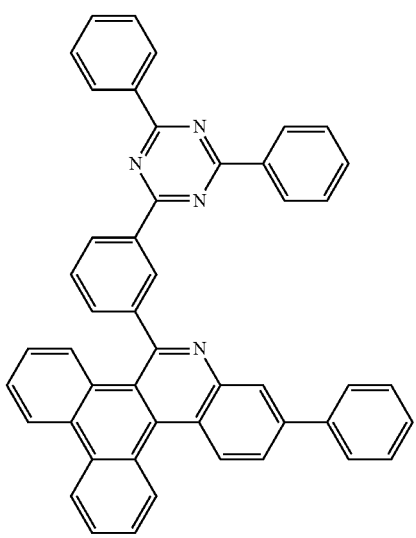

50
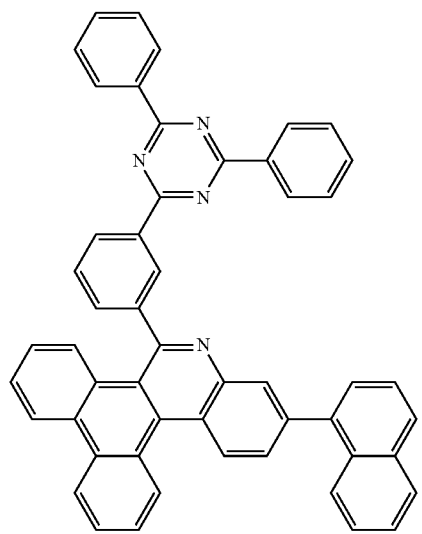
51
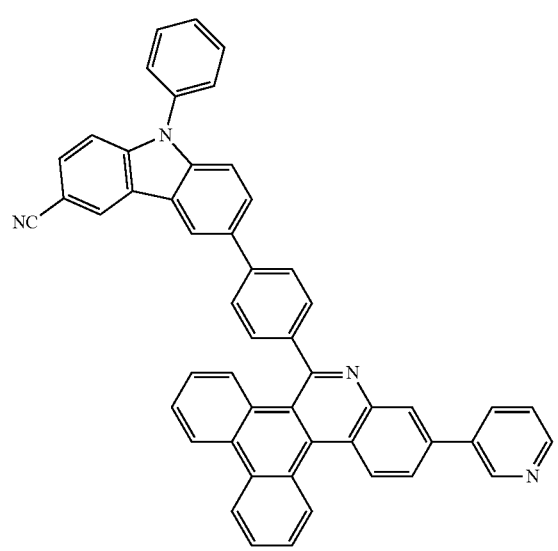
52
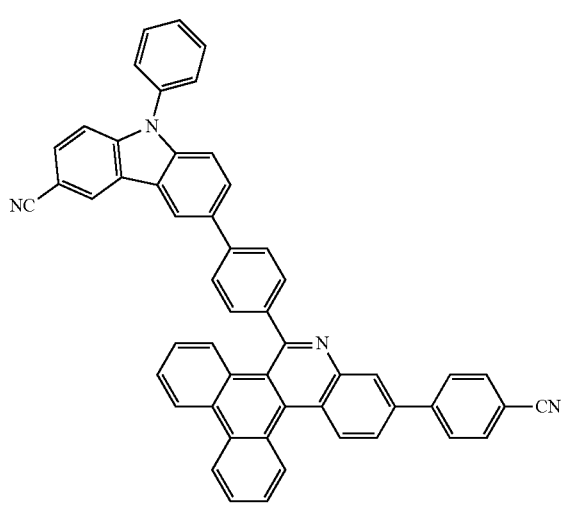
53
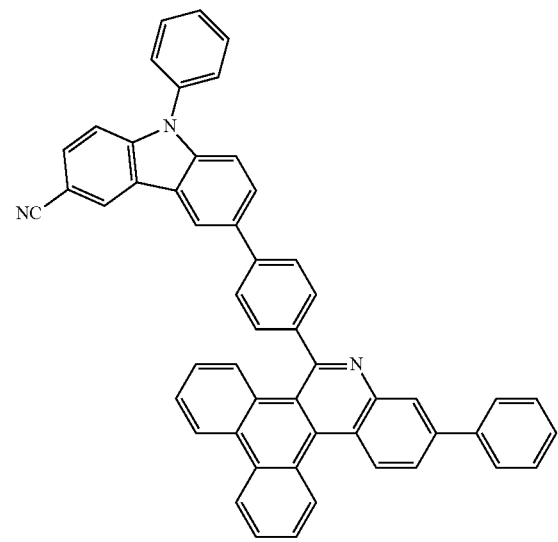
54
55
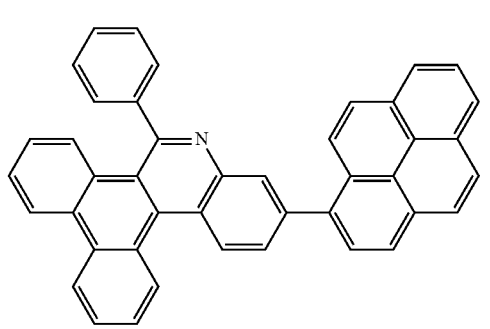

56
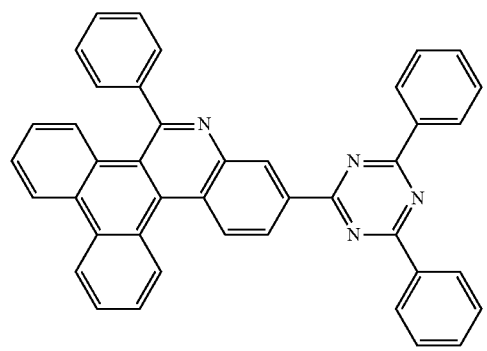
57
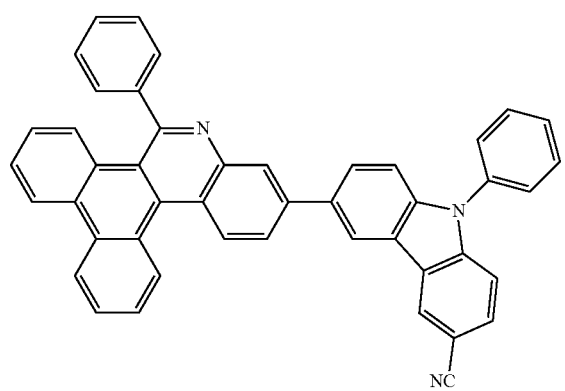
58
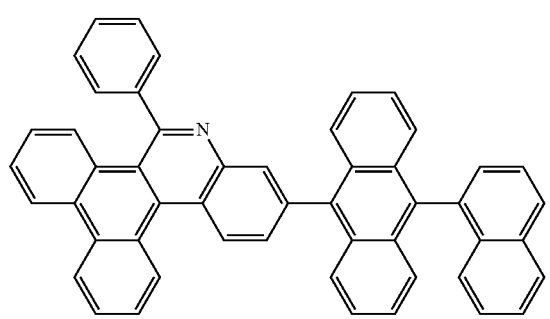
59
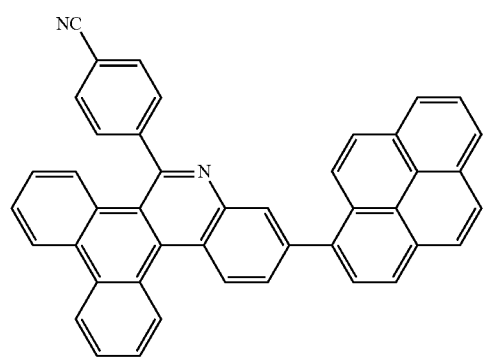
60
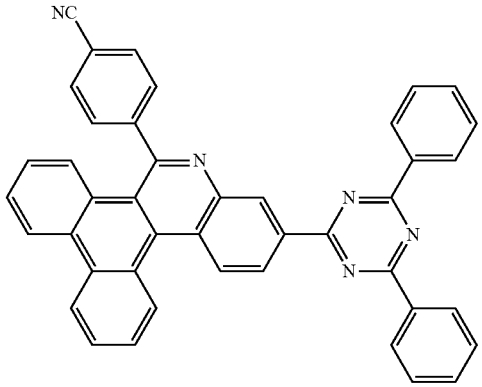
61
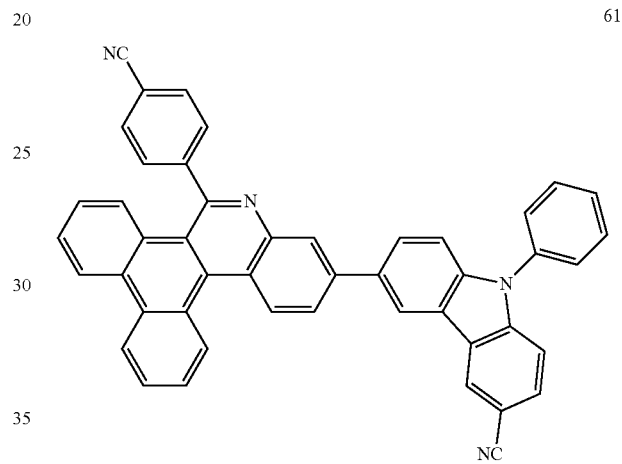
62
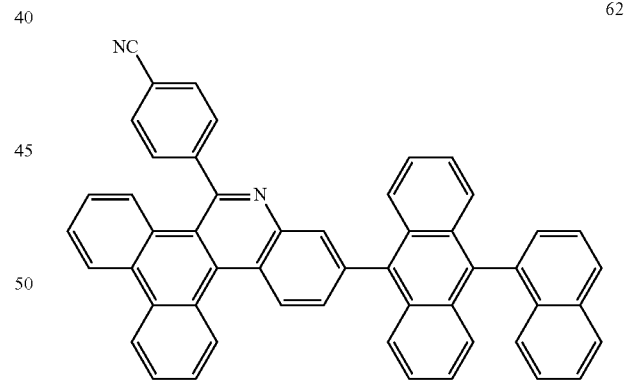
63
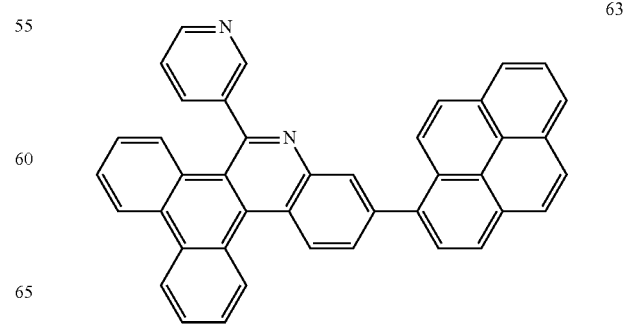

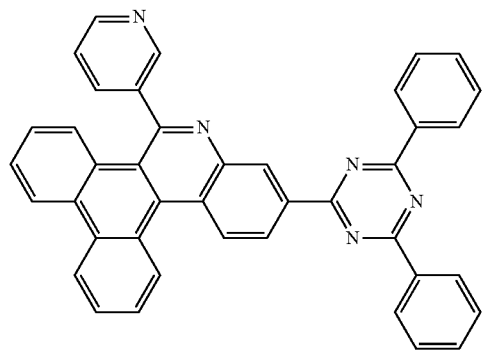
64
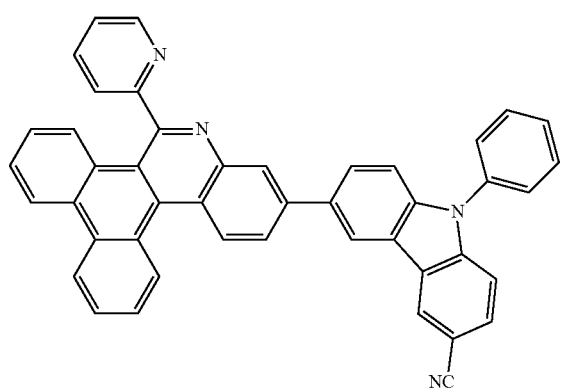
65
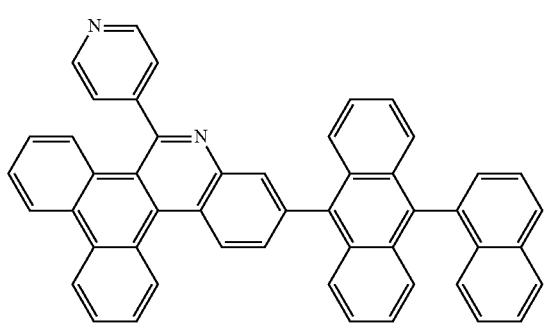
66
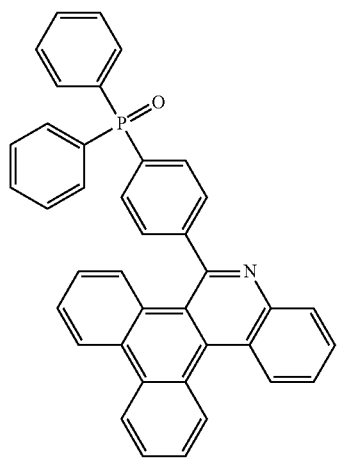
67
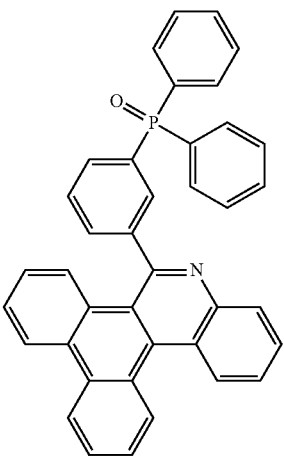
68
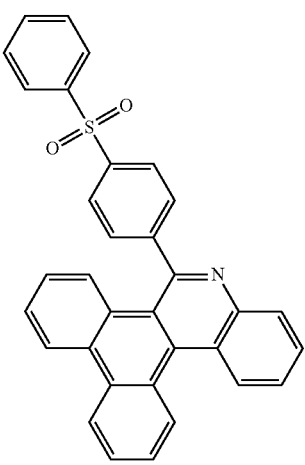
69
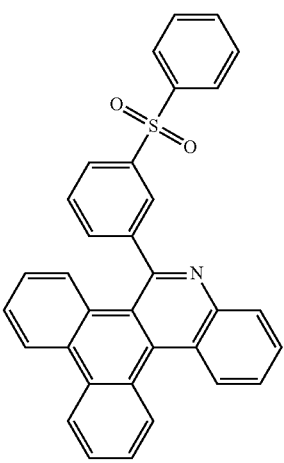
70

71
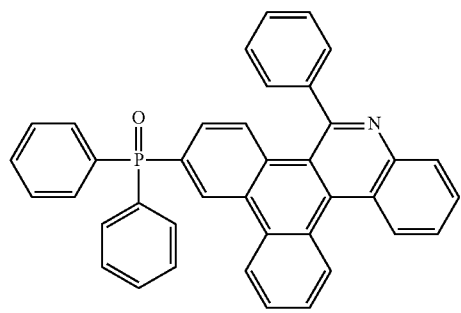
72
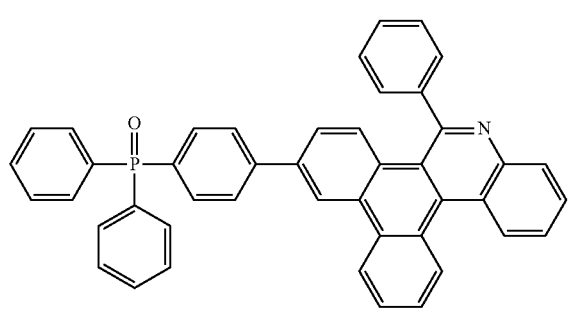
73
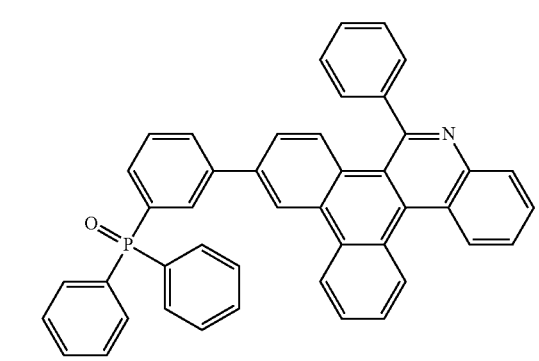
74
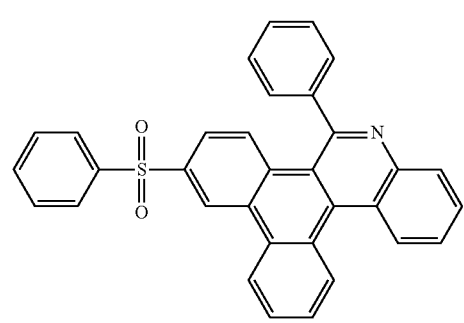
75
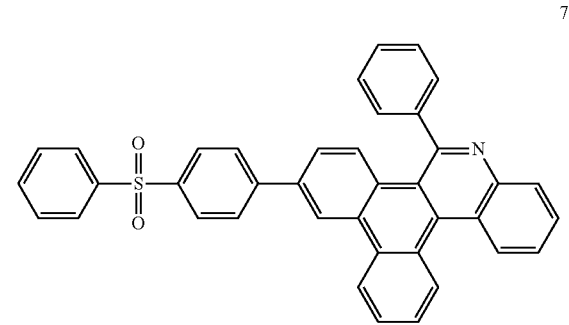
76
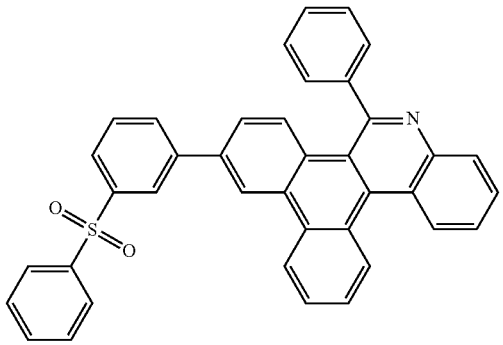
77
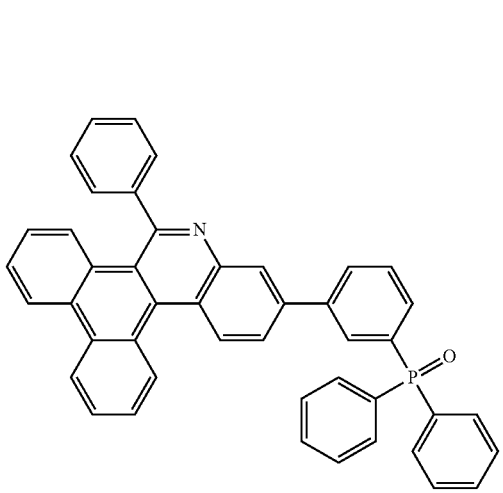
78
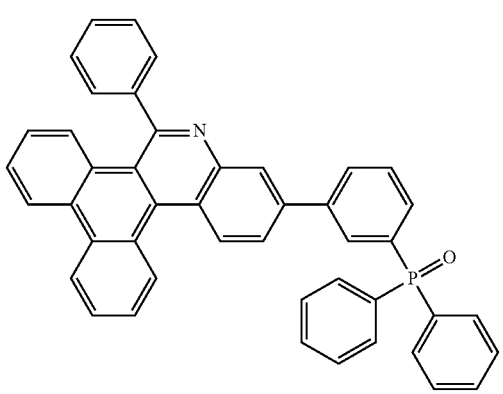
79
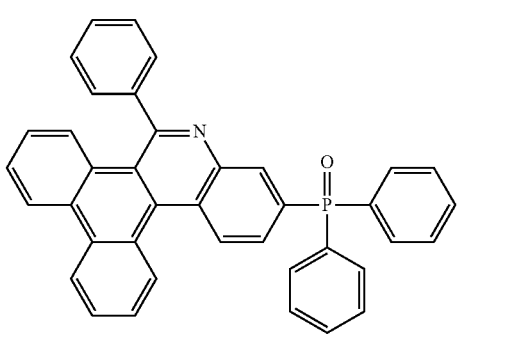

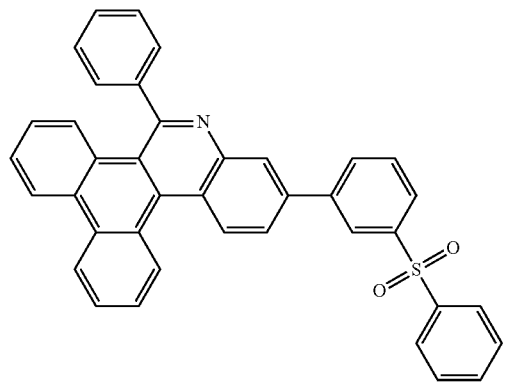

80

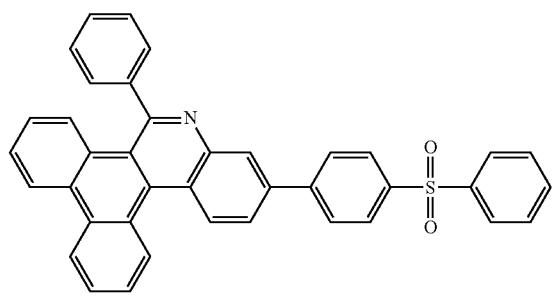

81

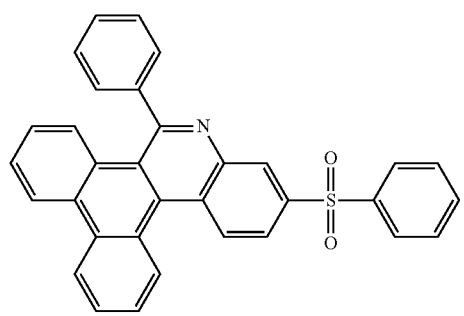

82

An organic light-emitting device including the condensed cyclic compound represented by Formula 1 above may have low driving voltage, high efficiency, high brightness, and long lifespan.

The condensed cyclic compound represented by Formula 1 above may be synthesized by using a suitable organic synthesis method. The method of synthesizing the condensed cyclic compound may be understood based on the embodiments described below.

The condensed cyclic compound represented by Formula 1 above may be used between a pair of electrodes in an organic light-emitting device. For example, the condensed cyclic compound may be included in an electron transport layer (ETL). Accordingly, provided is an organic light-emitting device including a first electrode, a second electrode disposed opposite to the first electrode, an organic layer disposed between the first electrode and the second electrode and including an emission layer (EML), wherein, the organic layer includes at least one type of condensed cyclic compound represented by Formula 1 described above.

As used herein, the expression "(organic layer) includes at least one of a first material" may be construed as "(organic layer) may include one of a first material in a range of Formula 1 or two or more different first materials in the range of Formula 1".

For example, the organic layer may only include Compound 1 as the condensed cyclic compound. In this regard, Compound 1 may only exist in the ETL or the organic light-emitting device. Alternatively, the organic layer may include Compound 1 and Compound 2 as the condensed cyclic compound. In this regard, Compound 1 and Compound 2 may exist in the same layer (for example, Compound 1 and Compound 2 may both exist in the ETL) or in different layers (for example, Compound 1 may only exist in the EML and Compound 2 may only exist in the ETL).

The organic layer include i) a hole transport region disposed between the first electrode and the emission layer (EML) and including at least one selected from a hole injection layer (HIL), a hole transport layer (HTL), a buffer layer, and an electron blocking layer (EBL); and ii) an electron transport region disposed between the EML and the second electrode and including at least one selected from a hole blocking layer (HBL), an ETL, and an EIL.

As used herein, the expression, the "organic layer" is a term that refers to a single layer and/or a multi-layer disposed between the first electrode and the second electrode in the organic light-emitting device. Materials included in the "organic layer" are not limited to organic materials.

The FIGURE schematically illustrates a structure of an organic light-emitting device according to an embodiment. The organic light-emitting device 10 may include a first electrode 110, an organic layer 150, and a second electrode 190.

Hereinafter, a structure and a method of manufacturing an organic light-emitting device according to an embodiment will be described with reference to the FIGURE.

A substrate may be additionally disposed under the first electrode 110 or on the second electrode 190 in the FIGURE. The substrate may be a glass substrate or a transparent plastic substrate with excellent mechanical strength, thermal stability, transparency, surface smoothness, ease of handling, and water resistance.

The first electrode 110 may be formed by, for example, depositing or sputtering a material for a first electrode 110 on the substrate. When the first electrode 110 is an anode, the material for the first electrode 110 may be selected from materials with a high work function to enable ease of hole injection. The first electrode 110 may be a reflective electrode, a semi-transmission electrode, or a transmission electrode. The material for the first electrode 110 may be a transparent material with high conductivity, and examples of such a material are indium tin oxide (ITO), indium zinc oxide (IZO), tin oxide ($SnO_2$), and zinc oxide (ZnO). To manufacture the first electrode 110, which is a semi-transmission electrode or a transmission electrode, at least one of magnesium (Mg), aluminum (Al), aluminum-lithium (Al—Li), calcium (Ca), magnesium-indium (Mg—In), magnesium-silver (Mg—Ag), or the like may be used.

The first electrode 110 may have a single-layer structure or a multi-layer structure including a plurality of layers. For example, the first electrode 110 may have a three-layered structure of ITO/Ag/ITO, but is not limited thereto.

The organic layer 150 may be disposed on the first electrode 110. The organic layer 150 includes an EML.

The organic layer 150 may further include a hole transport region disposed between the first electrode and the emission layer and an electron transport region disposed between the emission layer and the second electrode.

The hole transport region may include at least one selected from a HIL, a HTL, a buffer layer, and an EBL and the electron transport region may include at least one selected from a HBL, an ETL, and an EIL, but they are not limited thereto.

The hole transport region may include a single layer formed of a single material, a single layer formed of a plurality of different materials, or a multi-layered structure including a plurality of layers formed of a plurality of different materials.

For example, the ole transport region may have a single-layered structure formed of a plurality of different materials or a structure in which HIL/HTL, HIL/HTL/buffer layer, HIL/buffer layer, HTL/buffer layer, or HIL/HTL/EBL are sequentially layered on the first electrode 110, but it is not limited thereto.

When the hole transport region includes the HIL, the HIL may be formed on the first electrode 110 by using various methods, such as vacuum deposition, spin coating, casting, Langmuir-Blodgett (LB) deposition, inkjet printing, laser printing, and laser-induced thermal imaging (LITI).

When the HIL is formed by using vacuum deposition, vacuum deposition conditions may vary according to the compound that is used to form the HIL and the desired structure of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec, depending on the structure of the HIL to be formed.

When the HIL is formed by using spin coating, the coating conditions may vary according to the compound that is used to form the HIL and the desired structure of the HIL to be formed. For example, the coating rate may be in the range of about 2000 rpm to about 5000 rpm, and a temperature at which a heat treatment is performed may be in the range of about 80° C. to about 200° C.

When the hole transport region includes the HTL, the HTL may be formed on the first electrode 110 or on the HIL by using various methods, such as vacuum deposition, spin coating, casting, LB deposition, inkjet printing, laser printing, and LITI. When the HTL is formed by vacuum deposition or spin coating, vacuum deposition conditions and coating conditions may be the same as the vacuum deposition conditions and the coating conditions of the HIL.

The hole transport region may include at least one selected from m-MTDATA, TDATA, 2-TNATA, NBP, β-NPD, TPD, Spiro-TPD, Spiro-NPB, α-NPB, TAPC, HMTPD, 4,4',4"-tris(N-carbazolyl)triphenylamine(4,4',4"-tris(N-carbazolyl)triphenylamine) (TCTA), polyaniline/dodecylbenzenesulfonic acid (Pani/DBSA), Poly(3,4-ethylenedioxythiophene)/Poly(4-styrenesulfonate) (PEDOT/PSS), polyaniline/camphor sulfonic acid (pani/CSA), (polyaniline)/poly(4-styrenesulfonate) (PANI/PSS), a compound represented by Formula 201 below, and a compound represented by Formula 202 below.

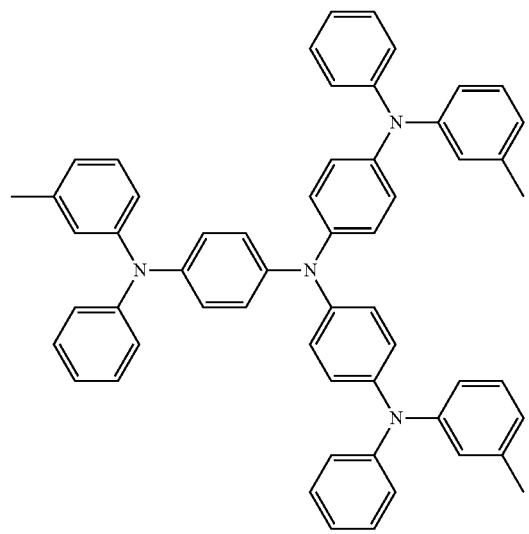

m-MTDATA

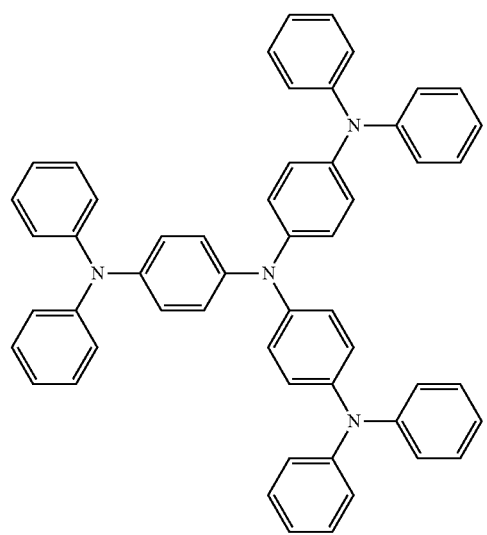

TDATA

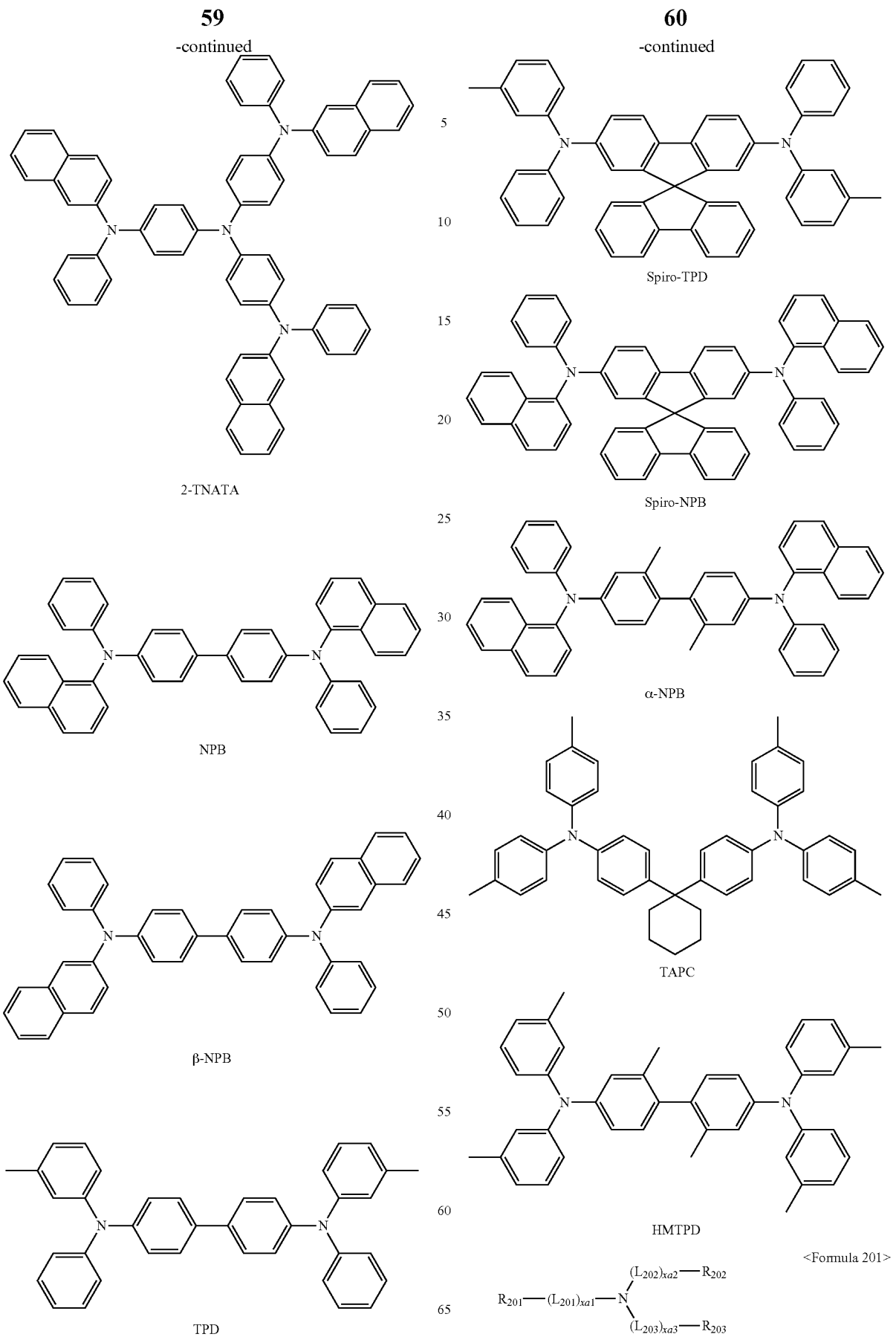

<Formula 202>

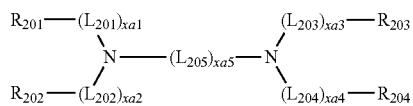

in Formulae 201 and 202, descriptions of $L_{201}$ to $L_{205}$ may be each independently understood by referring to the description of $L_1$ as described above;

xa1 to xa4 may be each independently selected from 0, 1, 2, and 3;

xa5 may be selected from 1, 2, 3, 4, and 5;

descriptions of $R_{201}$ to $R_{205}$ may be each independently understood by referring to the description of $R_1$.

For example, in Formulae 201 and 202, $L_{201}$ to $L_{205}$ may be each independently selected from a phenylene group, a naphthylene group, a fluorenylene group, a spiro-fluorenylene group, benzofluorene group, dibenzofluorene group, a phenanthrenylene group, an anthracenylene group, a pyrenylene group, chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group and a triazinylene group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently selected from 0, 1, or 2; and xa5 may be 1, 2, or 3;

$R_{201}$ to $R_{205}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, but they are not limited thereto.

The compound represented by Formula 201 above may be represented by Formula 201A below:

<Formula 201A>

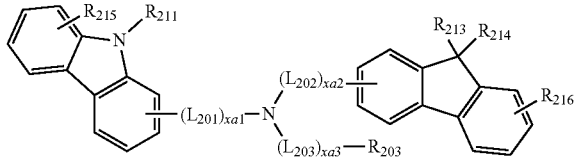

For example, the compound represented by Formula 201 above may be represented by Formula 201A-1 below, but it is not limited thereto:

<Formula 201A-1>

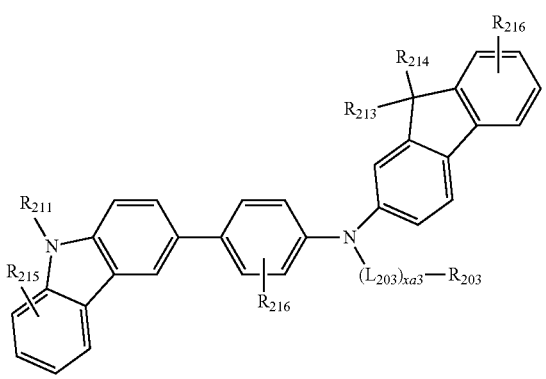

The compound represented by Formula 202 above may be represented by Formula 202A below, but it is not limited thereto:

<Formula 202A>

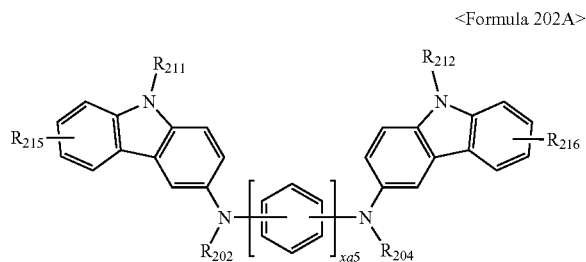

In Formulae 201A, 201A-1, and 202A, descriptions of $L_{201}$ to $L_{203}$, xa1 to xa3, xa5, and $R_{202}$ to $R_{204}$ may be understood by referring to the descriptions above, $R_{211}$ may be understood by referring to the description of $R_{203}$, and $R_{213}$ to $R_{216}$ may be each independently selected from hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, and a monovalent non-aromatic condensed hetero-polycyclic group.

For example, in Formulae 201A, 201A-1, and 202A, $L_{201}$ to $L_{203}$ may be each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group and a triazinylene group, each substituted with at least one selected from deuterium, —F, —Cl, —Br, —I, a hydroxyl group, a cyano group, a nitro group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$ and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group;

$R_{213}$ and $R_{214}$ may be ach independently selected from $C_1$-$C_{20}$ alkyl and a $C_1$-$C_{20}$ alkoxy;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic group or a salt thereof, sulfonic acid group or a salt thereof, phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a slat thereof, phosphoric acid group or a salt thereof, a $C_1$-$C_{20}$ alkyl group and a $C_1$-$C_{20}$ alkoxy group;

a $C_1$-$C_{20}$ alkyl and a $C_1$-$C_{20}$ alkoxy, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In Formulae 201A and 201A-1 above, $R_{213}$ and $R_{214}$ may bind to each other to form a saturated ring or an unsaturated ring.

The compound represented by Formula 201 above and the compound represented by Formula 202 above may include Compounds HT1 to HT20, but they are not limited thereto.

HT1

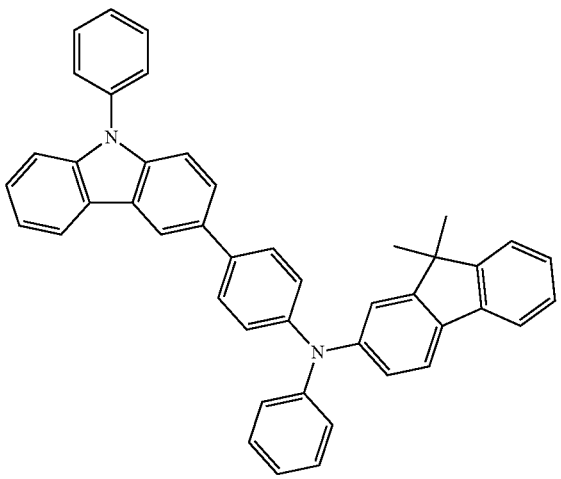

HT2

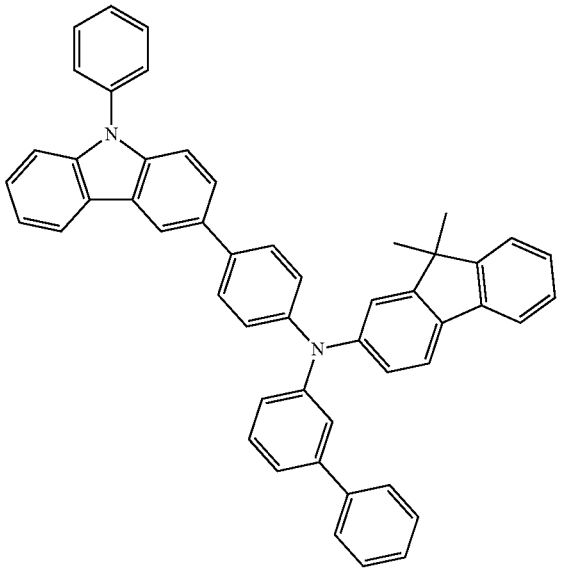

HT3
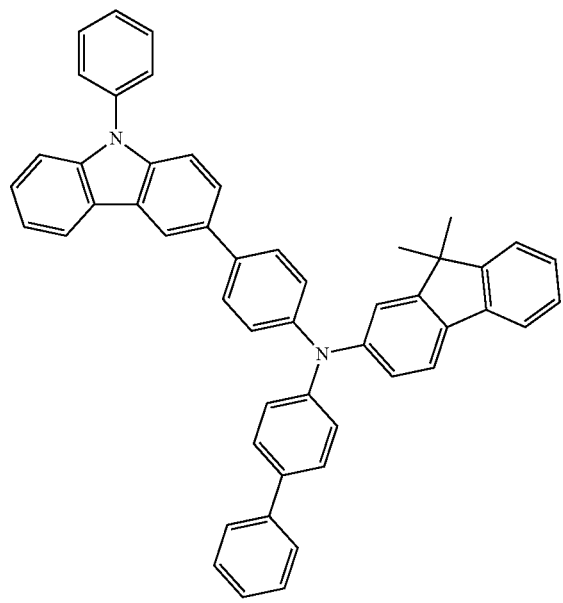
HT5
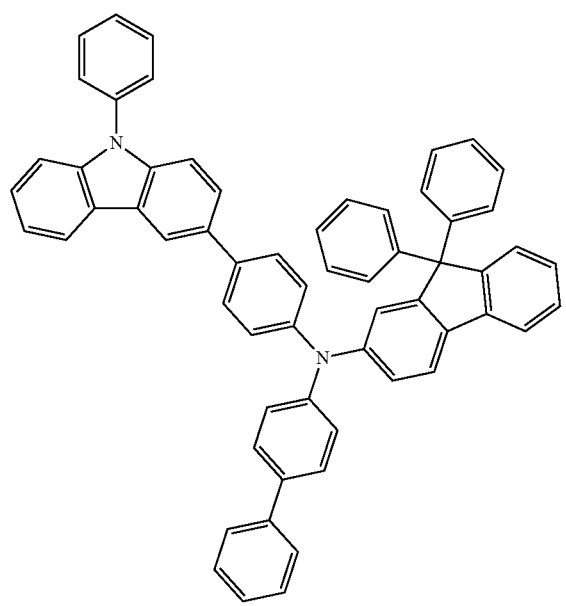
HT4
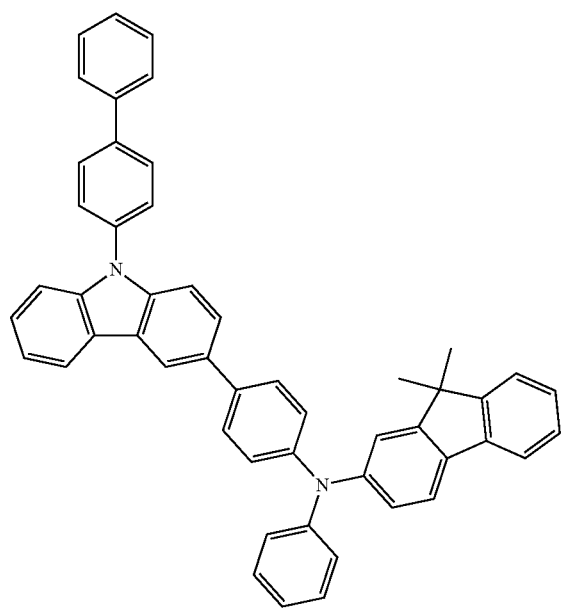
HT6
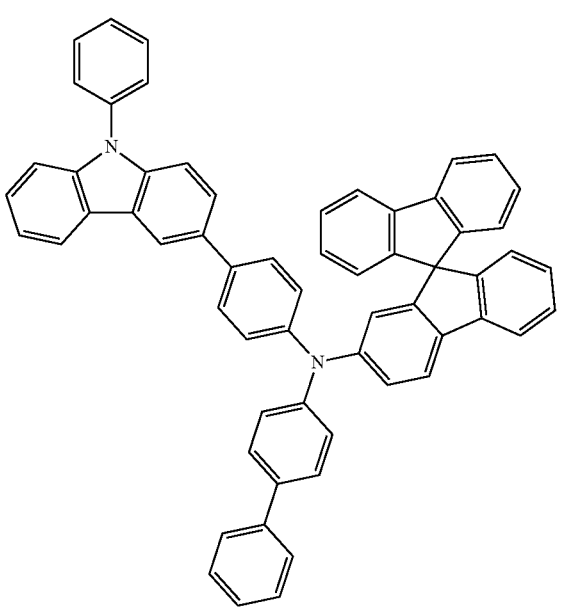

-continued
HT7
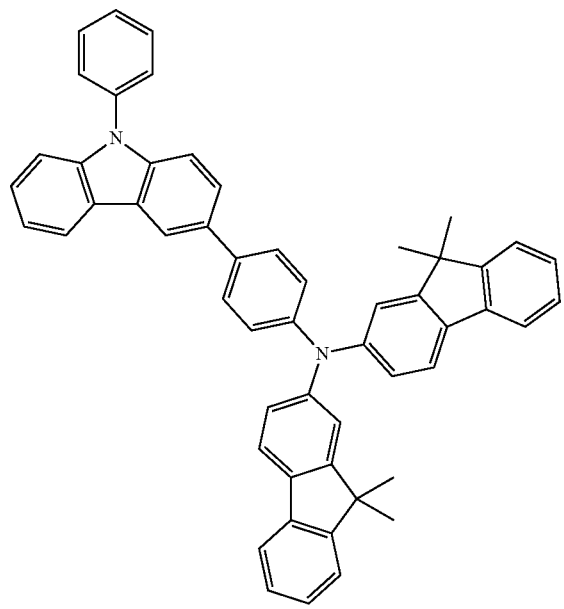
HT8
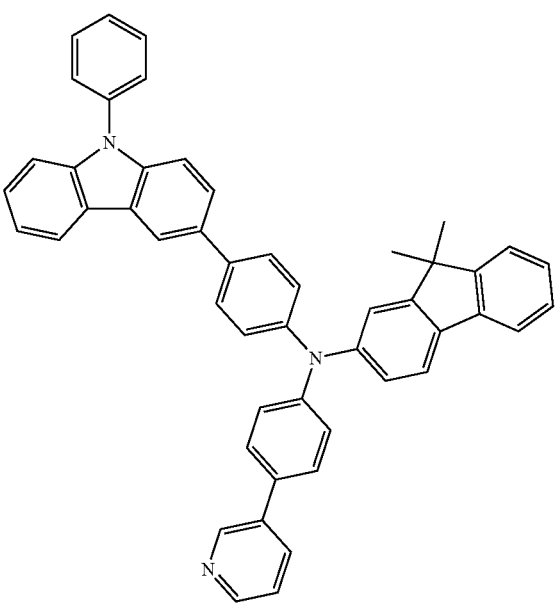
HT9
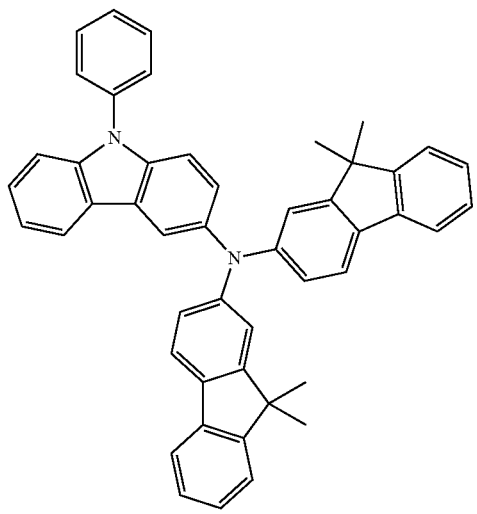
HT10

HT11
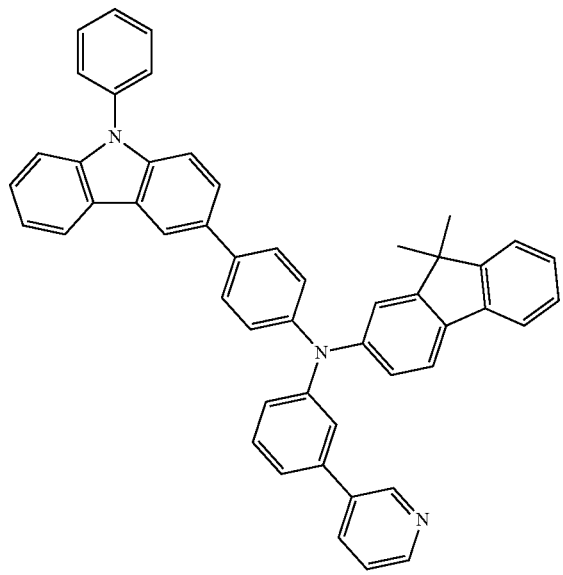
HT12
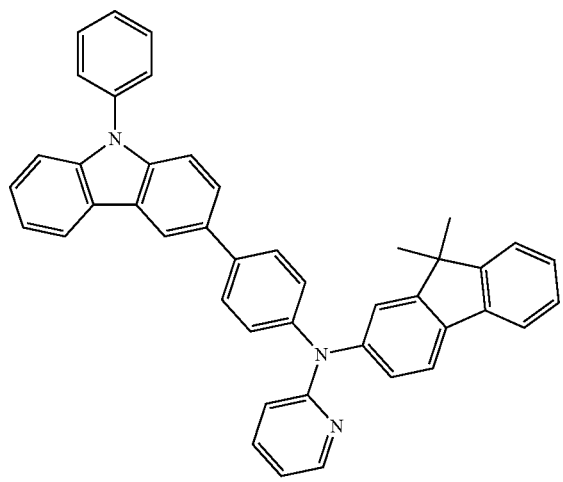
HT13
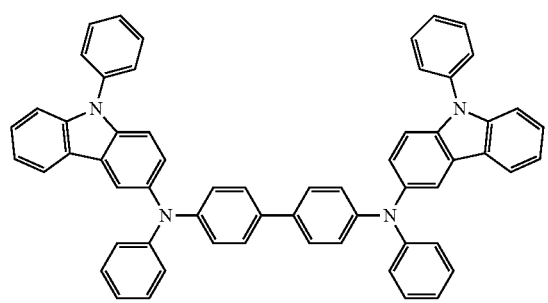
HT14
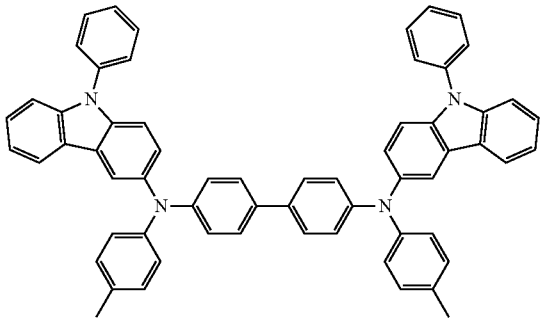
HT15
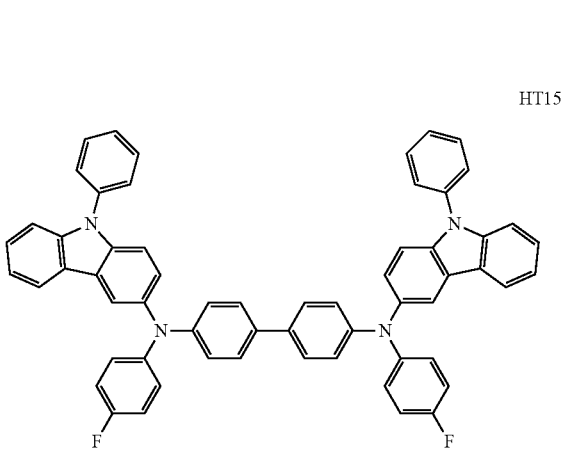
HT16
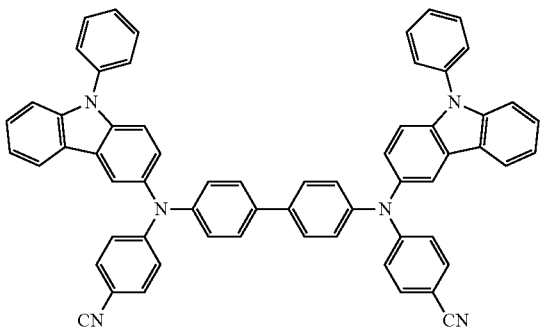
HT17
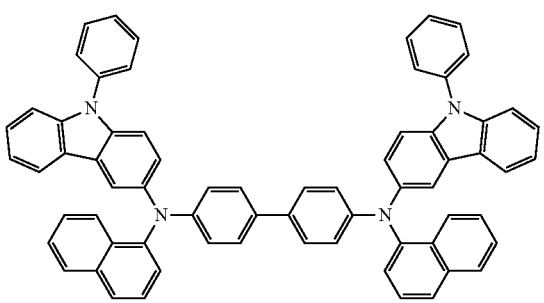

HT18

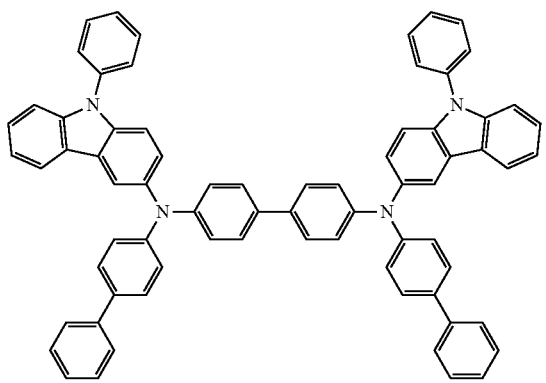

HT19

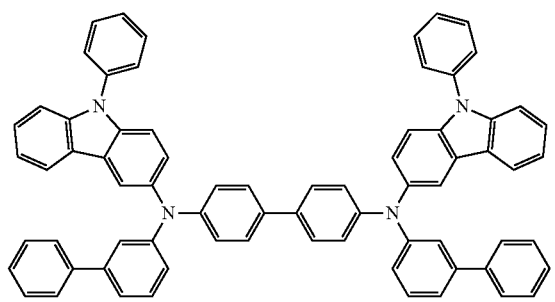

HT20

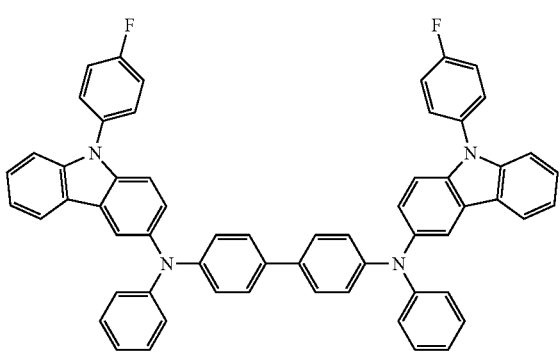

A thickness of the hole transport region may be about 100 Å to about 10,000 Å, for example about 100 Å to about 1,000 Å. When the hole transport region includes both of the HIL and the HTL, a thickness of the HIL may be about 100 Å to about 10000 Å, for example, about 100 Å to about 1,000 Å and a thickness of the HTL may be about 50 Å to about 2,000 Å, for example, about 100 Å to about 1500 Å. When the thickness of the hole transport region, the HIL, and the HTL satisfy the ranges described above, satisfactory hole injection characteristics may be obtained without a substantial increase in a driving voltage.

The hole transport region may further include a charge-generating material, in addition to the material described above. The charge-generating material may be uniformly or disuniformly dispersed in the hole transport region.

The charge-generating material may be, for example, a p-dopant. The p-dopant may be selected from quinone derivatives, metal oxides, and CN-containing compounds, but it is no limited thereto. For example, non-limiting examples of the p-dopant are quinone derivatives, such as tetracyanoquinodimethane (TCNQ), and 2,3,5,6-tetrafluoro-tetracyano-1,4-benzoquinodimethane (F4-TCNQ); metal oxides such as tungsten oxides and molybdenym oxides; and Compound HT-D1 below.

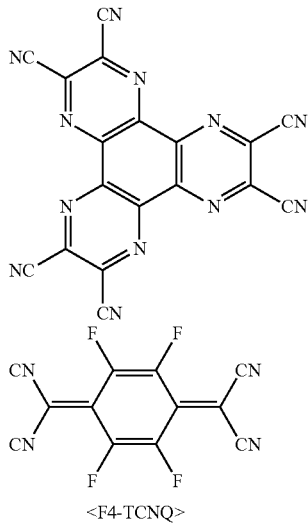

<Compound HT-D1>

<F4-TCNQ>

The hole transport region may include at least one selected from the buffer layer and the EBL, in addition to the HIL and the HTL. The buffer layer may compensate for an optical resonance distance of light according to a wavelength of the light emitted from the emission layer (EML), and thus may increase efficiency of light emission. The buffer layer may include any material that may be used in the hole transport region. The EBL may prevent injection of electrons from the electron transport region.

Then, the EML may be formed on the first electrode 110 or the hole transport region by vacuum deposition, spin coating, casting, LB deposition, inkjet printing, laser printing, LITI, or the like. When the EML is formed using vacuum deposition or spin coating, the deposition and coating conditions may be similar to those for the formation of the HIL.

When the organic light-emitting device 10 is a full color organic light-emitting device, the organic light-emitting device 10 may be patterned into red EML, green EML, and blue EML, according to different EMLs and the individual sub-pixels. Alternatively, the EML may have a structure in which the red EML, the green EML, and the blue EML are layered or a structure in which a red light emission material, a green light emission material, and a blue light emission material are mixed without separation of layers and emit white light. Alternatively, the EML is a white light EML, which includes a color filter or a color converting layer that converts white light into light of desired color.

The EML may include a host and a dopant.

The host may include at least one selected from TPBi, TBADN, ADN (also known as "DNA"), CBP, CDBP, and TCP:

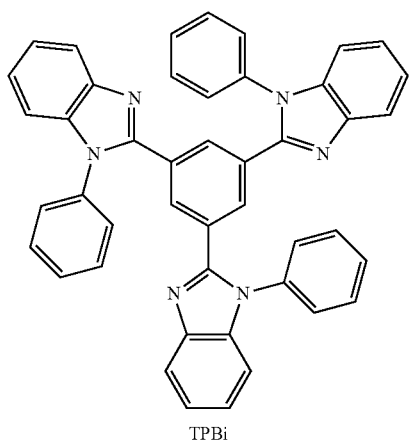

TPBi

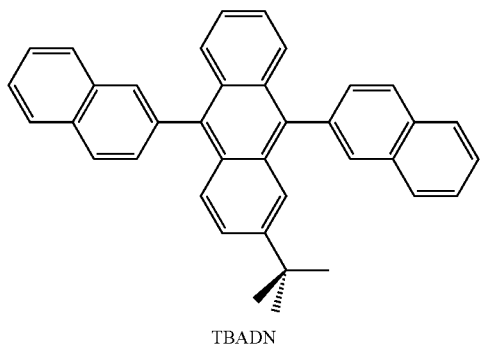

TBADN

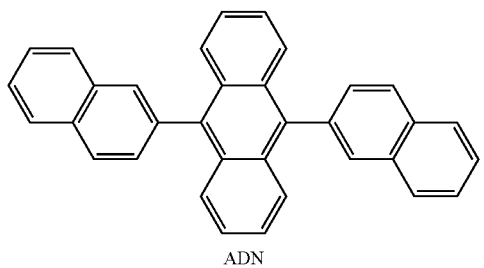

ADN

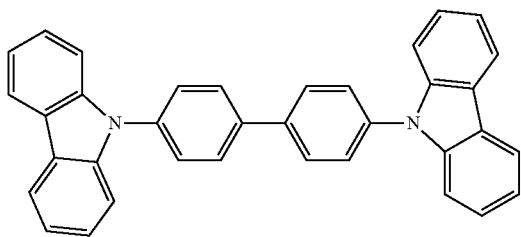

CBP

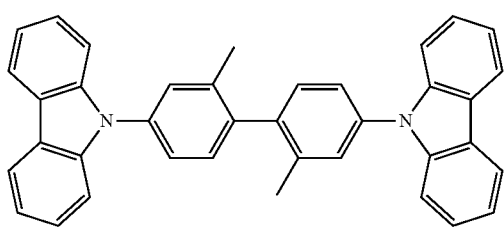

CDBP

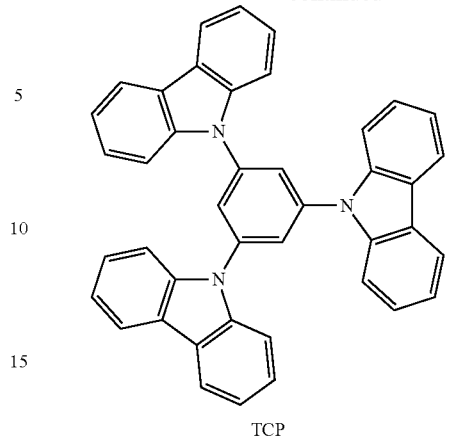

TCP

In an implementation, the host may include a compound represented by Formula 301 below.

$$Ar_{301}-[(L_{301})_{xb1}-R_{301}]_{xb2}$$  <Formula 301> in Formula 301, $Ar_{301}$ may be selected from naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene;

naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene and indenoanthracene, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_2$-$C_{60}$ heteroaryl group, a monovalent non-aromatic condensed polycyclic group, a monovalent non-aromatic condensed hetero-polycyclic group and —Si($Q_{301}$)($Q_{302}$)($Q_{303}$) (wherein, $Q_{301}$ to $Q_{303}$ may be each independently selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

description of $L_{301}$ may be understood by referring to the description of $L_{201}$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group;

xb1 may be selected from 0, 1, 2, and 3; and xb2 may be selected from 1, 2, 3, and 4.

For example, in Formula 301 above, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group and a chrysenyl group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but it is not limited thereto.

For example, the host may include a compound represented by Formula 301A below:

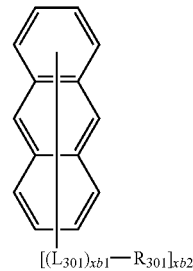

<Formula 301A>

$[(L_{301})_{xb1}$—$R_{301}]_{xb2}$

In Formula 301A above, descriptions of the substituents may be understood by referring to the descriptions herein.

The compound represented by Formula 301 above may include at least one selected from Compounds H1 to H42, but it is not limited thereto.

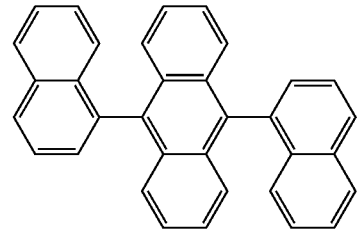

H1

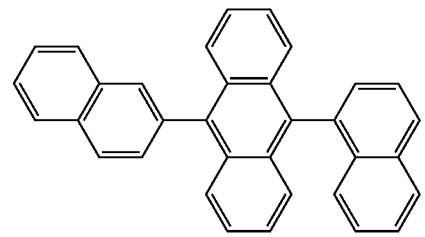

H2

-continued
H3
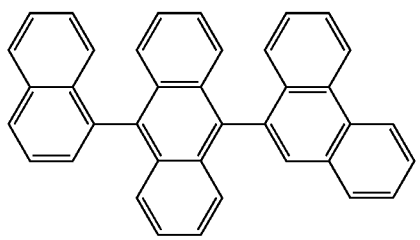
H4
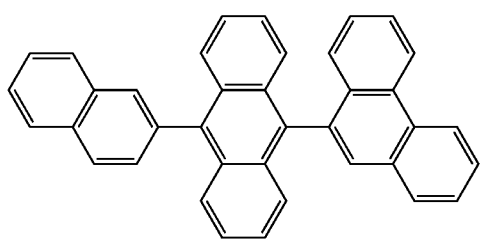
H5
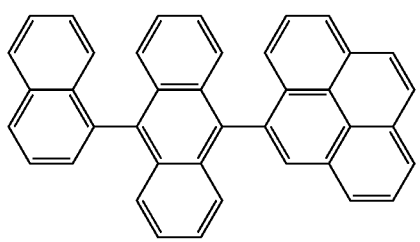
H6
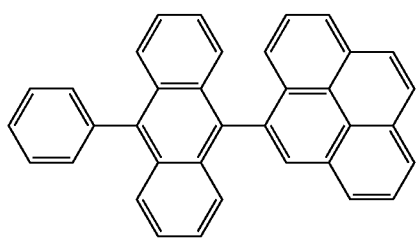
H7
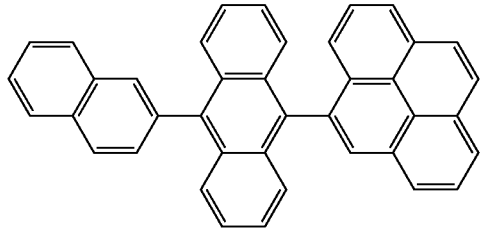
H8
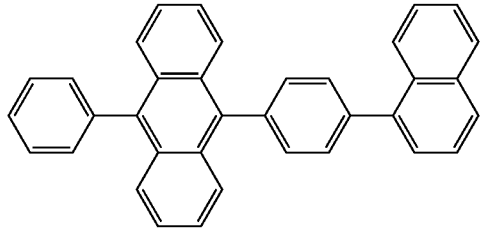
-continued
H9
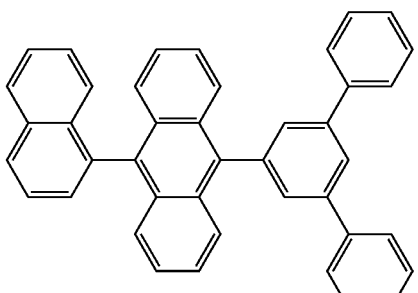
H10
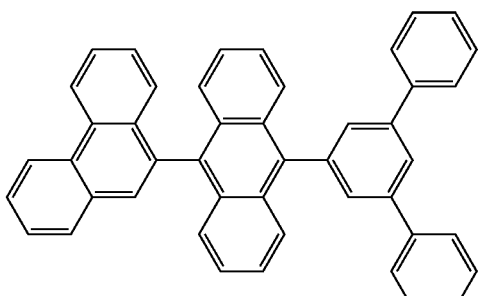
H11
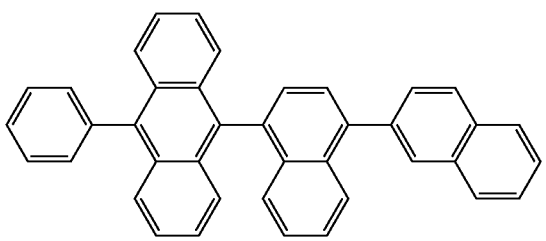
H12
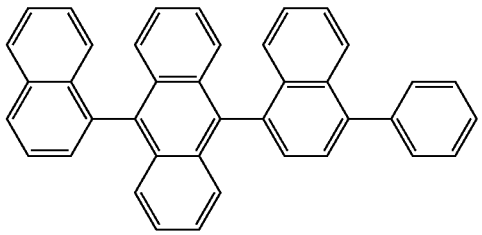
H13
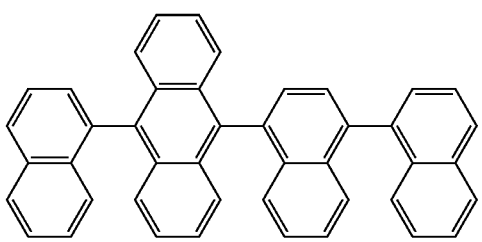
H14
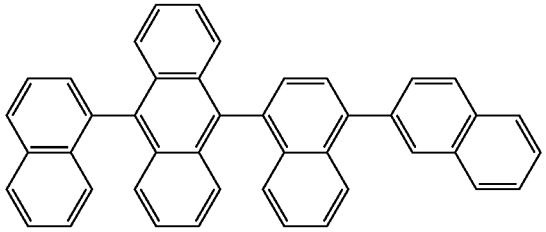

H15
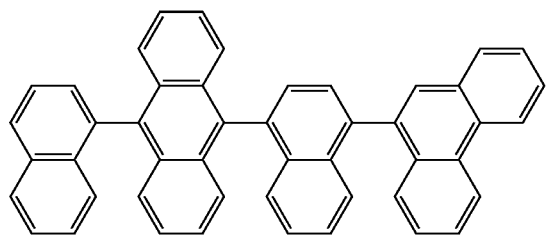
H16
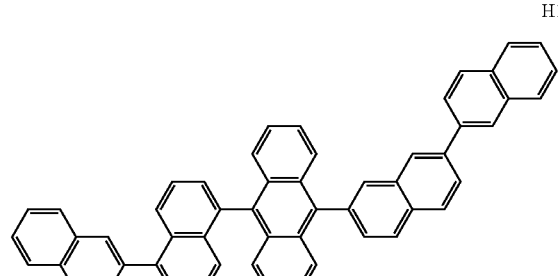
H17
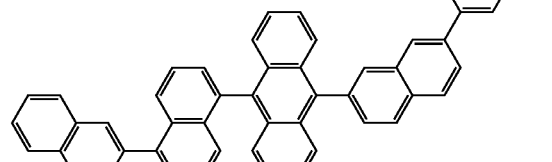
H18
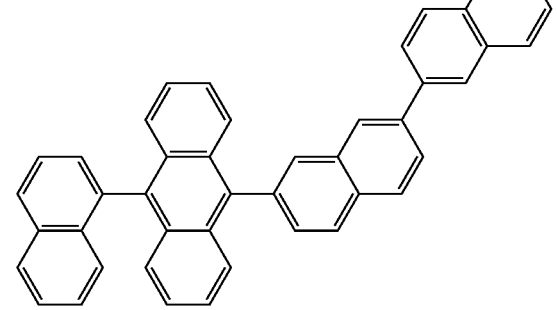
H19
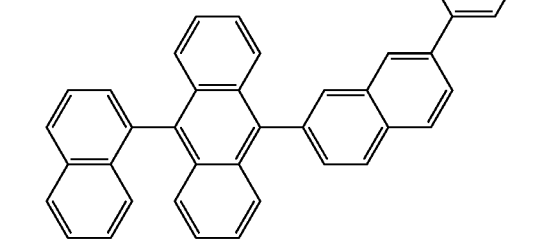
H20
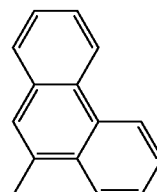
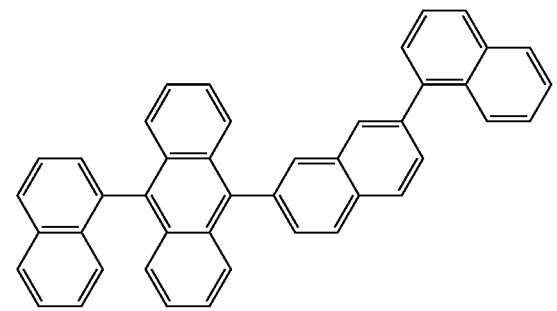
H21
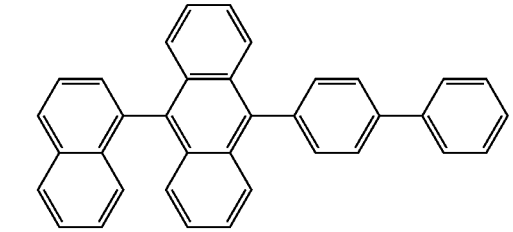
H22
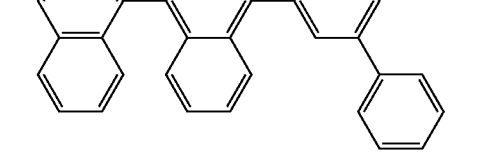
H23
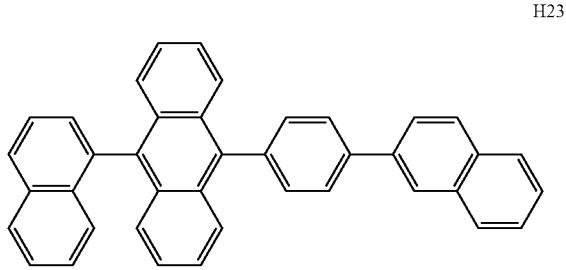
H24
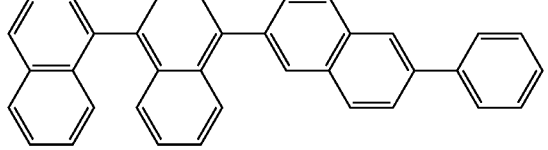

H25
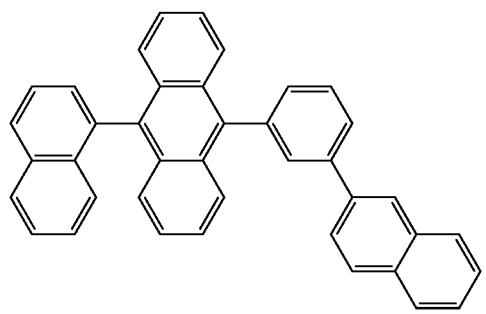
H26
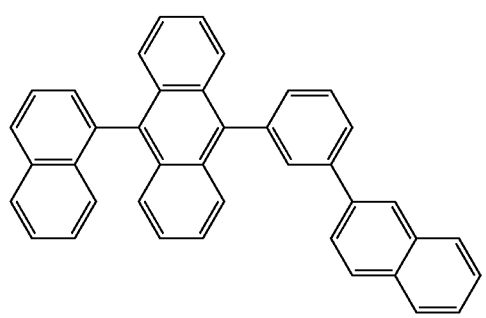
H27
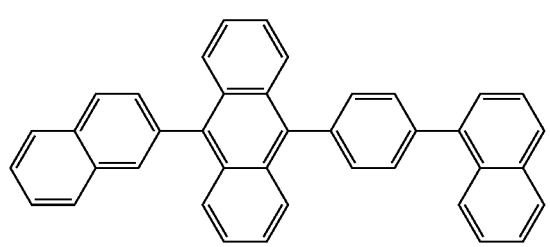
H28
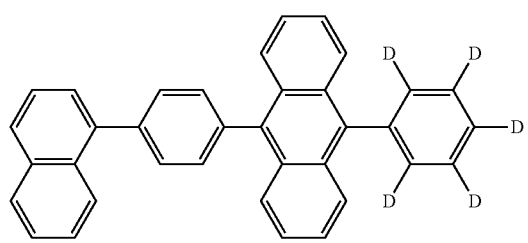
H29
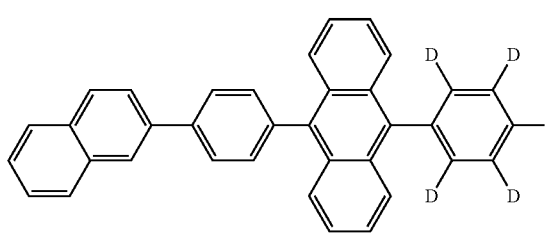
H30
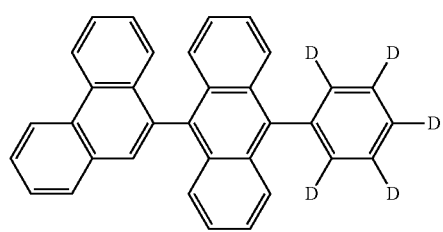
H31
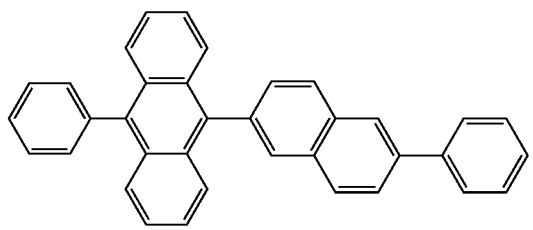
H32
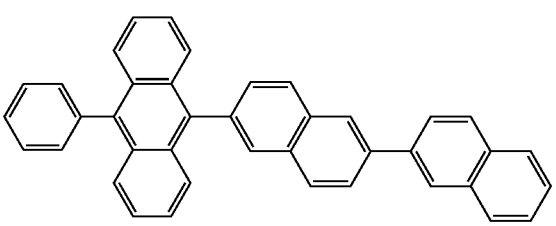
H33
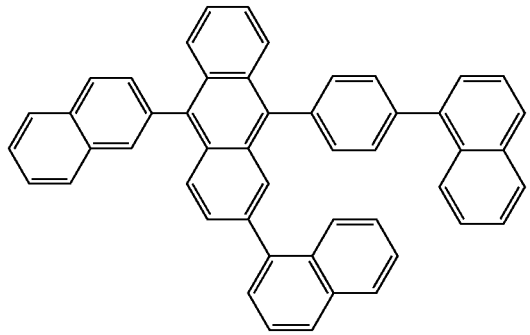
H34
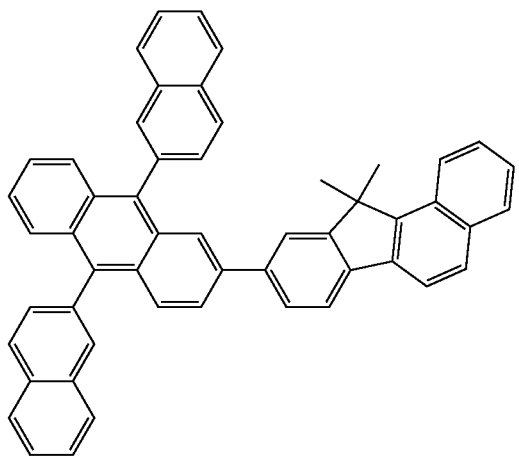

H35
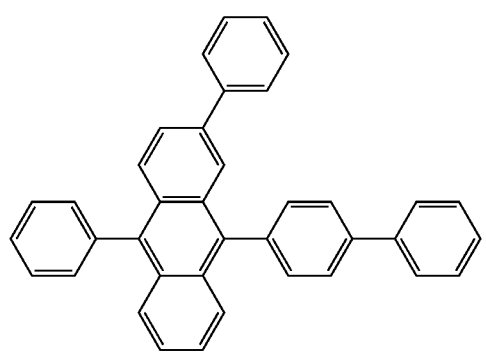
H36
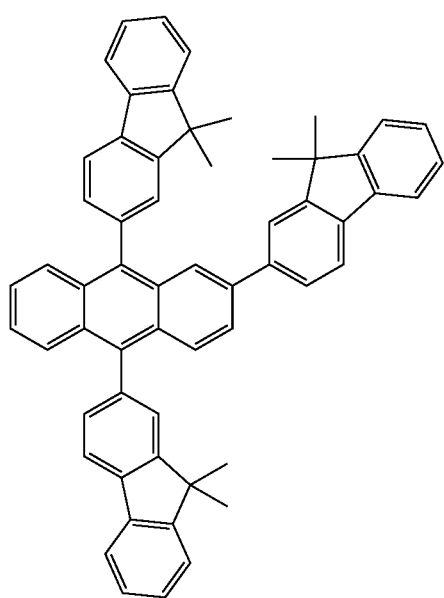
H37
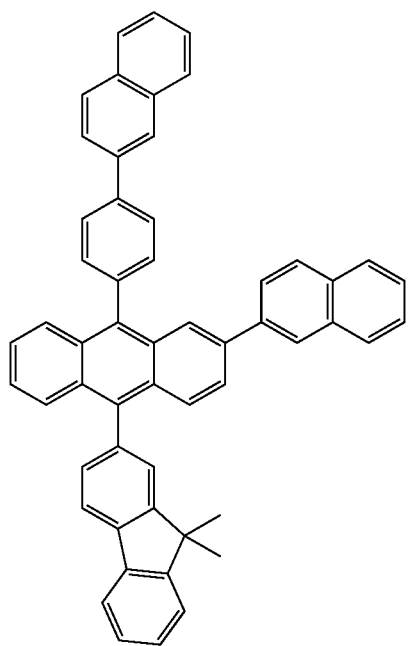
H38
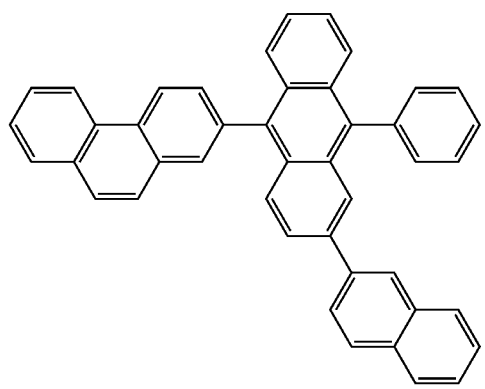
H39
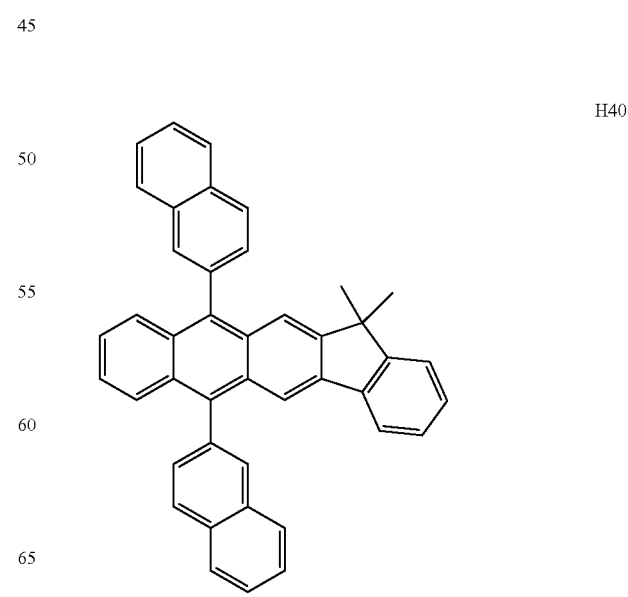
H40

H41
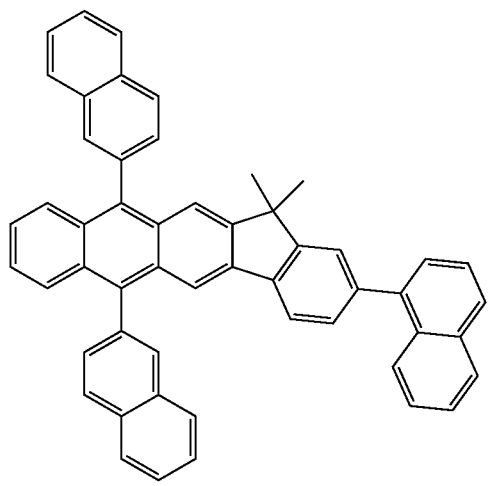
H42
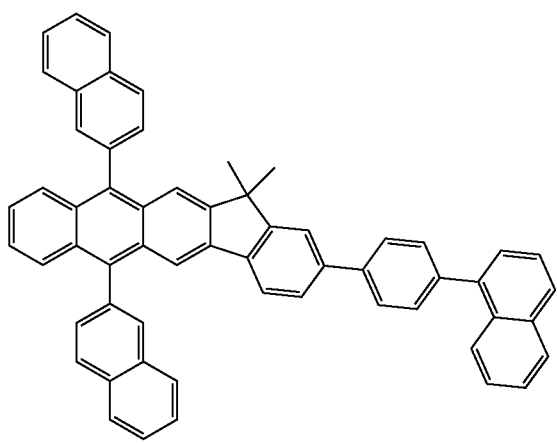
In an implementation, the host may include at least one selected from Compounds H43 to H49 below, but is not limited thereto.
H43
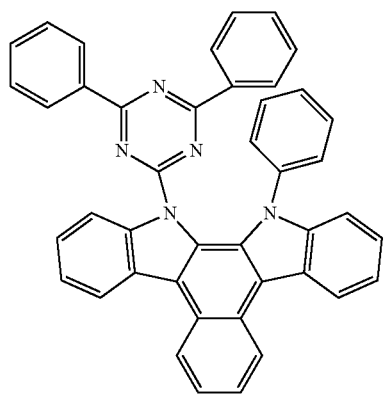
H44
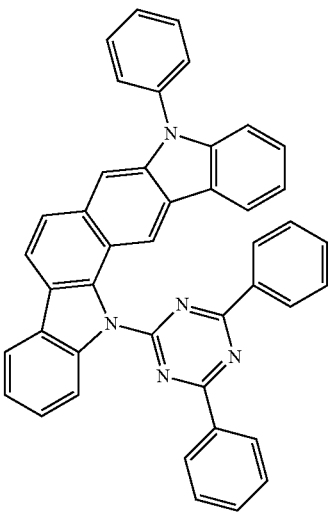
H45
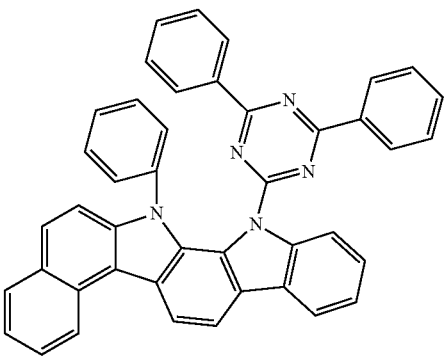
H46
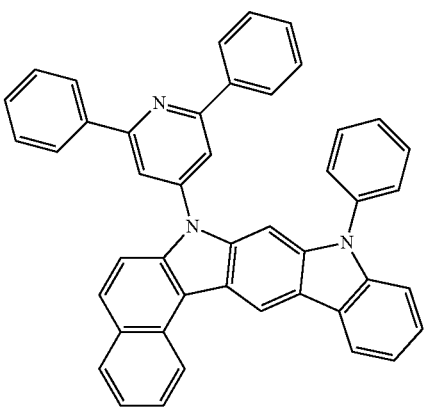

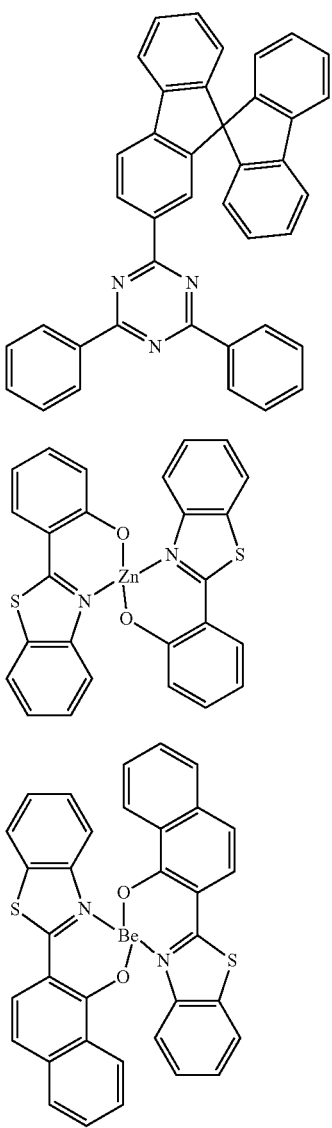

H47

H48

H49

The dopant may further include at least one of a fluorescent dopant and a phosphorescent dopant.

The phosphorescent dopant may include an organic metal, e.g., organometallic, complex represented by Formula 401 below:

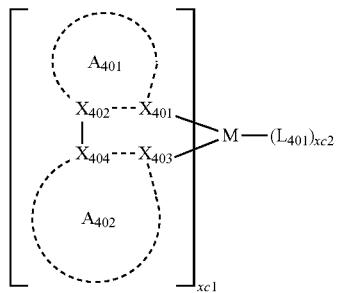

<Formula 401> in Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently selected from nitrogen or carbon;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrol, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted, pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, substituted naphthalene, substituted fluorene, substituted spiro-fluorene, substituted indene, substituted pyrrol, substituted thiophene, substituted furan, substituted imidazole, substituted pyrazole, substituted thiazole, substituted isothiazole, substituted oxazole, substituted isooxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzooxazole, substituted isobenzooxazole, substituted triazole, substituted oxadiazole, substituted triazine, substituted dibenzofuran and substituted dibenzothiophene may be selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl, a $C_2$-$C_{60}$ alkenyl, a $C_2$-$C_{60}$ alkynyl, and a $C_1$-$C_{60}$ alkoxy;

a $C_1$-$C_{60}$ alkyl, a $C_2$-$C_{60}$ alkenyl, a $C_2$-$C_{60}$alkynyl and a $C_1$-$C_{60}$ alkoxy, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$cycloalkyl, a $C_3$-$C_{10}$ heterocycloalkyl, a $C_3$-$C_{10}$cycloalkenyl, a $C_3$-$C_{10}$ heterocycloalkenyl, a $C_6$-$C_{60}$aryl, a $C_6$-$C_{60}$ aryloxy, a $C_6$-$C_{60}$ arylthio, a $C_2$-$C_{60}$ heteroaryl, non-aromatic condensed polycyclic group (non-aromatic condensed polycyclic group), —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, a monovalent non-aromatic condensed polycyclic group, and a monovalent non-aromatic hetero condensed polycyclic group;

a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, monovalent non-aromatic condensed polycyclic group and monovalent non-aromatic hetero condensed polycyclic group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryloxy, a $C_6$-$C_{60}$ arylthio, a $C_2$-$C_{60}$ heteroaryl, a monovalent non-aromatic condensed polycyclic group, a monovalent non-aromatic hetero condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$) and —B($Q_{426}$)($Q_{427}$);

$L_{401}$ is an organic ligand;

xc1 is 1, 2, or 3; and xc2 is 0, 1, 2, or 3.

$L_{401}$ may be any of a monovalent, a divalent, or a trivalent organic ligand. For example, $L_{401}$ may be selected from a halogen ligand (for example, Cl and F), a diketone ligand (for example, acetylacetonate, 1,3-diphenyl-1,3-propanedionate, 2,2,6,6-tetramethyl-3,5-heptanedionate, and hexafluoroacetonate), a carboxylic acid ligand (for example, picolinate, dimethyl-3-pyrazolecarboxylate, and benzoate), a carbon monoxide ligand, an isonitrile ligand, a cyano ligand, and a phosphorous ligand (for example, phosphine), phosphaite, but it is not limited thereto.

In Formula 401, when $A_{401}$ has two or more substituents, the two or more substituents of $A_{401}$ may be bound to each other to form a saturated ring or an unsaturated ring.

In Formula 401, when $A_{402}$ has two or more substituents, the two or more substituents of $A_{402}$ may be bound to each other to form a saturated ring or an unsaturated ring.

In Formula 401, when xc1 is two or greater, a plurality of ligands in Formula 401

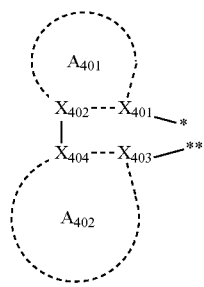

may be the same as or different from each other. In Formula 401, when xc1 is two or greater, each of $A_{401}$ and $A_{402}$ may be connected to each of $A_{401}$ and $A_{402}$ of a neighboring ligand either directly or via a linking group (for example, a $C_1$-$C_5$ alkylene and —N(R')— (wherein, R' is a $C_1$-$C_{10}$ alkyl group or a $C_6$-$C_{20}$ aryl group), or —C(=O)—).

The phosphorescent dopant may include at least one of Compounds PD1 to PD74, but it is not limited thereto.

PD1

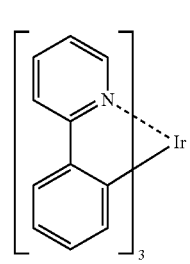

PD2

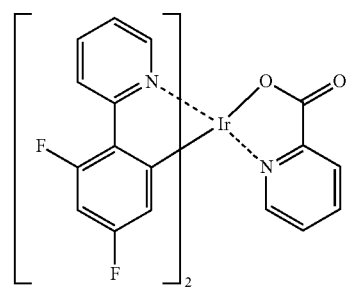

PD3

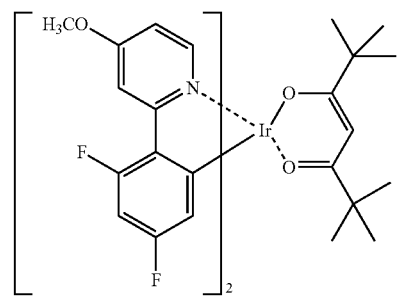

PD4

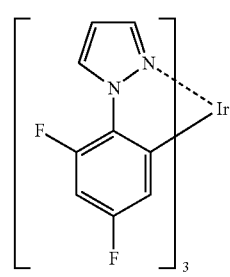

PD5

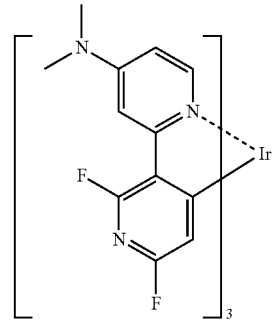

PD6
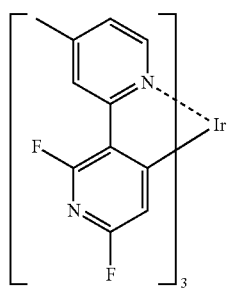
PD7
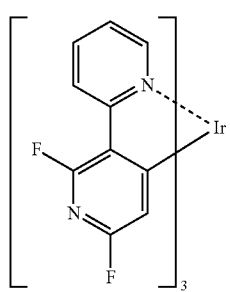
PD8
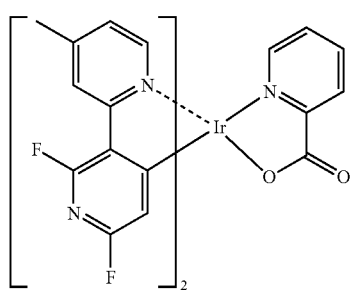
PD9
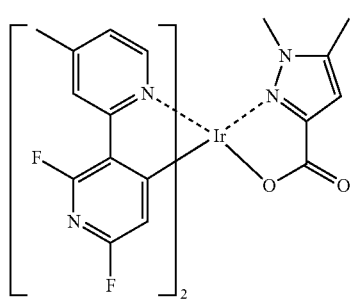
PD10
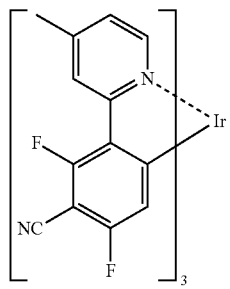
PD11
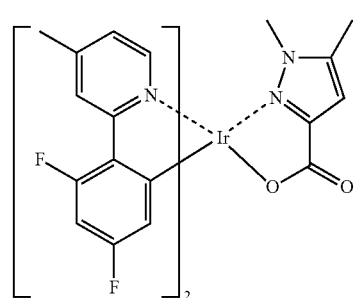
PD12
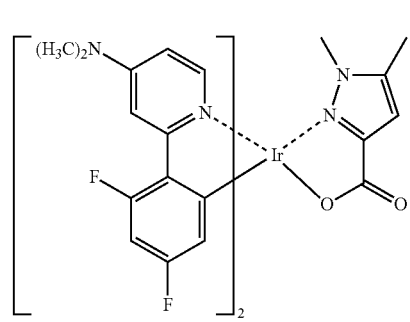
PD13
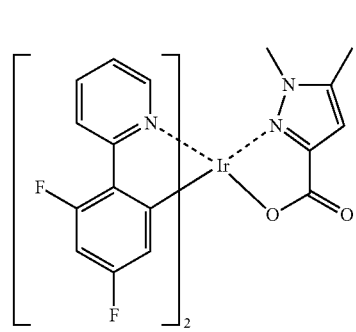
PD14
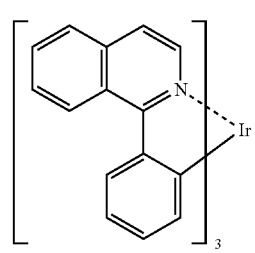
PD15
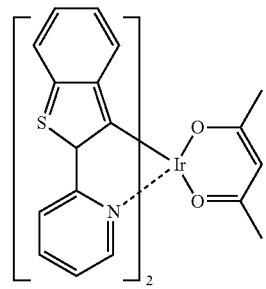

-continued
PD16
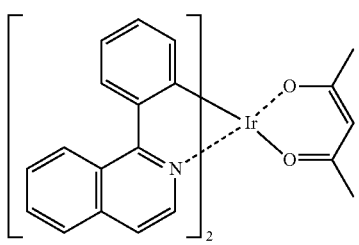
PD17
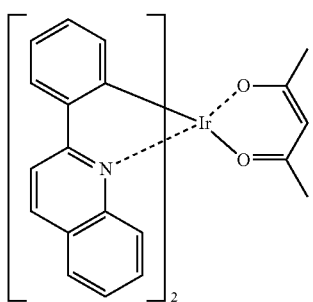
PD18
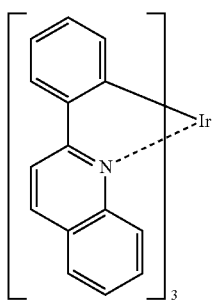
PD19
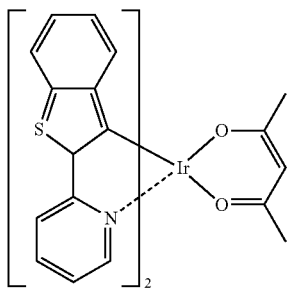
PD20
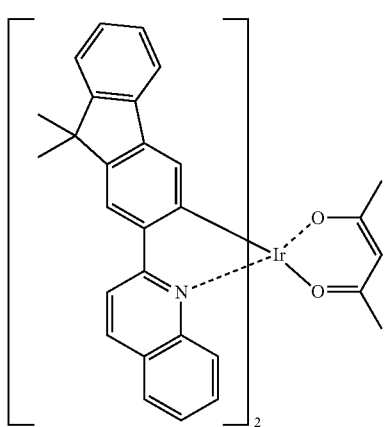
-continued
PD21
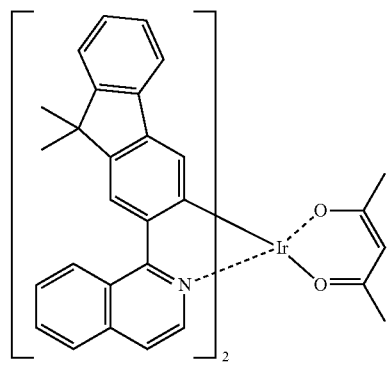
PD22
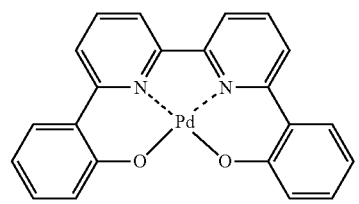
PD23
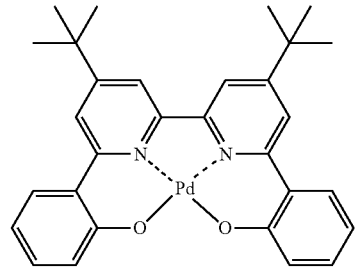
PD24
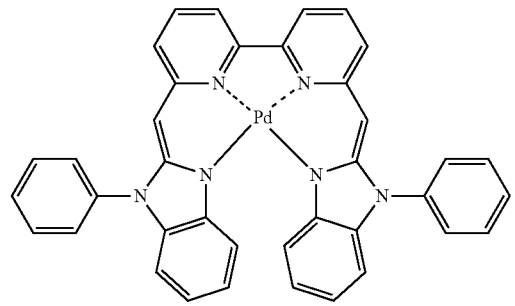
PD25
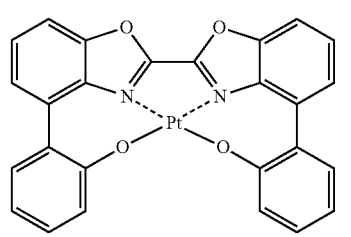
PD26
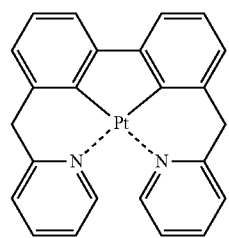

PD27 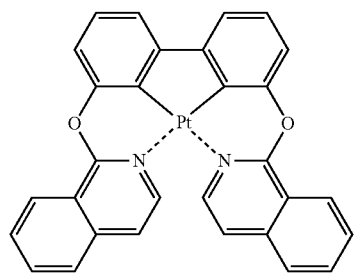
PD28 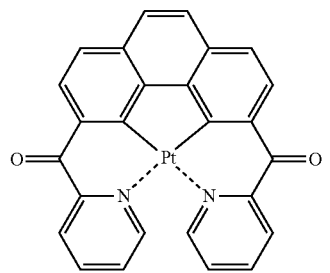
PD29 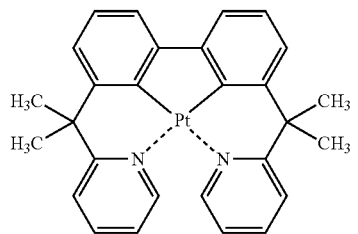
PD30 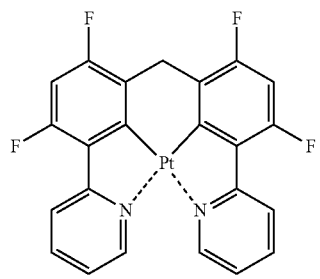
PD31 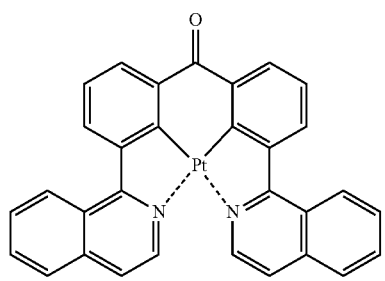
PD32 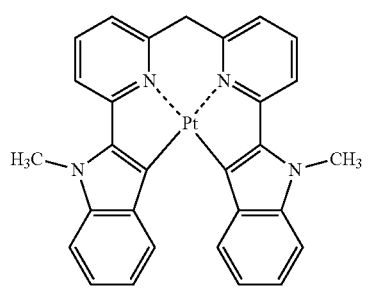
PD33 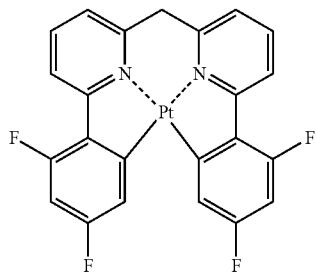
PD34 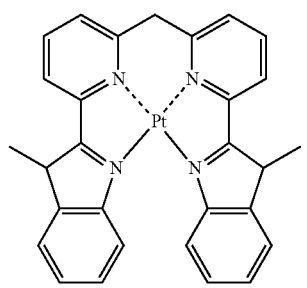
PD35 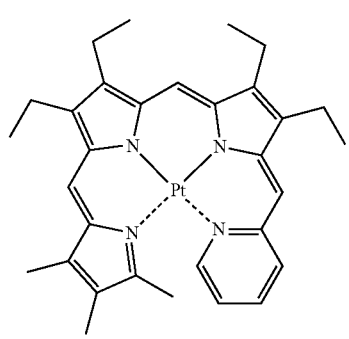
PD36 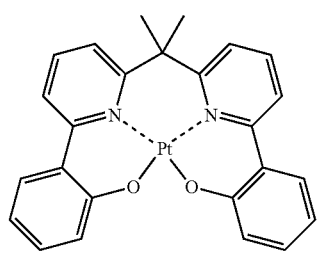
PD37 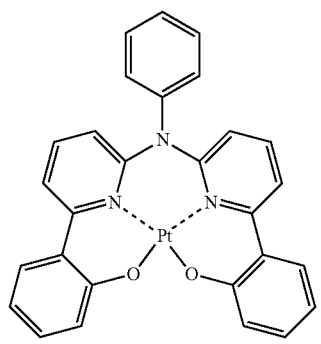

-continued
PD38
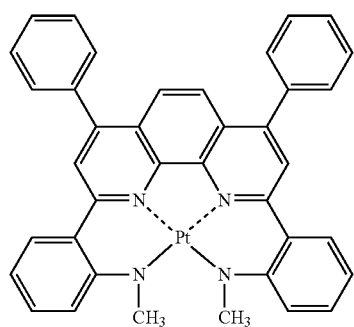
PD43
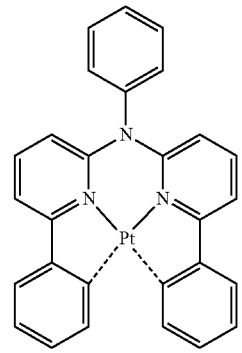
PD39
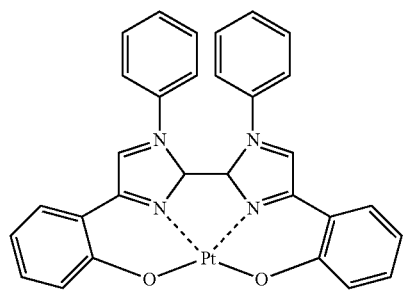
PD44
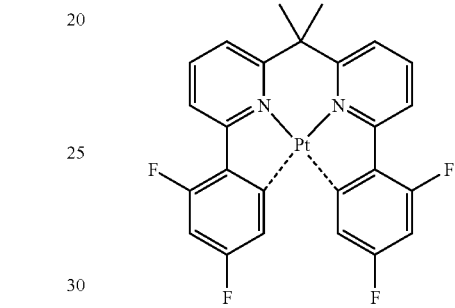
PD40
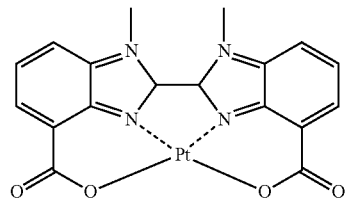
PD45
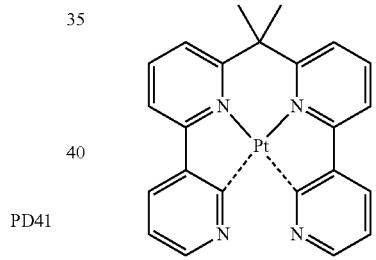
PD41
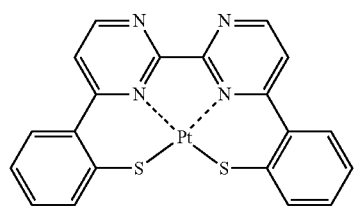
PD46
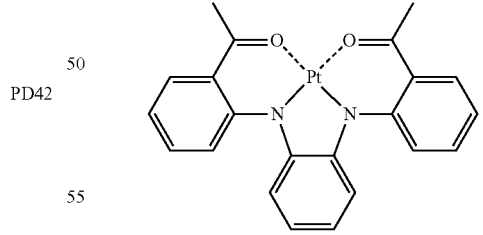
PD42
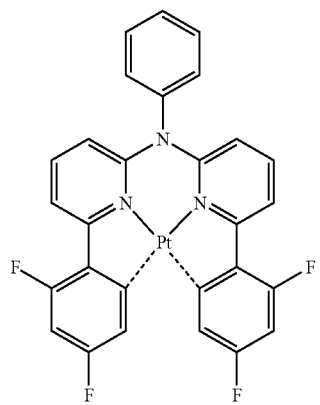
PD47

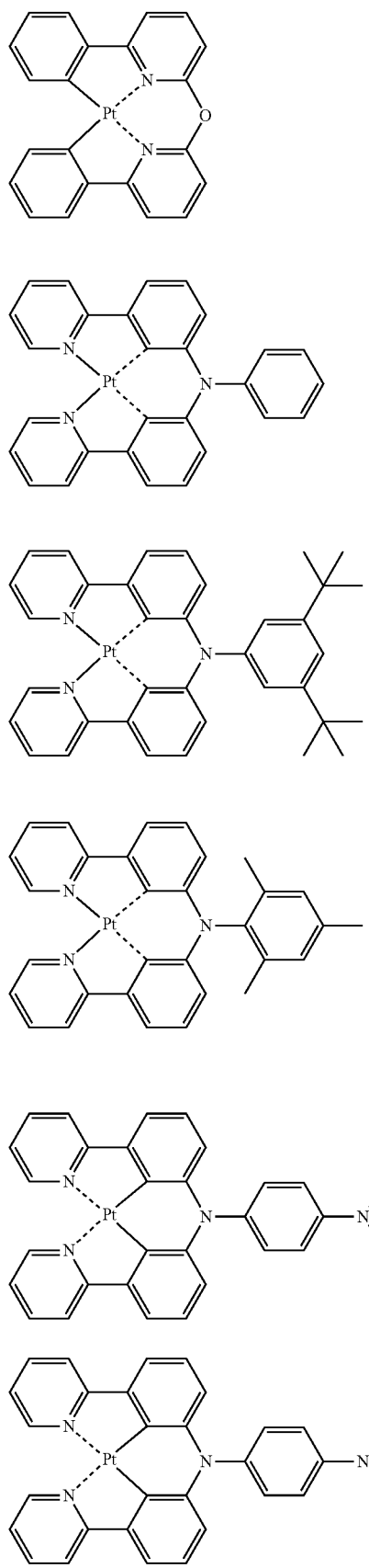
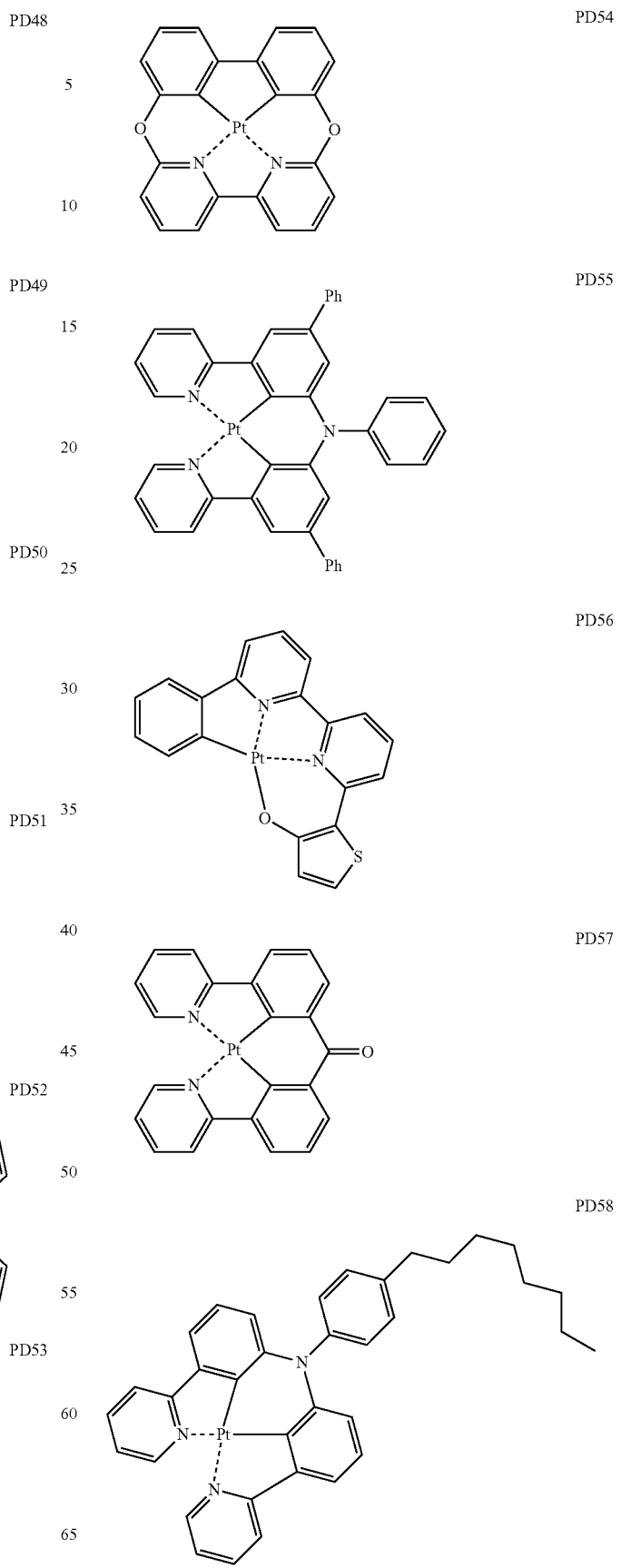

PD59 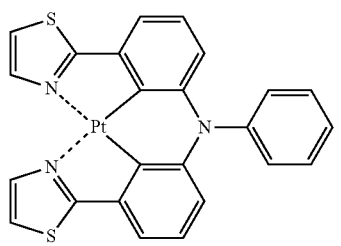
PD60 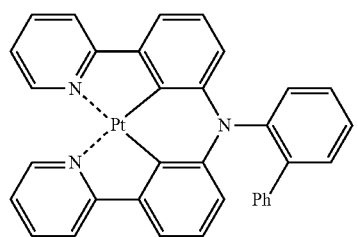
PD61 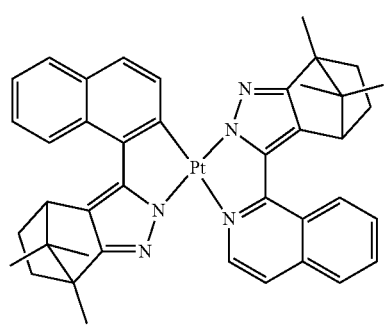
PD62 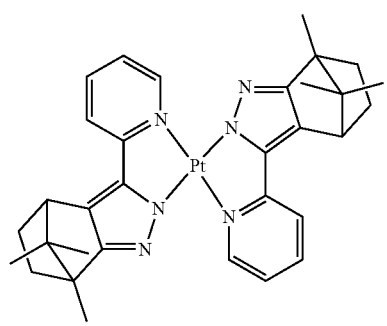
PD63 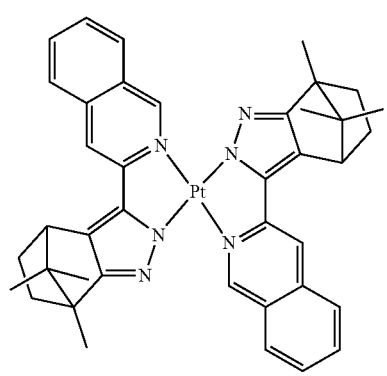
PD64 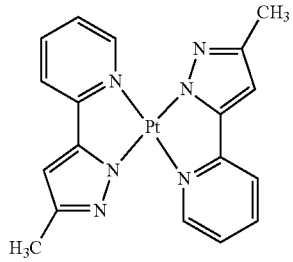
PD65 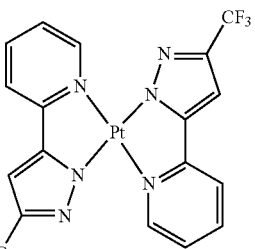
PD66 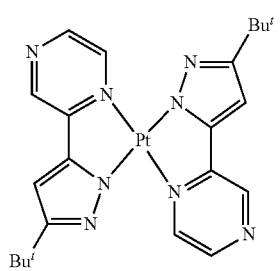
PD67 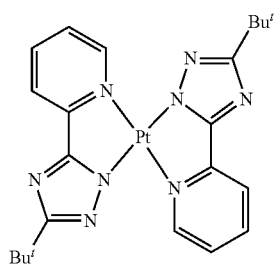
PD68 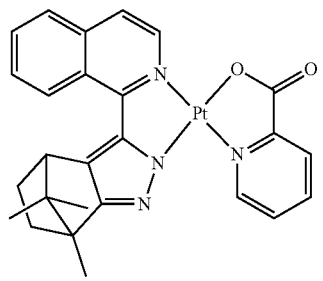

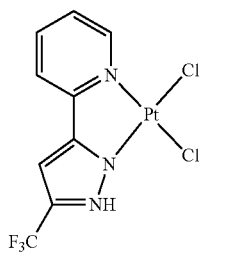
PD69
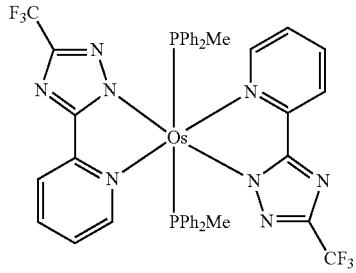
PD73
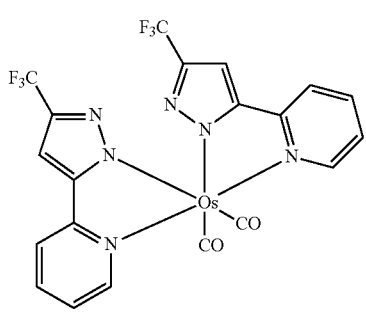
PD70
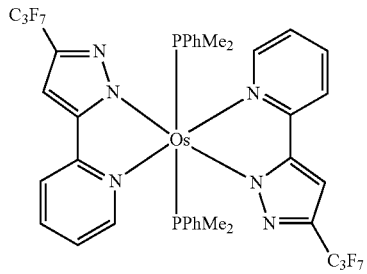
PD74
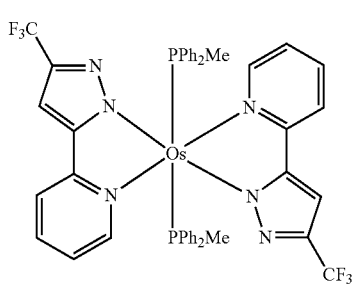
PD71
In an implementation, the phosphorescent dopant may include PtOEP below:
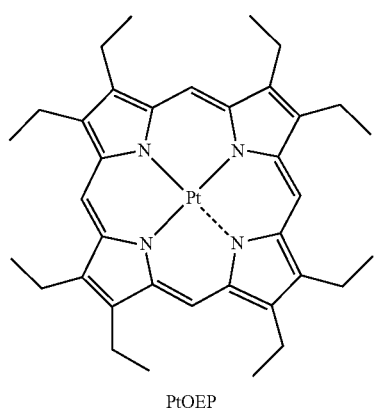
PtOEP
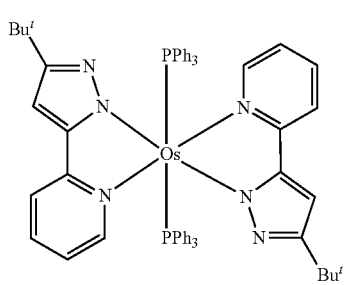
PD72
The fluorescent dopant may include at least one selected from DPAVBi, BDAVBi, TBPe, DCM, DCJTB, Coumarin 6, and C545T.

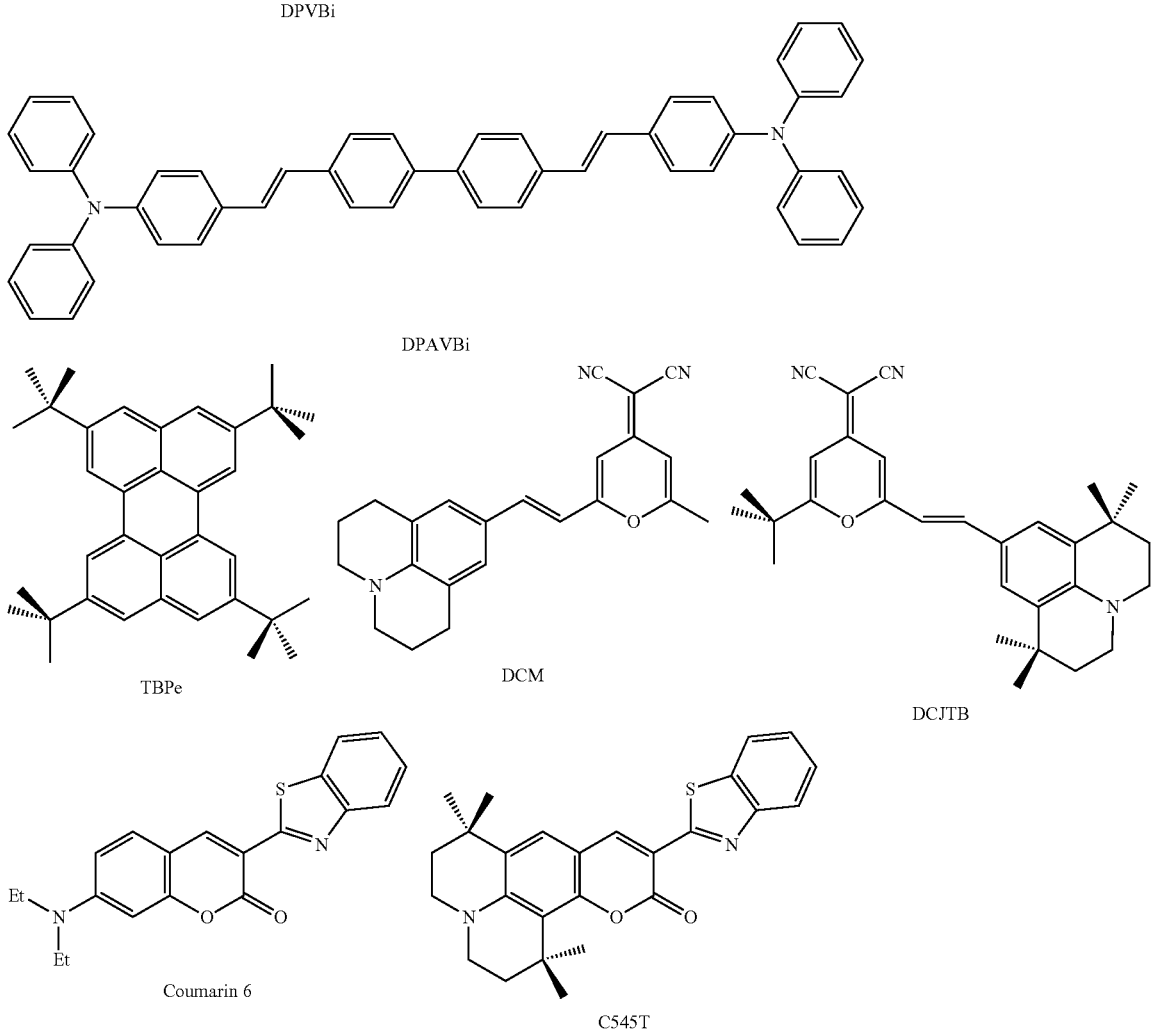

In an implementation, the fluorescent dopant may include a compound represented by Formula 501 below:

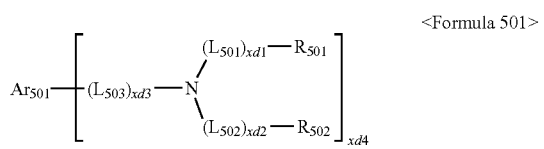

<Formula 501> in Formula 501,

Ar$_{501}$ may be selected from naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene;

naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene and indenoanthracene, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$cycloalkyl, a $C_3$-$C_{10}$ heterocycloalkyl, a $C_3$-$C_{10}$cycloalkenyl, a $C_3$-$C_{10}$ heterocycloalkenyl, a $C_6$-$C_{60}$aryl, a $C_6$-$C_{60}$ aryloxy, a $C_6$-$C_{60}$ arylthio, a $C_2$-$C_{60}$ heteroaryl, a monovalent non-aromatic condensed polycyclic group, a monovalent non-aromatic condensed heteropolycyclic group, and —Si($Q_{501}$)($Q_{502}$)($Q_{503}$) (wherein, $Q_{501}$ to $Q_{503}$ may be each independently selected from hydrogen, a $C_1$-$C_{60}$ alkyl, a $C_2$-$C_{60}$ alkenyl, a $C_6$-$C_{60}$ aryl and a $C_2$-$C_{60}$ heteroaryl);

descriptions of $L_{501}$ to $L_{503}$ may be understood by referring to the description of $L_{201}$ herein;

$R_{501}$ and $R_{502}$ may be each independently selected from phenyl, naphthyl, fluorenyl, spiro-fluorenyl, benzofluorenyl, dibenzofluorenyl, phenanthrenyl, anthracenyl, pyrenyl, chrysenyl, pyridinyl, pyrazinyl, pyrimidinyl, pyridazinyl, quinolinyl, isoquinolinyl, quinoxalinyl, quinazolinyl, carbazole, triazinyl, dibenzofuranyland dibenzthiophenyl; and phenyl, naphthyl, fluorenyl, spiro-fluorenyl, benzofluorenyl, dibenzofluorenyl, phenanthrenyl, anthracenyl, pyrenyl, chrysenyl, pyridinyl, pyrazinyl, pyrimidinyl, pyridazinyl, quinolinyl, isoquinolinyl, quinoxalinyl, quinazolinyl, carbazolyl, triazinyl and dibenzofuranyland dibenzothiophenyl, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl, a $C_1$-$C_{20}$ alkoxy, phenyl, naphthyl, fluorenyl, spiro-fluorenyl, benzofluorenyl, dibenzofluorenyl, phenanthrenyl, anthracenyl, pyrenyl, chrysenyl, pyridinyl, pyrazinyl, pyrimidinyl, pyridazinyl, quinolinyl, isoquinolinyl, quinoxalinyl, quinazolinyl, carbazolyl, triazinyl, dibenzofuranyl, and dibenzothiophenyl;

xd1 to xd3 may be each independently selected from 0, 1, 2, and 3; and xb4 may be selected from 1, 2, 3, and 4.

The fluorescent dopant may include at least one selected from Compounds FD1 to FD8:

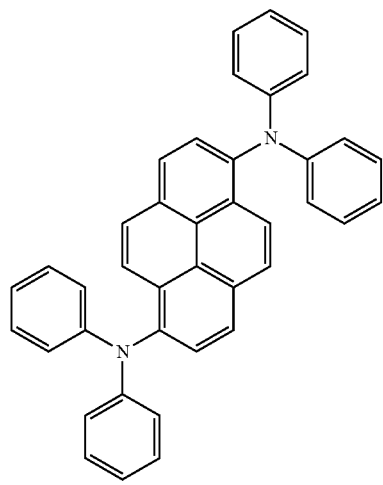

FD1

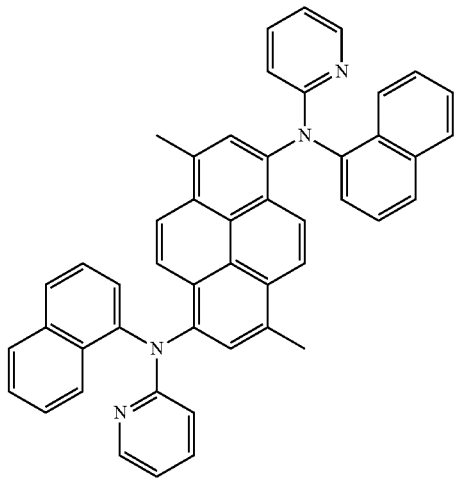

FD2

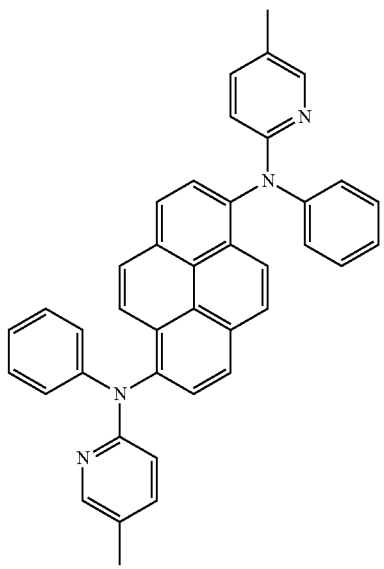

FD3

-continued

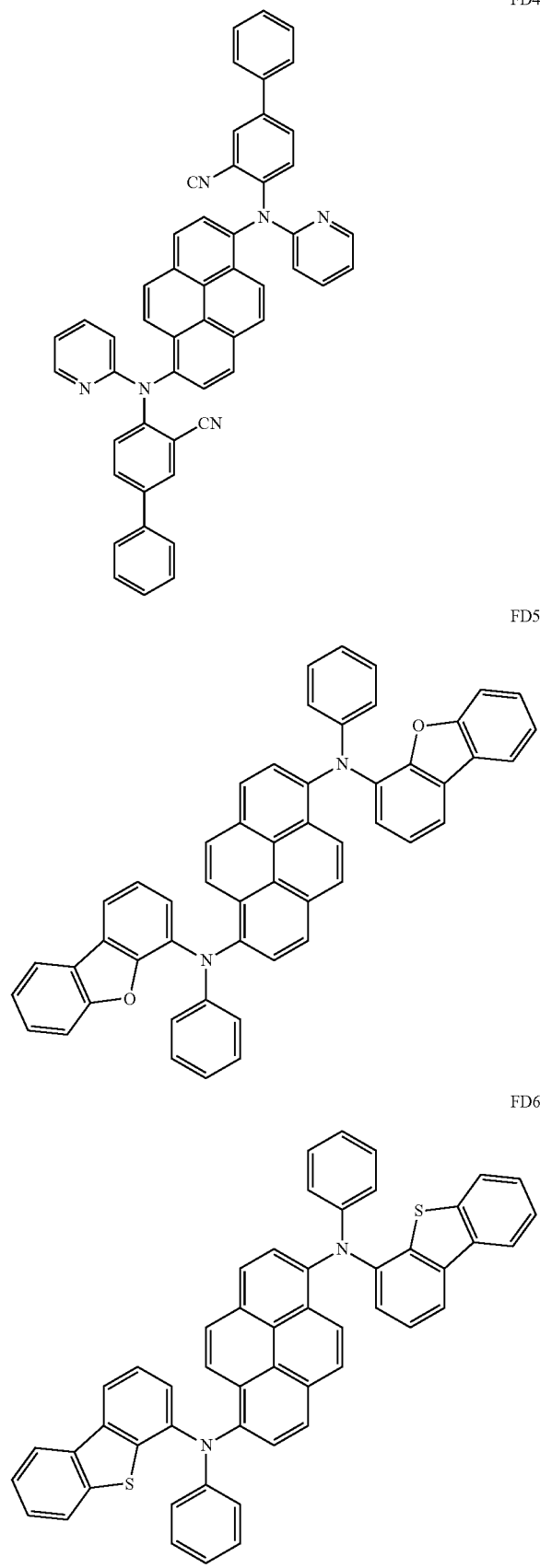

FD4

FD5

FD6

-continued

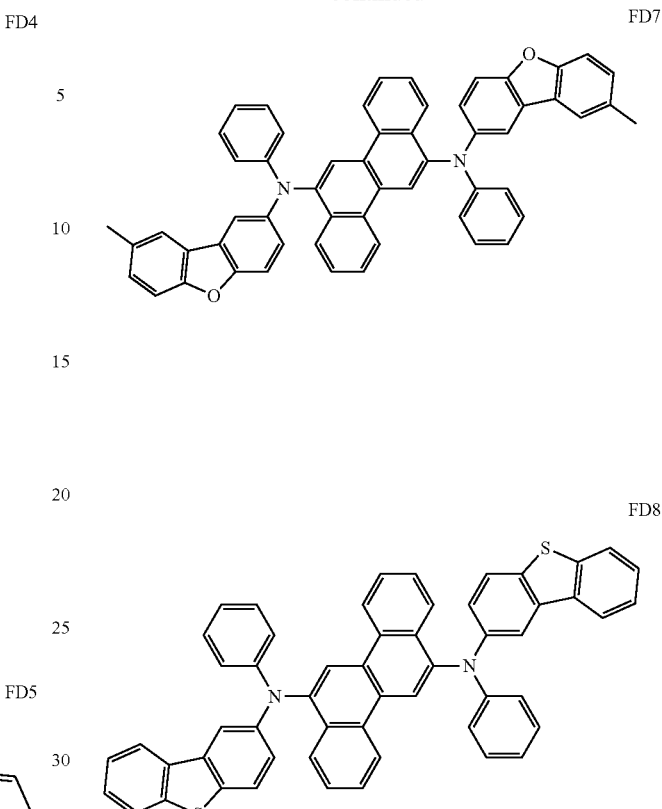

FD7

FD8

In the EML, an amount of the dopant may be about 0.01 parts by weight to about 15 parts by weight based on 100 parts by weight of the host, but it is not limited thereto.

A thickness of the EML may be about 100 Å to about 1000 Å, for example, about 200 Å to about 600 Å. When the thickness of the EML is in the range described above, the EML may have excellent light-emitting ability without a substantial increase in driving voltage.

The electron transport region may be disposed on the EML.

The electron transport region may include at least one of the HBL, the ETL, and EIL, but it is not limited thereto.

For example, the electron transport region may have a structure in which the ETL, the ETL/EIL or HBL/ETL/EIL is sequentially layered on the EML, but it is not limited thereto.

The electron transport region may include an HBL. When the EML includes a phosphorescent dopant, the HBL may be formed to prevent diffusion of triplet excitons or holes into the ETL.

When the electron transport region includes the HBL, the HBL may be formed on the EML by using various methods such as vacuum deposition, spin coating, casting, LB, inkjet printing, laser printing, and LITI. When the HBL is formed by vacuum deposition and spin coating, the deposition and coating conditions may be similar to those for forming the HIL, though the deposition and coating conditions may vary according to a compound that is used to form the HBL.

The HBL may include at least one of BCP and Bphen, but it is not limited thereto.

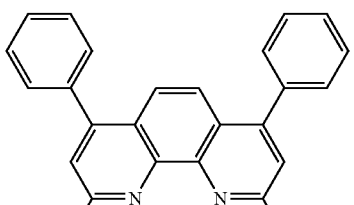

BCP

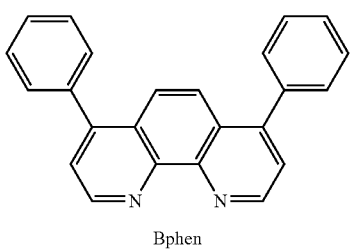

Bphen

A thickness of the HBL may be from about 20 Å to about 1,000 Å, and in some embodiments, may be from about 30 Å to about 300 Å. When the thickness of the HBL is within these ranges, the HBL may have a hole blocking transporting ability without a substantial increase in driving voltage.

The electron transport region may include an ETL. The ETL may be formed on the EML or the HBL by using various methods such as vacuum deposition, spin coating, casting, LB, inkjet printing, laser printing, and LITI. When the ETL is formed by vacuum deposition and spin coating, the deposition and coating conditions may be similar to those for forming the HIL, though the deposition and coating conditions may vary according to a compound that is used to form the ETL.

The ETL may include the condensed cyclic compound represented by Formula 1 above.

The ETL may include at least ne of BCP, Bphen above the Alq$_3$, Balq, TAZ and NTAZ below, in addition to the condensed cyclic compound represented by Formula 1 above.

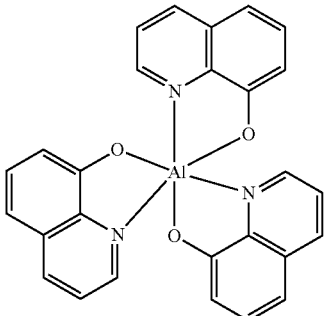

Alq$_3$

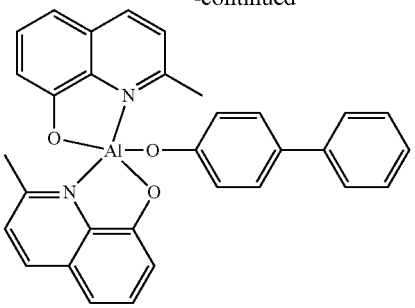

BAlq

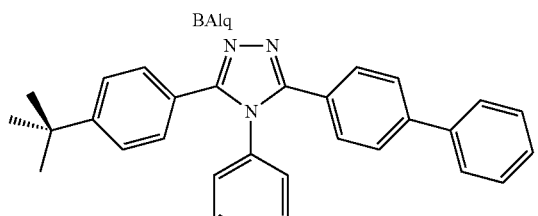

TAZ

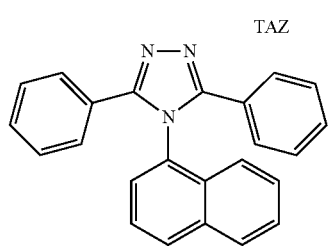

NTAZ

In an implementation, the ETL may include the condensed cyclic compound represented by Formula 1 above along with a compound represented by Formula 601 below:

$Ar_{601}\text{-}[L_{601}]_{xe1}\text{-}E_{601}]_{xe2}$ <Formula 601> in Formula 601, $Ar_{601}$ may be selected from naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene; and naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene and indenoanthracene, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, $C_1$-$C_{60}$ alkyl, $C_2$-$C_{60}$ alkenyl, $C_2$-$C_{60}$ alkynyl, $C_1$-$C_{60}$ alkoxy, $C_3$-$C_{10}$ cycloalkyl, $C_3$-$C_{10}$ heterocycloalkyl, $C_3$-$C_{10}$ cycloalkenyl, $C_3$-$C_{10}$ heterocycloalkenyl, $C_6$-$C_{60}$ aryl, $C_6$-$C_{60}$ aryloxy, $C_6$-$C_{60}$ arylthio, $C_2$-$C_{60}$ heteroaryl, a monovalent non-aromatic condensed polycyclic group, a monovalent non-aromatic condensed hetero-polycyclic group, and —Si($Q_{301}$)($Q_{302}$)($Q_{303}$) (wherein, $Q_{301}$ to $Q_{303}$ may be each independently, hydrogen, $C_1$-$C_{60}$ alkyl, $C_2$-$C_{60}$ alkenyl, $C_6$-$C_{60}$ aryl, and $C_2$-$C_{60}$ heteroaryl);

description of $L_{601}$ may be understood by referring to the description of $L_{201}$;

$E_{601}$ may be selected from pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl; and pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl and dibenzocarbazolyl, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, $C_1$-$C_{20}$ alkyl, $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl;

xe1 may be selected from 0, 1, 2, and 3; and xe2 may be selected from 1, 2, 3, and 4.

In an implementation, the ETL may include at least one of the compounds represented by Formula 602:

<Formula 602>

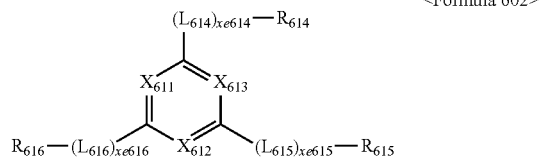

in Formula 602, $X_{611}$ may be selected from N or C-$(L_{611})_{xe611}$-$R_{611}$, $X_{612}$ may be selected from N or C-$(L_{612})_{xe612}$-$R_{612}$, $X_{613}$ may be selected from N or C-$(L_{613})_{xe613}$-$R_{613}$, and at least one of $X_{611}$ to $X_{613}$ may be N;

description for each of $L_{611}$ to $L_{616}$ may be understood by referring to the description of $L_{201}$ herein;

$R_{611}$ to $R_{616}$ may be each independently selected from phenyl, naphthyl, fluorenyl, spiro-fluorenyl, benzofluorenyl, dibenzofluorenyl, phenanthrenyl, anthracenyl, pyrenyl, chrysenyl, pyridinyl, pyrazinyl, pyrimidinyl, pyridazinyl, quinolinyl, isoquinolinyl, quinoxalinyl, quinazolinyl, carbazolyl, and triazinyl; and phenyl, naphthyl, fluorenyl, spiro-fluorenyl, benzofluorenyl, dibenzofluorenyl, phenanthrenyl, anthracenyl, pyrenyl, chrysenyl, pyridinyl, pyrazinyl, pyrimidinyl, pyridazinyl, quinolinyl, isoquinolinyl, quinoxalinyl, quinazolinyl, carbazolyl and triazinyl, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl, a $C_1$-$C_{20}$ alkoxy, phenyl, naphthyl, azulenyl, fluorenyl, spiro-fluorenyl, benzofluorenyl, dibenzofluorenyl, phenanthrenyl, anthracenyl, pyrenyl, chrysenyl, pyridinyl, pyrazinyl, pyrimidinyl, pyridazinyl, quinolinyl, isoquinolinyl, quinoxalinyl, quinazolinyl, carbazolyl, and triazinyl; and xe611 to xe616 may be each independently selected from 0, 1, 2, and 3.

The compound represented by Formula 601 and the compound represented by Formula 602 above may include at least one from Compounds ET1 to ET15 below.

ET1

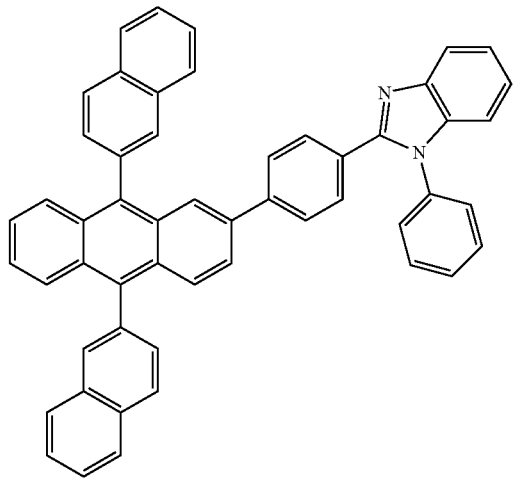

117
-continued
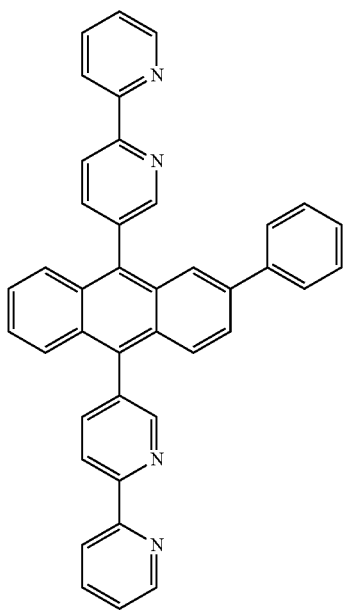
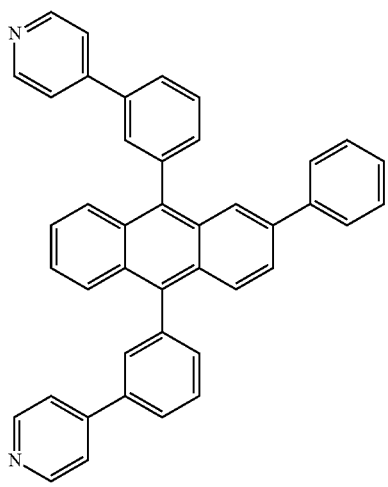
ET3
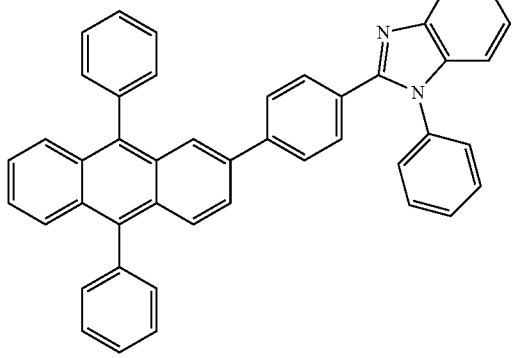
ET4
118
-continued
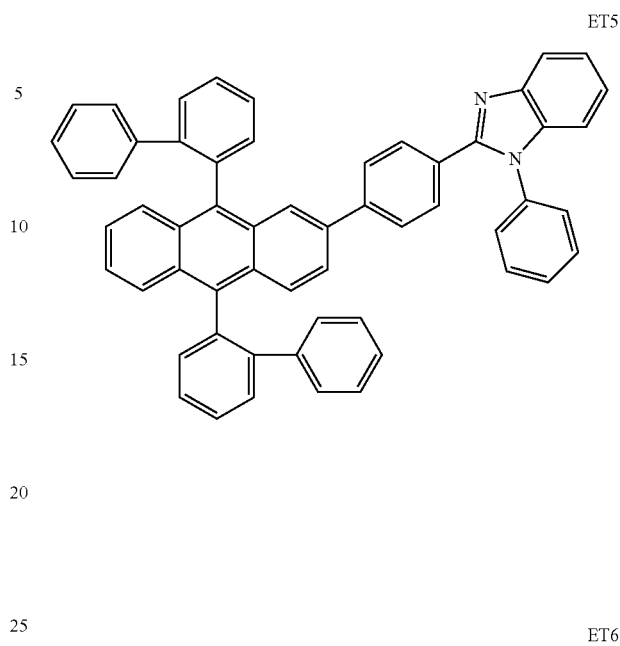
ET2
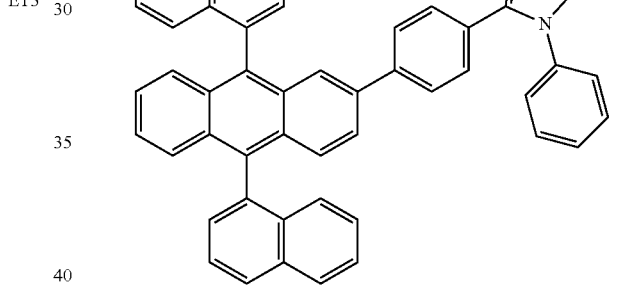
ET5
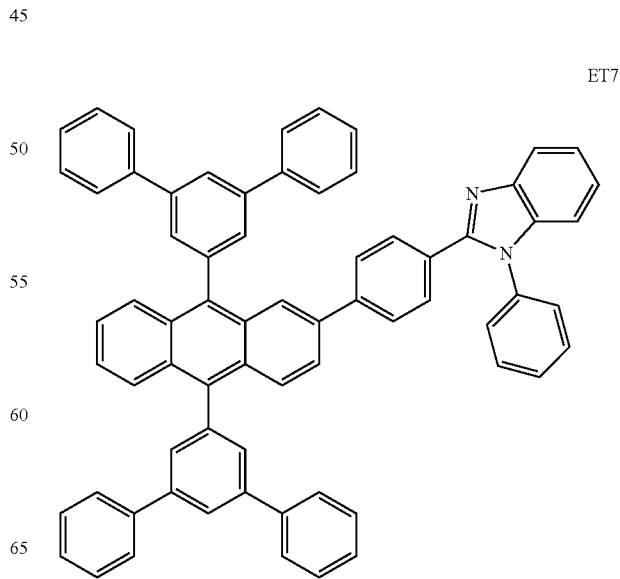
ET6
ET7

ET8
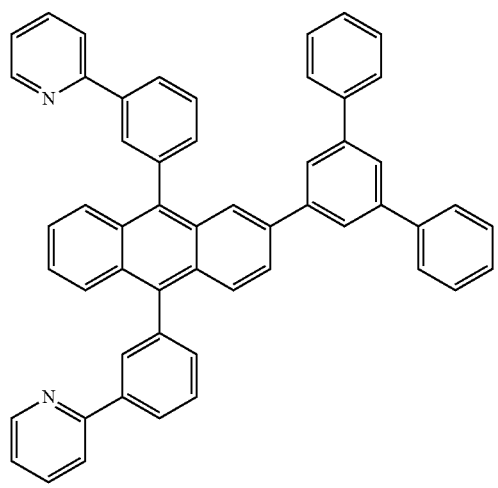
ET9
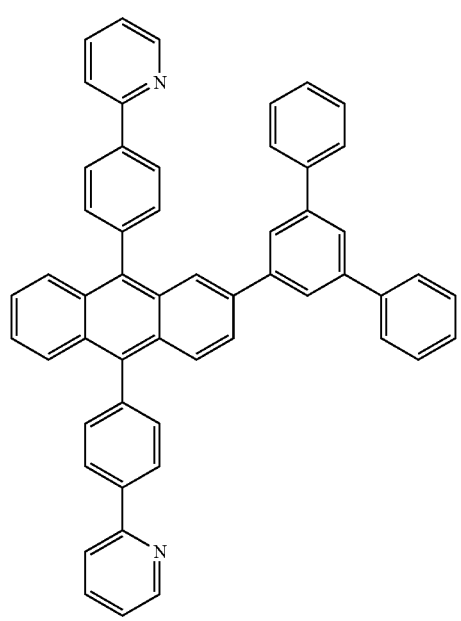
ET10
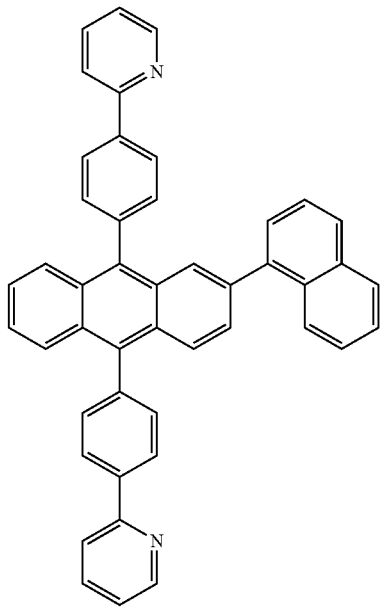
ET11
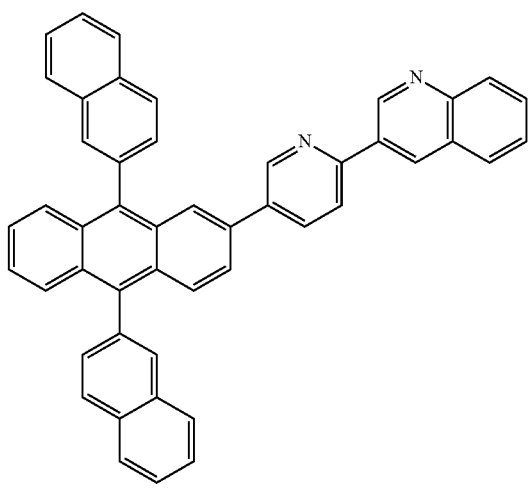
ET12
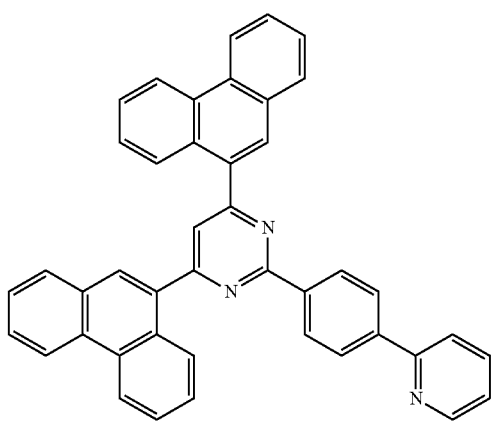

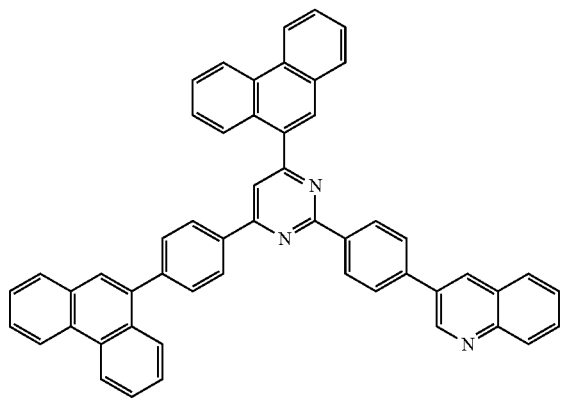

ET13

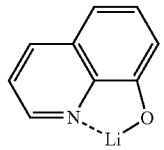

ET-D1

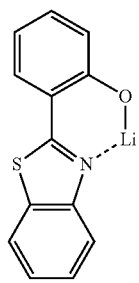

ET-D2

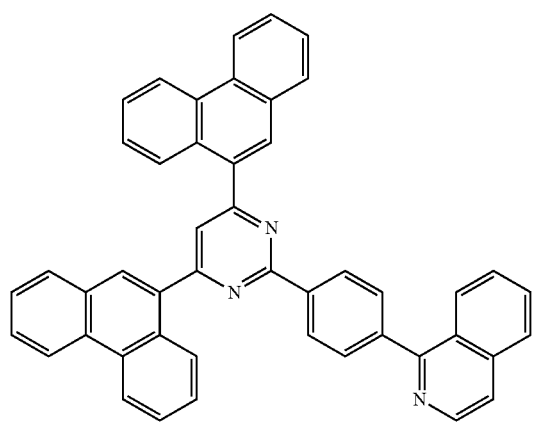

ET14

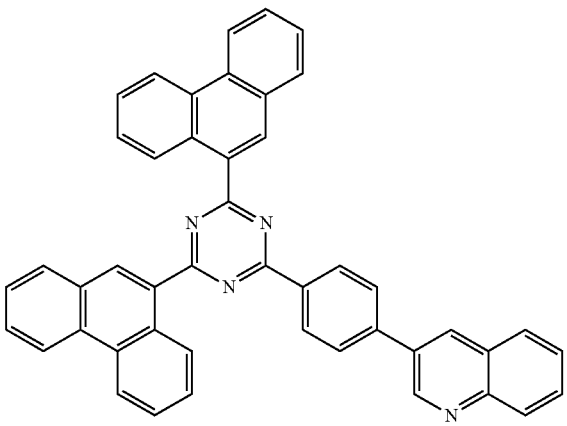

ET15

A thickness of the ETL may be about 100 Å to about 1,000 Å, for example, about 150 Å to about 500 Å. When the thickness of the ETL is within the range described above, the ETL may have satisfactory electron transport characteristics without a substantial increase in driving voltage.

The ETL may further include a metal-containing material in addition to the material described above.

The metal-containing material may include a Li complex. The Li complex may, for example, include compounds ET-D1 (lithium quinolate: LiQ) or ET-D2 illustrated below.

The electron transport region may include and EIL that facilitates electron injection from the second electrode 190.

The EIL may be formed on the ETL by using various methods such as vacuum deposition, spin coating, casting, LB, inkjet printing, laser printing, and LITI. When the EIL is formed by vacuum deposition or spin coating, the deposition and coating conditions may be similar to those for forming the HIL. When the EIL is formed using a vacuum deposition or spin coating, the deposition and coating conditions may be similar to those for the formation of the HIL.

The EIL may include at least one selected from LiF, NaCl, CsF, $Li_2O$, BaO, and LiQ.

A thickness of the EIL may be about 1 Å to about 100 Å or about 3 Å to about 90 Å. When the thickness of the EIL is within the range described above, satisfactory electron injection characteristics may be obtained without a substantial increase in driving voltage.

The second electrode 190 is disposed on the organic layer 150 described above. The second electrode 190 may be a cathode, which is an electron injection electrode, in which a material of the second electrode 190 may be a metal, an alloy, an electroconductive compound, or a mixture thereof having a low work function. Detailed examples of the material of the second electrode 190 include lithium (Li), magnesium (Mg), aluminum (Al), aluminum-lithium (Al—Li), calcium (Ca), magnesium-indium (Mg—In), and magnesium-silver (Mg—Ag). In an implementation ITO, IZO, or the like may be used as the material of the second electrode 190. The second electrode 190 may be a reflective electrode, a semi-transmission electrode, or a transmission electrode.

Hereinabove, the organic light-emitting device is described with reference to the FIGURE, but it is not limited thereto.

As used herein, the $C_1$-$C_{60}$ alkyl group refers to a linear or branched aliphatic $C_1$-$C_{60}$ hydrocarbon monovalent group and detailed examples thereof include a methyl group, an ethyl group, a propyl group, an isobutyl group, a sec-butyl group, a tert-butyl group, a pentyl group, an iso-amyl group, and a hexyl group. As used herein, the $C_1$-$C_{60}$ alkylene group refers to a divalent group having the same structure as the $C_1$-$C_{60}$ alkyl group.

As used herein, the $C_1$-$C_{60}$ alkoxy group is a monovalent group having a formula of —$OA_{101}$ (wherein, $A_{101}$ is the $C_1$-$C_{60}$ alkyl group) and detailed examples thereof include a methoxy group, an ethoxy group, and an isopropyloxy group.

As used herein, the $C_2$-$C_{60}$ alkenyl group refers to a $C_2$-$C_{60}$ alkyl group having one or more carbon-carbon double bonds at a center or end thereof. Examples of the unsubstituted $C_2$-$C_{60}$ alkenyl group are en ethenyl group, a propenyl group, and a butenyl group. As used herein, the $C_2$-$C_{60}$ alkenylene group refers to a divalent group having the same structure as the $C_2$-$C_{60}$ alkenyl group.

As used herein, the $C_2$-$C_{60}$ alkynyl group refers to an unsubstituted $C_2$-$C_{60}$ alkyl group having one or more carbon-carbon triple bonds at a center or end thereof. Examples of the $C_2$-$C_{60}$ alkynyl group are an ethynyl group, a propynyl group, and the like. As used herein, the $C_2$-$C_{60}$ alkynylene group refers to a divalent group having the same structure as the $C_2$-$C_{60}$ alkynyl group.

As used herein, the $C_3$-$C_{10}$ cycloalkyl group refers to a $C_3$-$C_{10}$ monovalent hydrocarbon monocyclic group and detailed examples thereof include a cyclopropyl group, a cyclobutyl group, a cyclopentyl group, a cyclohexyl group, and a cycloheptyl group. As used herein, the $C_3$-$C_{10}$ cycloalkylene group refers to a divalent group having the same structure as the $C_3$-$C_{10}$ cycloalkyl group.

As used herein, the $C_2$-$C_{10}$ heterocycloalkyl group refers to a $C_2$-$C_{10}$ monovalent monocyclic group including at least one selected from N, O, P, and S as a ring-forming atom and detailed examples thereof include a tetrahydrofuranyl group and a tetrahydrothiophenyl group. As used herein, the $C_2$-$C_{10}$ heterocycloalkylene group refers to a divalent group having the same structure as the $C_2$-$C_{10}$ heterocycloalkyl group.

As used herein, the $C_3$-$C_{10}$ cycloalkenyl group refers to a $C_3$-$C_{10}$ monovalent monocyclic group having at least one double bond in a ring but without aromaticity, and detailed examples thereof include a cyclopentenyl group, a cyclohexenyl group, and a cycloheptenyl group. As used herein, the $C_3$-$C_{10}$ cycloalkenylene group refers to a divalent group having the same structure as the $C_3$-$C_{10}$ cycloalkenyl group.

As used herein, the $C_2$-$C_{10}$ heterocycloalkenyl group is a $C_2$-$C_{10}$ monovalent monocyclic group including at least one selected from N, O, P, and S as a ring-forming atom, and includes at least one double bond in a ring. Detailed examples of the $C_2$-$C_{10}$ heterocycloalkenyl group include a 2,3-hydrofuranyl group and a 2,3-hydrothiophenyl group. As used herein, the $C_2$-$C_{10}$ heterocycloalkenylene group is a divalent group having the same structure as the $C_2$-$C_{10}$ heterocycloalkenyl group.

As used herein, the $C_6$-$C_{60}$ aryl group is a $C_6$-$C_{60}$ monovalent group having a carbocyclic aromatic system and the $C_6$-$C_{60}$ arylene group refers to a divalent group having a $C_6$-$C_{60}$ carbocyclic aromatic system. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include two or more rings, the two or more rings may be fused to each other.

As used herein, the $C_2$-$C_{60}$ heteroaryl group refers to a monovalent group having a $C_2$-$C_{60}$ carbocyclic aromatic system including at least one heteroatom selected from N, O, P, and S as a ring-forming atom and the $C_2$-$C_{60}$ heteroarylene group refers to a divalent group having a $C_2$-$C_{60}$ carbocyclic aromatic system including at least one heteroatom selected from N, O, P, and S. Examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ group include two or more rings, the two or more rings may be fused to each other.

As used herein, the $C_6$-$C_{60}$ aryloxy group refers to —$OA_{102}$ (wherein, $A_{102}$ is the $C_6$-$C_{60}$ aryl group) and the $C_6$-$C_{60}$ arythio group refers to —$SA_{103}$ (wherein, $A_{103}$ is the $C_6$-$C_{60}$ aryl group).

As used, herein, the monovalent non-aromatic condensed polycyclic group refers to a monovalent group having two or more rings that are fused to each other, including only carbon as a ring forming atom (for example, carbon number may be 8 to 60), wherein the entire molecule does not have aromaticity. Examples of the non-aromatic condensed polycyclic group include a fluorenyl group or the like. As used herein, the divalent non-aromatic condensed polycyclic group may refer to a divalent group having the same structure as the monovalent non-aromatic condensed polycyclic group.

As used herein, the monovalent non-aromatic hetero-condensed polycyclic group refers to a monovalent group having two or more rings that are fused to each other, including a heteroatom selected from N, O, P, and S as a ring-forming atom, in addition to carbon (for example, carbon number may be 2 to 60), wherein the entire molecule does not have aromaticity. The monovalent non-aromatic hetero-condensed polycyclic group includes a carbazolyl group or the like. As used herein, the divalent non-aromatic hetero-condensed polycyclic group refers to a divalent group having the same structure as the monovalent non-aromatic hetero-condensed polycyclic group.

As used herein, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arythio group, substituted $C_2$-$C_{60}$ heteroaryl group, substituted monovalent non-aromatic condensed polycyclic group and substituted monovalent non-aromatic condensed hetero-polycyclic group may be selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a cyclopentyl group, a cyclohexyl group, a cycloheptyl group, a cyclopentenyl group, a cycloheptenyl group, a phenyl group, a pentalenyl, group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl, group, a perylenyl group, pentaa phenyl group, a hexacenyl group, a pentacenyl group, a rubicenyl group, coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, isoa benzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, pentaa phenyl group, a hexacenyl group, a pentacenyl group, a rubicenyl group, coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, isoa benzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group;

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, pentaa phenyl group, a hexacenyl group, a pentacenyl group, a rubicenyl group, coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, isoa benzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein, $Q_1$ to $Q_7$, $Q_{11}$ to $Q_{17}$, $Q_{21}$ to $Q_{27}$ and $Q_{31}$ to $Q_{37}$ may be each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, pentaa phenyl group, a hexacenyl group, a pentacenyl group, a rubicenyl group, coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, isoa benzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group.

As used herein, the term "Ph" refers to a phenyl group, the term "Me" refers to a methyl group, the term "Et" refers to an ethyl group, and the term "ter-Bu" or "Bu$^1$" refers to a tert-butyl group.

Hereinafter, an organic light-emitting device will be described in greater detail with reference to Synthesis Examples and Examples. In Synthesis Examples below, a molar equivalent of A and a molar equivalent of B are the same in the expression "B was used instead of A".

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1: Synthesis of Compound 2

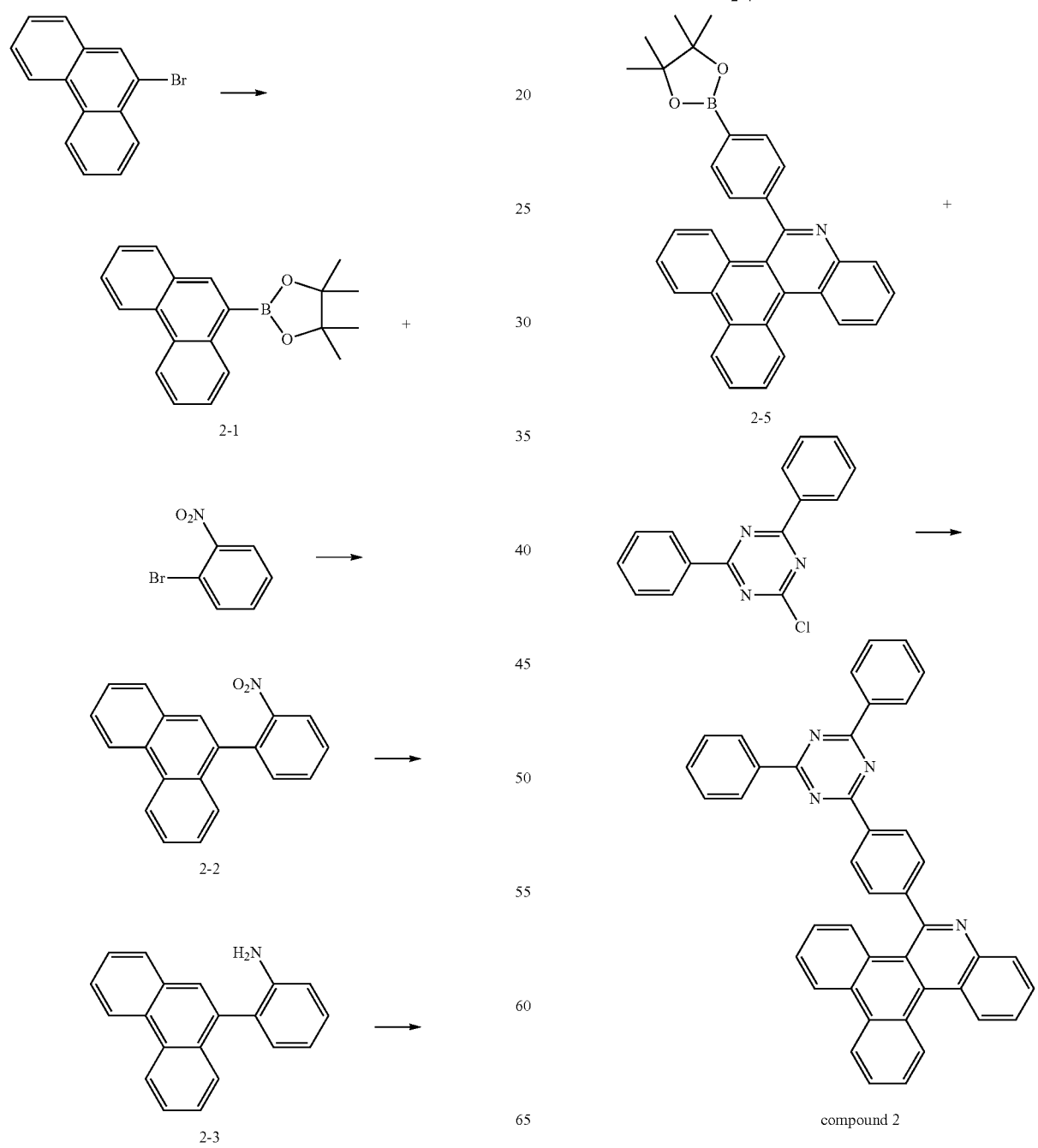

Synthesis of Intermediate 2-1

2.57 g (10 mmol) of 9-bromophenanthrene was dissolved in 30 mL of THF to prepare a dissolution product, and 4 mL of n-butyllithium (2.5 M in hexane) was added to the dissolution product at a temperature of −78° C. to prepare a mixture. After 1 hour, 2.04 mL (10 mmol) of 2-isopropoxy-4,4,5,5-tetramethyl-1,3,2-dioxaborane was added to the mixture at the same temperature. Then, the mixture was stirred at room temperature for 5 hours, water was added thereto, and then a product obtained thereform was washed three times with 30 mL of diethylether. A washed diethylether layer obtained therefrom was dried by using $MgSO_4$ and then reduced pressure dried to obtain a product, and the product was separated and purified by using silica gel column chromatography to obtain 2.28 g of Intermediate 2-1 as a white solid (yield 75%). The compound produced was identified by using LC-MS. $C_{20}H_{21}BO_2$: $M^+$304.2.

Synthesis of Intermediate 2-2

3.04 g (10.0 mmol) of Intermediate 2-1, 2.02 g (10.0 mmol) of 1-bromo-2-nitrobenzene, 0.58 g (0.5 mmol) of $Pd(PPh_3)_4$, 0.16 g (0.5 mmol) of tetrabutylammonium bromide (TBAB) and 3.18 g (30.0 mmol) of $Na_2CO_3$ were dissolved in 60 mL of a mixture solution of toluene/ethanol/$H_2O$ (volume ratio of 3/3/1), and then stirred for 16 hours at a temperature of 80° C. A reaction solution obtained therefrom was cooled to room or ambient temperature and then extracted three times with 60 mL of water and 60 mL of diethylether. An organic layer obtained therefrom was dried with magnesium sulfate and solvents were evaporated therefrom to obtain residues, and the residues were separated and purified by using silica gel column chromatography to obtain 2.39 g of Intermediate 2-2 (yield 80%). The compound produced was identified by using LC-MS. $C_{20}H_{13}NO_2$: $M^+$ 299.1

Synthesis of Intermediate 2-3

2.99 g (10.0 mmol) of Intermediate 2-2, 3.56 g (30 mmol) of tin (Sn), and 5 ml (50 mmol, conc. 36.5%) of hydrochloric acid were dissolved in 60 ml ethanol and a mixture obtained therefrom was stirred for 8 hours at a temperature of 100° C. A reaction solution obtained therefrom was cooled to ambient temperature, 3 g of sodium hydroxide dissolved in 10 mL of water was added to a filtered solution obtained from reduced filtering, and then a product obtained therefrom was extracted three times with 60 mL of water and 60 mL of dichloromethane. An organic layer obtained therefrom was dried with magnesium sulfate and solvents were evaporated therefrom to obtain residues, and the residues were separated and purified by using silica gel column chromatography to obtain 2.42 g (yield 90%) of Intermediate 2-3. The compound produced was identified by using LC-MS. $C_{20}H_{15}N$: $M^+$ 269.1

Synthesis of Intermediate 2-4

2.69 g (10 mmol) of Intermediate 2-3 and 3.66 g (20 mmol) of 4-bromobenzaldehyde were dissolved in 10 mL of trifluoro acetic acid and then stirred in a seal tube at a temperature of 130° C. for three days. A reaction solution obtained therefrom was cooled to ambient temperature, quenched with $NaHCO_3$, and then a product obtained therefrom was extracted three times with 60 mL of water and 60 mL of dichloromethane. An organic layer obtained therefrom was dried with magnesium sulfate, and solvents were evaporated therefrom to obtain residues, and the residues were separated and purified by sing silica gel column chromatography to obtain 1.74 g of Intermediate 2-4 (yield 40%). The compound produced was identified by using LC-MS. Chemical Formula: $C_{27}H_{16}BrN$: $M^+$433.1

Synthesis of Intermediate 2-5

3.37 g of Intermediate 2-5 (yield 70%) was prepared in the same manner as in the method of preparing Intermediate 2-1, except for using Intermediate 2-4 instead of 9-bromophenanthrene. The compound produced was identified by using LC-MS. $C_{33}H_{28}BNO_2$: $M^+$481.2

Synthesis of Compound 2

4.81 g (10 mmol) of Intermediate 2-5, 2.68 g (10 mmol) of 2-chloro-4,6-diphenyl-1,3,5-triazine, 0.58 g (0.5 mmol) of tetrakis(triphenylphosphine)palladium ($Pd(PPh_3)_4$), and 4.14 g (30 mmol) of $K_2CO_3$ were dissolved in 60 mL of a mixture solution of THF/$H_2O$ (volume ratio of 2/1) at a temperature of 80° C. for 16 hours. A reaction solution obtained therefrom was cooled to ambient temperature, 40 mL of water was added thereto, and then a product obtained therefrom was extracted three times with 50 mL of ethyl ether. An organic layer obtained therefrom was dried with magnesium sulfate, and solvents were evaporated therefrom to obtain residues, and the residues were separated and purified by using silica gel column chromatography to obtain 3.52 g (yield 60%) of Compound 2. The compound produced was identified by using LC-MS. $C_{42}H_{26}N_4$: cal. 586.22, found 587.26.

$^1$H NMR (400 MHz, a $CDCl_3$) δ (ppm) 8.90 (d, 1H), 8.84 (d, 1H), 8.81-8.74 (m, 6H), 8.65 (d, 2H), 8.57 (d, 1H), 8.51 (d, 2H), 8.27 (d, 1H), 7.88-7.63 (m, 5H), 7.55-7.41 (m, 7H).

Synthesis Example 2: Synthesis of Compound 10

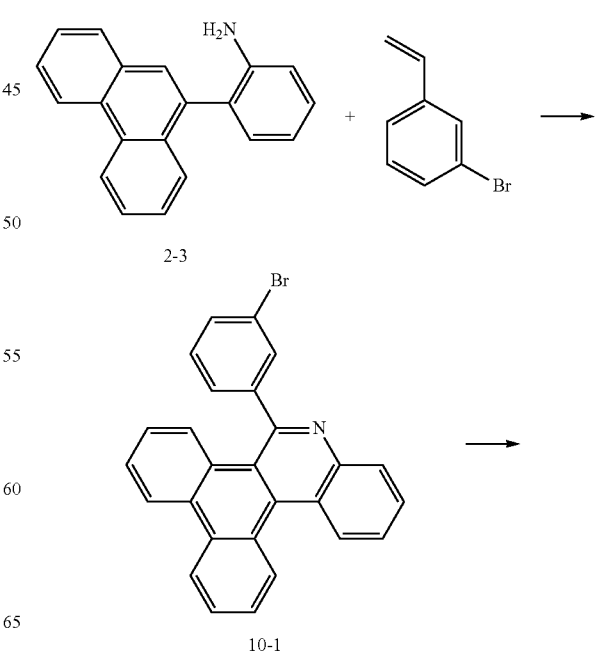

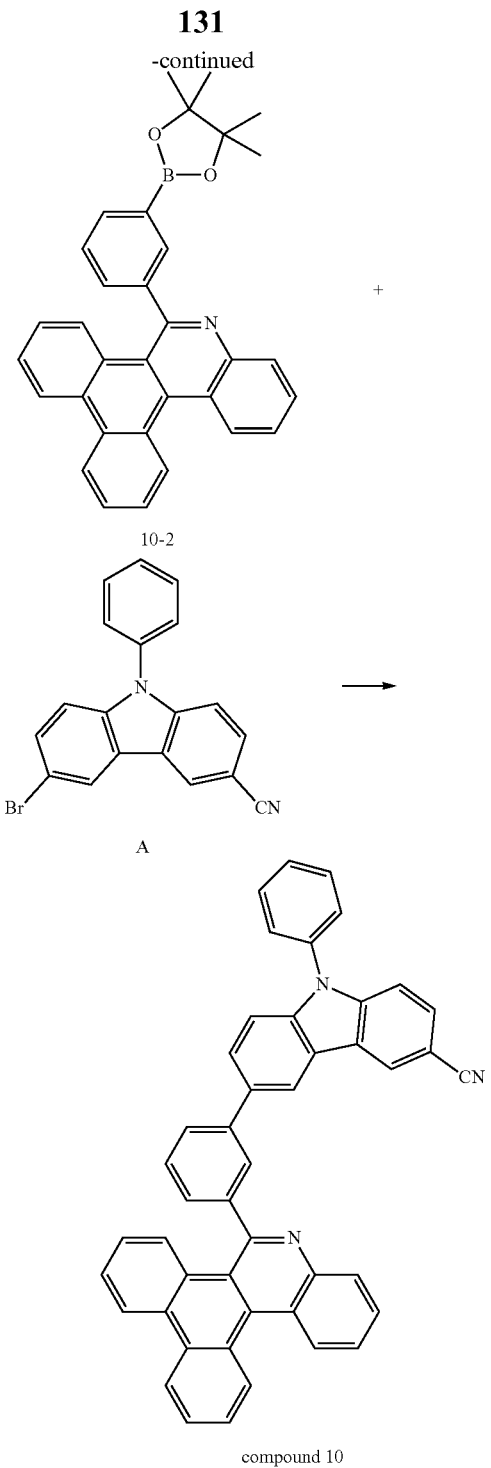

10-2

A compound 10

Synthesis of Intermediate 10-1

1.95 g (yield 45%) of Intermediate 10-1 was synthesized in the same manner as in the method of synthesizing Intermediate 2-4, except that 3-bromobenzaldehyde was used instead of 4-bromobenzaldehyde. The compound produced was identified by using LC-MS. $C_{27}H_{16}BrN$: $M^+433.1$ Synthesis of Intermediate 10-2

3.46 g (yield 72%) of Intermediate 10-2 was synthesized in the same manner as in the method of synthesizing Intermediate 2-5, except that Intermediate 10-1 was used instead of Intermediate 2-4. The compound produced was identified by using LC-MS. $C_{33}H_{28}BNO_2$: $M^+481.2$ Synthesis of Compound 10

4.04 g (yield 65%) of Compound 10 was synthesized in the same manner as in the method of synthesizing Compound 2, except that Intermediate 10-2 was used instead of Intermediate 2-5 and that Intermediate A was used instead of 2-chloro-4,6-diphenyl-1,3,5-triazine. The compound produced was identified by using LC-MS. $C_{46}H_{27}N_3$: cal. 621.22, found 622.32.

$^1$H NMR (400 MHz, a $CDCl_3$) δ (ppm) 8.92 (d, 1H), 8.84 (d, 1H), 8.80-8.74 (m, 2H), 8.64 (s, 1H), 8.57 (d, 1H), 8.47 (s, 1H), 8.30-8.26 (t, 2H), 8.08 (s, 1H), 7.88-7.65 (m, 9H), 7.53-7.46 (m, 6H), 7.34-7.24 (m, 2H)

Synthesis Example 3: Synthesis of Compound 16

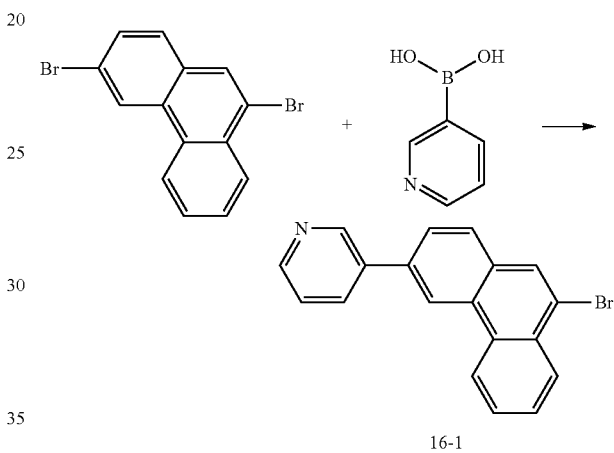

16-1

Synthesis of Intermediate 16-1

5.04 g (15 mmol) of 3,9-dibromophenanthrene, 1.23 g (10 mmol) of pyridine-4-boronic acid, 0.58 g (0.5 mmol) of $Pd(PPh_3)_4$, and 4.14 g (30 mmol) of $K_2CO_3$ were dissolved in 60 mL of a mixture solution of $THF/H_2O$ (volume ratio of 2/1) and then stirred at a temperature of 80° C. for 16 hours. A reaction solution obtained therefrom was cooled to ambient temperature, 40 mL of water was added thereto and then a product obtained therefrom was extracted three times with 50 mL of ethyl ether. An organic layer obtained therefrom was dried with magnesium sulfate, solvents were evaporated therefrom to obtain residues, and the residues were separated and purified by using silica gel column chromatography to obtain 3.52 g (yield 60%) of. The compound produced was identified by using LC-MS. $C_{19}H_{12}BrN$: $M^+333.0$ Synthesis of Compound 16

3.79 g (yield 60%) of Compound 16 was synthesized in the same manner as in the method of synthesizing Compound 2, except that Intermediate 16-1 was used instead of Intermediate 2-1 and that 1-bromopyrene was used instead of 2-chloro-4,6-diphenyl-1,3,5-triazine. The compound produced was identified by using LC-MS.

$C_{48}H_{28}N_2$: cal. 632.23, found 633.34.

$^1$H NMR (400 MHz, a $CDCl_3$) δ (ppm) 8.98 (s, 1H), 8.84-8.75 (m, 3H), 8.68 (s, 1H), 8.58 (d, 2H), 8.31-8.00 (m, 12H), 7.90-7.80 (m, 5H), 7.69-7.65 (m, 2H), 7.50-7.45 (m, 2H)

Synthesis Example 4: Synthesis of Compound 28

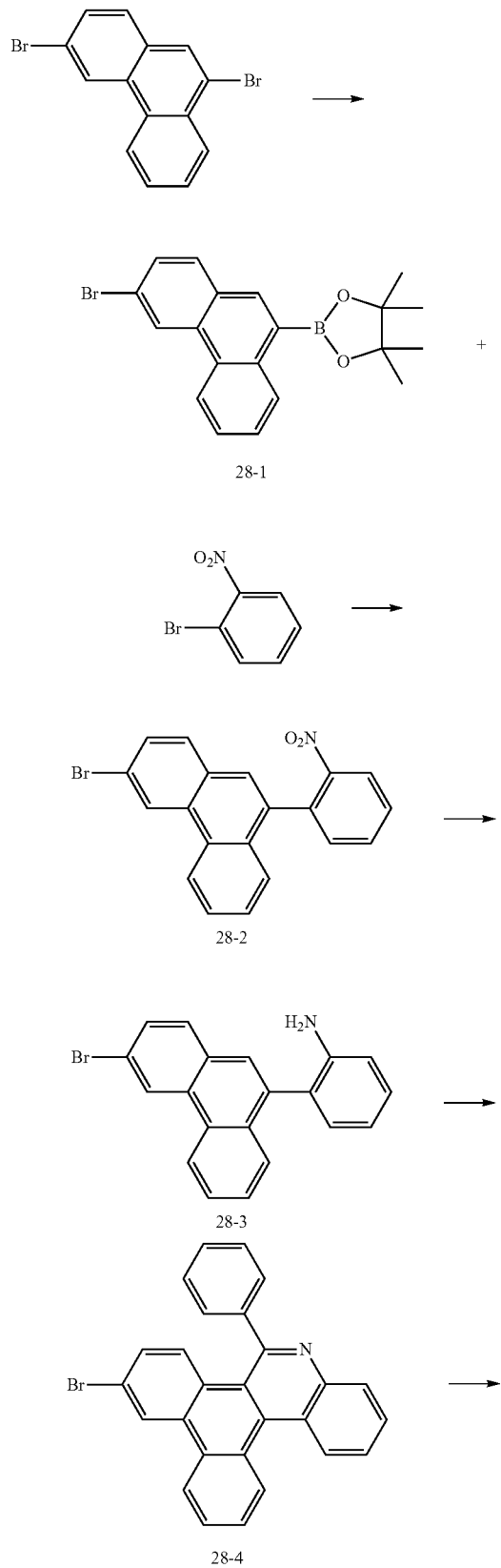

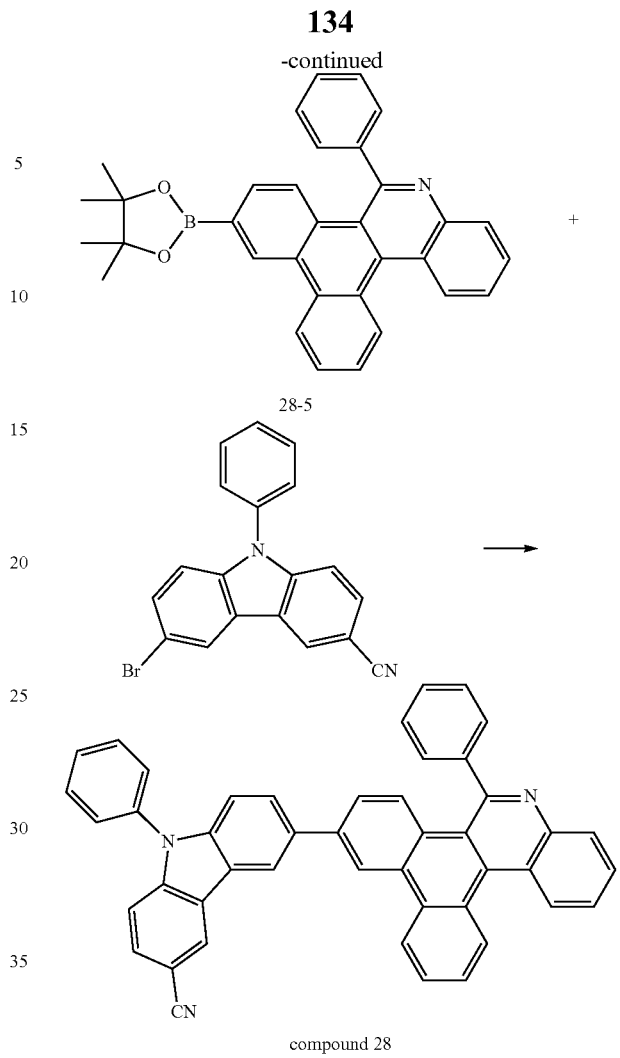

compound 28

Synthesis of Intermediate 28-1

(3.70 g, 11 mmol) of 3,9-dibromophenanthrene was dissolved in 30 mL of THF to prepare a dissolution product and 4 mL of n-butyllithium (2.5 M in hexane) was added to the dissolution product at a temperature of −78° C. to prepare a mixture. After 1 hour, 2.04 ml (10 mmol) of 2-isopropoxy-4,4,5,5-tetramethyl-1,3,2-dioxaborane was added to the mixture at the same temperature. Then, the mixture was stirred at ambient temperature for 5 hours, water was added thereto, and a mixture product obtained therefrom was then washed three times with 30 mL of diethyl ether. A washed diethyl ether layer obtained therefrom was dried by using $MgSO_4$ and then reduced pressure dried to obtain a product, and the product was separated and purified by using silica gel column chromatography to obtain 2.47 g (yield 65%) of Intermediate 28-1 as a white solid. The compound produced was identified by using LC-MS. $C_{20}H_{20}BBrO_2$: $M^+382.1$ Synthesis of Intermediate 28-2

3.83 g (10.0 mmol) of Intermediate 28-1, 4.04 g (20.0 mmol) of 1-bromo-2-nitrobenzene, 0.58 g (0.5 mmol) of $Pd(PPh_3)_4$, 0.16 g (0.5 mmol) of tetrabutylammonium bromide (TBAB), and 3.18 g (30.0 mmol) of $Na_2CO_3$ were dissolved in 60 mL of a mixture solution of toluene/ethanol/$H_2O$ (volume ratio of 3/3/1), and then stirred for 16 hours at a temperature of 80° C. A reaction solution obtained therefrom was cooled to ambient temperature and then extracted three times with 60 mL of water and 60 mL of diethylether.

An organic layer obtained therefrom was dried with magnesium sulfate and solvents were evaporated therefrom to obtain residues, and the residues were separated and purified by using silica gel column chromatography to obtain 2.65 g (yield 70%) of Intermediate 28-2. The compound produced was identified by using LC-MS. $C_{20}H_{12}BrNO_2$: $M^+377.0$ Synthesis of Intermediate 28-3

3.78 g (10.0 mmol) of Intermediate 28-2, 3.56 g (30 mmol) of tin (Sn), and 5 mL (50 mmol, conc. 36.5%) of hydrochloric acid were dissolved in 60 mL ethanol and a mixture obtained therefrom was stirred for 8 hours at a temperature of 100° C. A reaction solution obtained therefrom was cooled to ambient temperature, which was then reduced-pressure filtered, 3 g of sodium hydroxide dissolved in 10 mL was added to a reduced-pressure filtered solution obtained therefrom and then extracted three times with 60 mL of water and 60 mL of dichloromethane. An organic layer obtained therefrom was dried with magnesium sulfate and solvents were evaporated therefrom to obtain residues, and the residues were separated and purified by using silica gel column chromatography to obtain 2.96 g (yield 85%) of Intermediate 28-3. The compound produced was identified by using LC-MS. $C_{20}H_{14}BrN$: $M^+347.0$ Synthesis of Intermediate 28-4

2.69 g (10 mmol) of Intermediate 28-3 and 2.12 g (20 mmol) of benzaldehyde were dissolved in 10 mL of trifluoro acetic acid, and a dissolution product obtained therefrom was stirred in a seal tube at a temperature of 130° C. for three days. A reaction solution obtained therefrom was cooled to ambient temperature, quenched by using NaHCO₃, and then extracted three times with 60 mL of water and 60 mL of dichloromethane. An organic layer obtained therefrom was dried with magnesium sulfate and solvents were evaporated therefrom to obtain residues, and the residues were separated and purified by using silica gel column chromatography to obtain 1.74 g (yield 40%) of Intermediate 28-4. The compound produced was identified by using LC-MS. $C_{27}H_{16}BrN$: $M^+433.1$ Synthesis of Intermediate 28-5

(4.34 g, 10 mmol) of Intermediate 28-4 was dissolved in 30 mL of THF to prepare a dissolution product and 4 mL of n-butyllithium (2.5 M in hexane) was added to the dissolution product at a temperature of −78° C. to prepare a mixture. After 1 hour, 2.04 ml (10 mmol) of 2-isopropoxy-4,4,5,5-tetramethyl-1,3,2-dioxaborane was added to the mixture at the same temperature. Then, the mixture was stirred at ambient temperature for 5 hours, water was added thereto, and then washed three times with 30 mL of diethylether. A washed diethylether layer obtained therefrom was dried by using MgSO₄ and then reduced pressure dried to obtain a product, and the product was separated and purified by using silica gel column chromatography to obtain 3.61 g (yield 75%) of Intermediate 28-5 as a white solid. The compound produced was identified by using LC-MS. $C_{33}H_{28}BNO_2$: $M^+481.2$ Synthesis of Compound 28

4.81 g (10 mmol) of Intermediate 28-5, 3.47 g (10 mmol) of Intermediate A, 0.58 g (0.5 mmol) of Pd(PPh₃)₄, and 4.14 g (30 mmol) K₂CO₃ were dissolved in 60 mL of a mixture solution of THF/H₂O (volume ratio of 2/1) and then stirred at a temperature of 80° C. for 16 hours. A reaction solution obtained therefrom was cooled to ambient temperature, 40 mL of water was added thereto, and then extracted three times with 50 mL of ethylether. A collected organic layer was dried by using magnesium sulfate, solvents were evaporated therefrom, and residues obtained therefrom were separated and purified by using silica gel column chromatography to obtain 4.10 g (yield 66%) of Compound 28. The compound produced was identified by using LC-MS. $C_{46}H_{27}N_3$: cal. 621.22, found 622.32.

¹H NMR (400 MHz, a CDCl₃) δ (ppm) 8.83 (d, 1H), 8.77-8.68 (m, 3H), 8.57 (d, 1H), 8.47 (s, 1H), 8.27-8.17 (m, 3H), 7.99-7.80 (m, 5H), 7.71-7.62 (m, 6H), 7.52-7.46 (m, 5H), 7.33-7.24 (m, 2H)

Synthesis Example 5: Synthesis of Compound 32

3.62 g of Compound 32 (yield 65%) was synthesized in the same manner as in the synthesis of Compound 28, except that 2-pyridine carboxyaldehyde was used instead of benzaldehyde and 1-bromopyrene was used instead of Intermediate A. The compound produced was identified by using LC-MS. $C_{42}H_{24}N_2$: cal. 556.19, found 557.26.

¹H NMR (400 MHz, a CDCl₃) δ (ppm) 9.26 (d, 1H), 8.87 (d, 1H), 8.80-8.65 (m, 4H), 8.37-8.05 (m, 10H), 7.98-7.80 (4H), 7.69-7.64 (m, 2H), 7.48 (t, 1H), 7.36-7.33 (m, 1H)

Synthesis Example 6: Compound 42

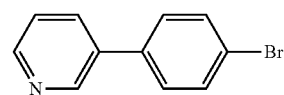

3.36 g of Compound 42 (yield 63%) was synthesized in the same manner as in the synthesis of Compound 28, except that 4-formylbenzonitrile was used instead of benzaldehyde and Intermediate B was used instead of Intermediate A. The compound produced was identified by using LC-MS. $C_{39}H_{23}N_3$: cal. 533.19, found 534.26.

¹H NMR (400 MHz, a CDCl₃) δ (ppm) 8.87-8.70 (m, 4H), 8.60-8.54 (m, 3H), 8.36 (d, 2H), 8.27 (d, 1H), 8.06-7.79 (m, 10H), 7.66 (t, 1H), 7.50-7.42 (m, 2H)

Synthesis Example 7: Synthesis of Compound 56

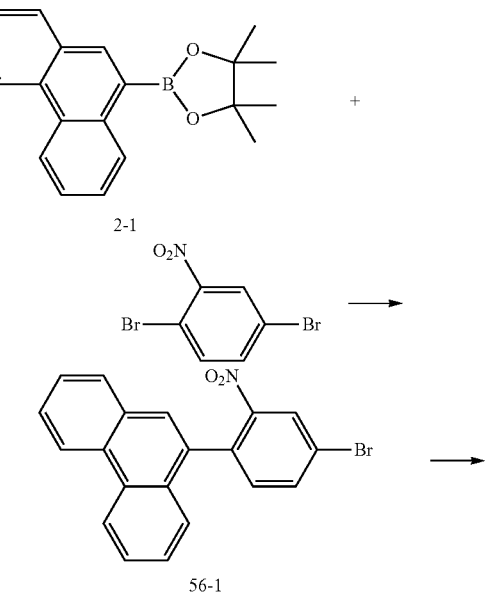

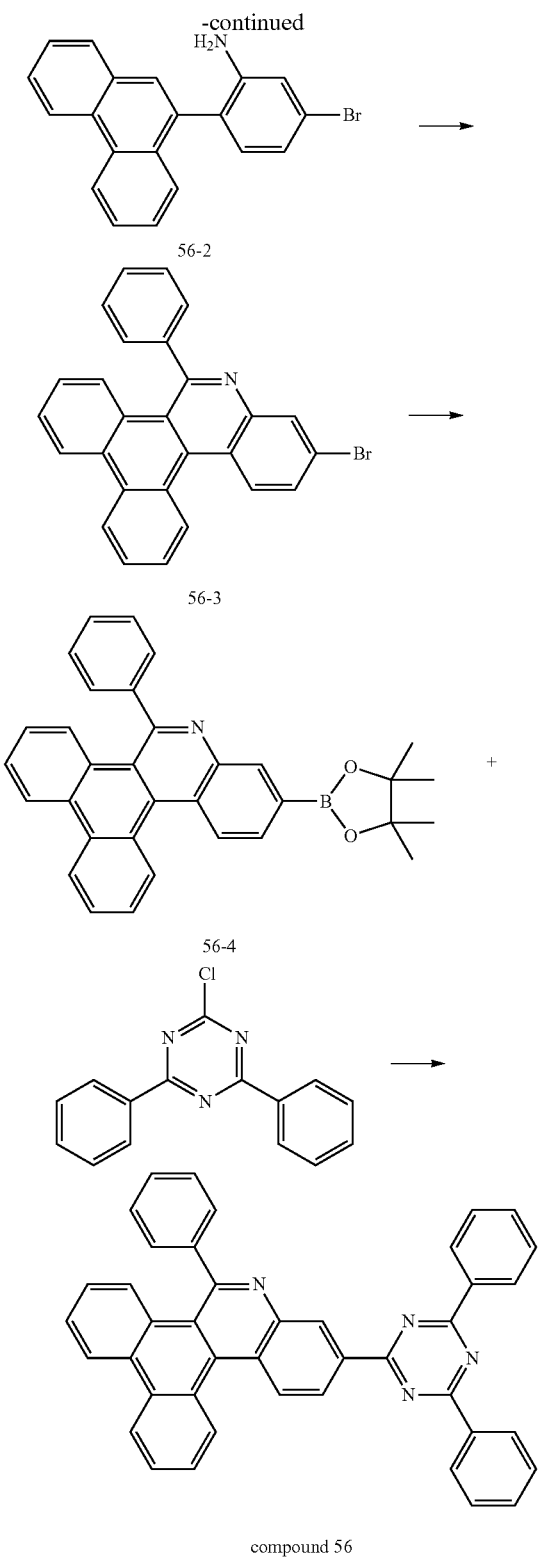

Synthesis of Intermediate 56-1

3.04 g (10.0 mmol) of Intermediate 2-1, 5.622 g (20.0 mmol) of 1,4-dibromo-2-nitrobenzene, 0.58 g (0.5 mmol) of Pd(PPh$_3$)$_4$, 0.16 g (0.5 mmol) of tetrabutylammonium bromide (TBAB), and 3.18 g (30.0 mmol) of Na$_2$CO$_3$ were dissolved in 60 mL of a mixture solution of toluene/ethanol/H$_2$O (volume ratio of 3/3/1), and a resultant solution obtained therefrom was stirred at a temperature of 80° C. for 16 hours. A reaction solution obtained therefrom was cooled to ambient temperature and then extracted three times with 60 mL of water and 60 mL of diethylether. An organic layer obtained therefrom was dried with magnesium sulfate and solvents were evaporated therefrom to obtain residues, and the residues were separated and purified by using silica gel column chromatography to obtain 2.84 g of Intermediate 56-1 (yield 75%). The compound produced was identified by using LC-MS. C$_{20}$H$_{12}$BrNO$_2$: M$^+$377.0

Synthesis of Intermediate 56-2

3.78 g (10.0 mmol) of Intermediate 56-1, 3.56 g (30 mmol) of tin (Sn), and 5 ml (50 mmol, conc. 36.5%) of hydrochloric acid were dissolved in 60 ml ethanol and a mixture obtained therefrom was stirred for 8 hours at a temperature of 100° C. A reaction solution obtained therefrom was cooled to ambient temperature, reduced-pressure filtered and 3 g of sodium hydroxide dissolved in 10 mL was added to a reduced-pressure filtered product obtained therefrom and then extracted three times with 60 mL of water and 60 mL of dichloromethane. An organic layer obtained therefrom was dried with magnesium sulfate and solvents were evaporated therefrom to obtain residues, and the residues were separated and purified by using silica gel column chromatography to obtain 3.13 g (yield 90%) of Intermediate 56-2. C$_{20}$H$_{14}$BrN: M$^+$347.0

Synthesis of Intermediate 56-3

3.48 g (10 mmol) of Intermediate 56-2 and 2.12 (20 mmol) of benzaldehyde were dissolved in 10 mL of trifluoro acetic acid, and a dissolution product obtained therefrom was stirred in a seal tube at a temperature of 130° C. for three days. A reaction solution obtained therefrom was cooled to ambient temperature, quenched by using NaHCO$_3$, and then extracted three times with 60 mL of water and 60 mL of dichloromethane. An organic layer obtained therefrom was dried with magnesium sulfate and solvents were evaporated therefrom to obtain residues, and the residues were separated and purified by using silica gel column chromatography to obtain 1.74 g (yield 40%) of Intermediate 56-3. The compound produced was identified by using LC-MS. C$_{27}$H$_{16}$BrN: M$^+$ 433.1

Synthesis of Intermediate 56-4

(4.34 g, 10 mmol) of Intermediate 56-3 was dissolved in 30 mL of THF to prepare a dissolution product and 4 mL of n-butyllithium (2.5 M in hexane) was added to the dissolution product at a temperature of −78° C. to prepare a mixture. After an hour, 2.04 ml (10 mmol) of 2-isopropoxy-4,4,5,5-tetramethyl-1,3,2-dioxaborane was added to the mixture at the same temperature. Then, the mixture was stirred at ambient temperature for 5 hours, water was added thereto, and then washed three times with 30 mL of diethylether. A washed diethylether layer obtained therefrom was dried by using MgSO$_4$ and then reduced pressure dried to obtain a product, and the product was separated and purified by using silica gel column chromatography to obtain 3.37 g (yield 70%) of Intermediate 56-4 as a white solid. The compound produced was identified by using LC-MS. C$_{33}$H$_{28}$BNO$_2$: M$^+$481.2

Synthesis of Compound 56

4.81 g (10 mmol) of Intermediate 2-1, 2.68 g (10 mmol) of 2-chloro-4,6-diphenyl-1,3,5-triazine, 0.58 g (0.5 mmol) of Pd(PPh$_3$)$_4$, 4.14 g (30 mmol) of K$_2$CO$_3$ were dissolved in 60 mL of a mixture solution of THF/H$_2$O (volume ratio of 2/1), and a resultant solution obtained therefrom was stirred at a temperature of 80° C. for 16 hours. A reaction solution obtained therefrom was cooled to ambient temperature, 40 mL of water was added thereto, and then extracted three times with 50 mL of ethylether. An organic layer obtained therefrom was dried with magnesium sulfate and solvents were evaporated therefrom to obtain residues, and the residues were separated and purified by using silica gel column chromatography to obtain 3.82 g of Compound 56 (yield 60%). The compound produced was identified by using LC-MS. $C_{42}H_{26}N_4$: cal. 586.22, found 587.32.

$^1$H NMR (400 MHz, a CDCl$_3$) δ (ppm) 9.16 (s, 1H), 9.05 (m, 4H), 8.81-8.74 (m, 6H), 8.02-7.97 (m, 2H), 7.83-7.60 (m, 7H), 7.54-7.41 (m, 6H)

Example 1

As an anode, a 15 Ω/cm² ITO glass substrate (1,200 Å, Corning) was cut into a size of about 50 mm×50 mm×0.7 mm, ultrasonically washed with isopropyl alcohol and pure water for 5 minutes each, irradiated with UV for 30 minutes, exposed to ozone, and then loaded onto a vacuum deposition device.

2-TNATA was deposited on the ITO anode to form an HIL having a thickness of 600 Å, NPB was deposited on the HIL to form an HTL having a thickness of 300 Å. Thereafter, ADN (host) and DPAVBi (dopant) were co-deposited on the HTL at a weight ratio of 98:2 to form an EML having a thickness of 300 Å.

Thereafter Compound 2 was deposited on the EML to form an ETL having a thickness of 300 Å, LiF was deposited on the ETL to form an EIL having a thickness of 10 Å, Al was deposited on the EIL into a thickness of 10 Å, Al was deposited on the EIL to form a cathode having a thickness of 3000 Å, to thereby manufacture an organic light-emitting device.

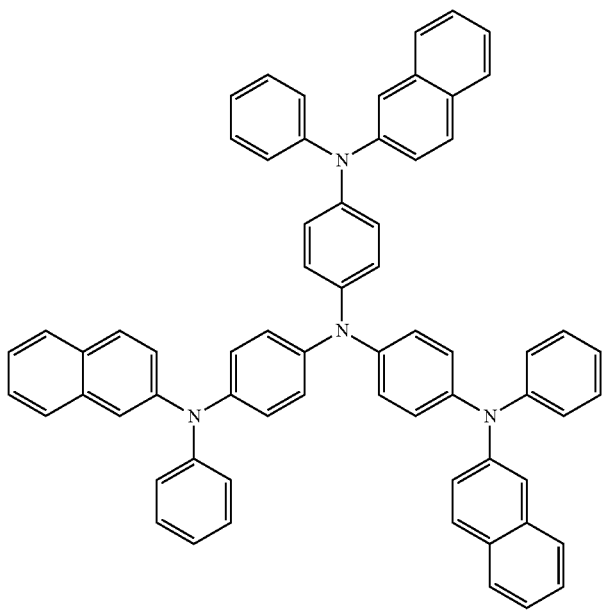

2-TNATA

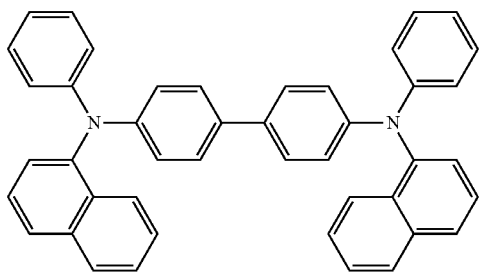

NPB

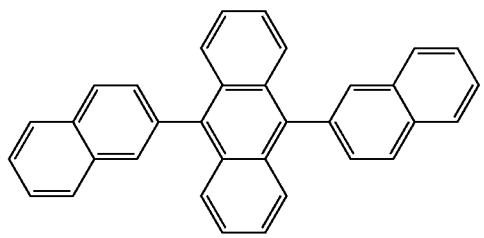

ADN

-continued

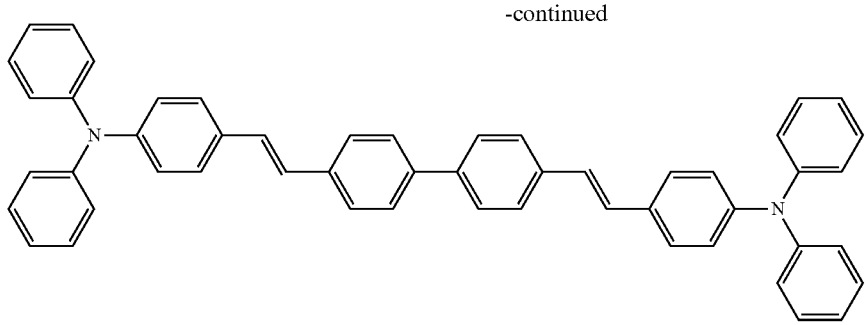

DPAVBI

Example 2

An organic light-emitting device was manufactured in the same manner as in Example 1, except that Compound 10 was used instead of Compound 2 when forming an ETL.

Example 3

An organic light-emitting device was manufactured in the same manner as in Example 1, except that Compound 16 was used instead of Compound 2 when forming an ETL.

Example 4

An organic light-emitting device was manufactured in the same manner as in Example 1, except that Compound 28 was used instead of Compound 2 when forming an ETL.

Example 5

An organic light-emitting device was manufactured in the same manner as in Example 1, except that Compound 32 was used instead of Compound 2 when forming an ETL.

Example 6

An organic light-emitting device was manufactured in the same manner as in Example 1, except that Compound 42 was used instead of Compound 2 when forming an ETL.

Example 7

An organic light-emitting device was manufactured in the same manner as in Example 1, except that Compound 56 was used instead of Compound 2 when forming an ETL.

Comparative Example 1

An organic light-emitting device was manufactured in the same manner as in Example 1, except that Alq$_3$ was used instead of Compound 2 when forming an ETL.

Comparative Example 2

An organic light-emitting device was manufactured in the same manner as in Example 1, except that Compound A, below, was used instead of Compound 2 when forming an ETL.

<Compound A>

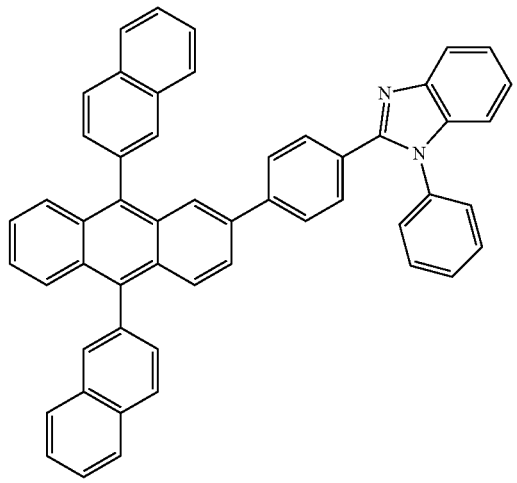

Evaluation Example 1

Driving voltages, current densities, brightness, efficiencies, emission colors, and half-life spans of the organic light-emitting device manufactured in Examples 1 to 7 and Comparative Examples 1 and 2 were measured by using Kethley SMU 236 and spectrophotometer PR650 and results obtained therefrom are shown in Table 1. The term, "half-life span" refers to an amount of time taken for the level of brightness to reach a level that is 50% of the initial level of brightness.

TABLE 1

| | Material | Driving voltage (V) | Current density (mA/cm$^2$) | Brightness (cd/m$^2$) | Efficiency (cd/A) | Emission color | Half-life (hr @ 100 mA/cm$^2$) |
|---|---|---|---|---|---|---|---|
| Example 1 | Compound 2 | 5.90 | 50 | 3,150 | 6.30 | blue | 222 hr |
| Example 2 | Compound 10 | 5.58 | 50 | 2,900 | 5.80 | blue | 265 hr |

TABLE 1-continued

| | Material | Driving voltage (V) | Current density (mA/cm$^2$) | Brightness (cd/m$^2$) | Efficiency (cd/A) | Emission color | Half-life (hr @ 100 mA/cm$^2$) |
|---|---|---|---|---|---|---|---|
| Example 3 | Compound 16 | 5.84 | 50 | 3,240 | 6.48 | blue | 300 hr |
| Example 4 | Compound 28 | 5.96 | 50 | 3,110 | 6.22 | blue | 315 hr |
| Example 5 | Compound 32 | 6.21 | 50 | 3,420 | 6.84 | blue | 233 hr |
| Example 6 | Compound 42 | 6.05 | 50 | 3,350 | 6.70 | blue | 251 hr |
| Example 7 | Compound 56 | 5.98 | 50 | 3,050 | 6.10 | blue | 286 hr |
| Comparative Example 1 | Alq$_3$ | 7.35 | 50 | 2,065 | 4.13 | blue | 145 hr |
| Comparative Example 2 | Compound A | 6.12 | 50 | 2,465 | 4.93 | blue | 170 hr |

According to the Table 1 above, it may be seen that driving voltages, current densities, brightness, efficiencies, emission colors, and half-life spans of the organic light-emitting devices manufactured in Examples 1 to 7 were better than those of the organic light-emitting devices manufactured in Comparative Examples 1 and 2.

As described above, according to the one or more of the above embodiments, the organic light-emitting device including the condensed cyclic compound may have low driving voltage, high efficiency, high brightness, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A condensed cyclic compound represented by Formula 1, below:

<Formula 1>

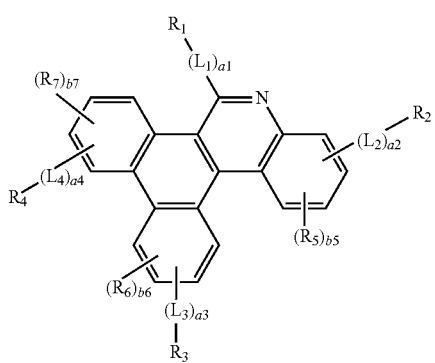

in Formula 1, $L_1$ to $L_4$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

a1 to a4 may be each independently selected from 0, 1, 2 and 3;

$R_1$ to $R_4$ may be each independently selected from hydrogen, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed polycyclic group, a substituted or unsubstituted monovalent non-aromatic condensed hetero-polycyclic group, —P(=O)(Q$_1$)(Q$_2$), and —S(=O)$_2$(Q$_1$);

$R_5$ to $R_7$ may be each independently selected from hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed hetero-polycyclic group;

b5 to b7 are each independently selected from 1, 2, and 3;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed hetero-polycyclic group may be selected from:

deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed hetero-polycyclic group;

$C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed hetero-polycyclic group, each substituted with at least one selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group; and —P(=O)($Q_{11}$)($Q_{12}$) and —S(=O)$_2$($Q_{11}$); wherein, $Q_1$, $Q_2$, $Q_{11}$ and $Q_{12}$ may be each independently selected from a $C_6$-$C_{60}$ aryl group, and a $C_2$-$C_{60}$ heteroaryl group, provided that i) when *-($L_1$)$_{a1}$-$R_1$ in Formula 1 is a phenyl group, $R_2$ and $R_5$ are not a methyl group, ii) when *-($L_1$)$_{a1}$-$R_1$ in Formula 1 is not a phenyl group, at least one of $R_1$ to $R_7$ are not hydrogen, iii) when *-($L_1$)$_{a1}$-$R_1$ in Formula 1 is —P(=O)($Q_1$)($Q_2$), and $Q_1$ and $Q_2$ are phenyl groups, $R_5$ is not a methyl group, and iv) when *-($L_1$)$_{a1}$-$R_1$ in Formula 1 is a phenyl group, at least one of $R_2$, $R_3$, and $R_4$ is not hydrogen.

2. The condensed cyclic compound as claimed in claim 1, wherein $L_1$ to $L_4$ are each independently groups selected from:

phenylene, pentalenylene, indenylene, naphthylene, azulenylene, heptalenylene, indacenylene, acenaphthylene, fluorenylene, spiro-fluorenylene, benzofluorenylene, dibenzofluorenylene, phenalenylene, phenanthrenylene, anthracenylene, fluoranthenylene, triphenylenylene, pyrenylene, chrysenylene, naphthacenylene, picenylene, perylenylene, pentaphenylene, hexacenylene, pentacenylene, rubicenylene, coronenylene, ovalenylene, pyrrolylene, thiophenylene, furanylene, imidazolylene, pyrazolylene, thiazolylene, isothiazolylene, oxazolylene, isooxazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzoimidazolylene, benzofuranylene, benzothiophenylene, isobenzothiazolylene, benzooxazolylene, isobenzooxazolylene, triazolylene, tetrazolylene, oxadiazolylene, triazinylene, dibenzofuranylene, dibenzothiophenylene, benzocarbazolylene, and dibenzocarbazolylene; and phenylene, pentalenylene, indenylene, naphthylene, azulenylene, heptalenylene, indacenylene, acenaphthylene, fluorenylene, spiro-fluorenylene, benzofluorenylene, dibenzofluorenylene, phenalenylene, phenanthrenylene, anthracenylene, fluoranthenylene, triphenylenylene, pyrenylene, chrysenylene, naphthacenylene, picenylene, perylenylene, pentaphenylene, hexacenylene, pentacenylene, rubicenylene, coronenylene, ovalenylene, pyrrolylene, thiophenylene, furanylene, imidazolylene, pyrazolylene, thiazolylene, isothiazolylene, oxazolylene, isooxazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzoimidazolylene, benzofuranylene, benzothiophenylene, isobenzothiazolylene, benzooxazolylene, isobenzooxazolylene, triazolylene, tetrazolylene, oxadiazolylene, triazinylene, dibenzofuranylene, dibenzothiophenylene, benzocarbazolylene and dibenzocarbazolylene, each substituted with at least one group selected from deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a cyclopentyl, cyclohexyl, cycloheptyl, cyclopentenyl, cyclohexenyl, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, dibenzocarbazolyl, thiadiazolyl, and imidazopyridinyl.

3. The condensed cyclic compound as claimed in claim 1, wherein $L_1$ to $L_4$ are each independently selected from groups represented by Formulae 3-1 to 3-30 below:

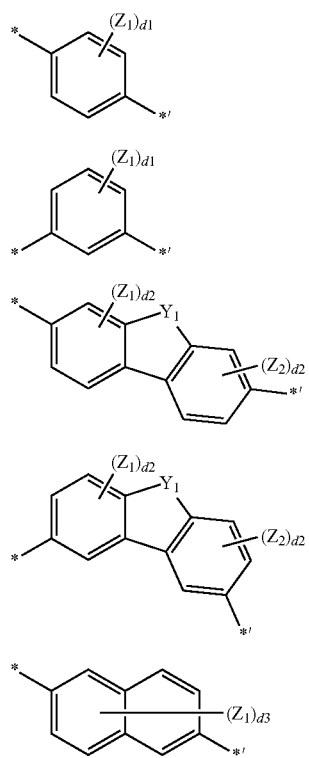

3-1

3-2

3-3

3-4

3-5

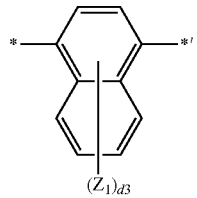

3-6

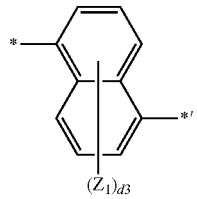

3-7

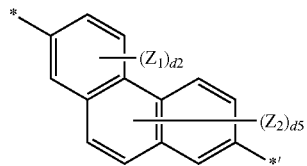

3-8

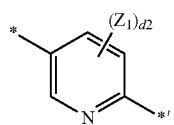

3-9

3-10

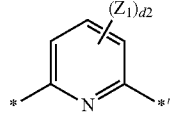

3-11

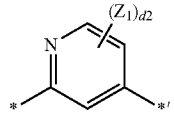

3-12

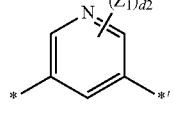

3-13

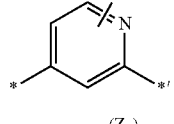

3-14

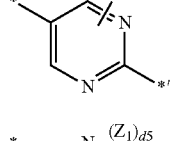

3-15

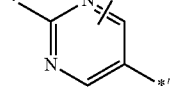

3-16

-continued 3-17 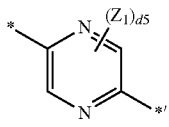

3-18 

3-19 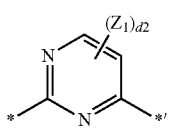

3-20 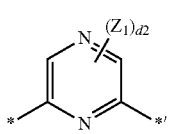

3-21 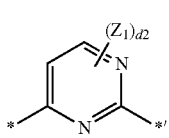

3-22 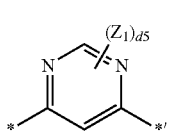

3-23 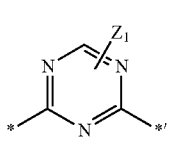

3-24 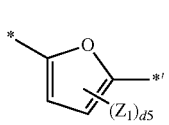

3-25 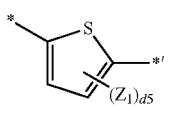

3-26 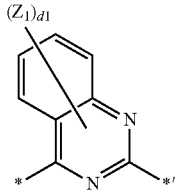

3-27 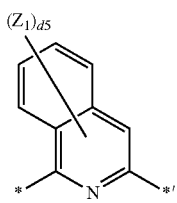

-continued

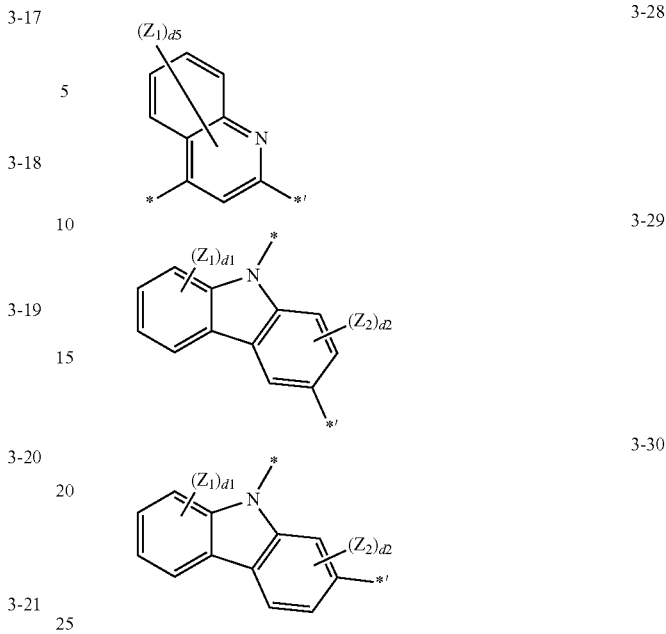

in Formulae 3-1 to 3-30, $Y_1$ is O, S, a $C(Z_3)(Z_4)$, $N(Z_5)$, or $Si(Z_6)(Z_3)$;

$Z_1$ to $Z_7$ are each independently selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is an integer of 1 to 4;
d2 is an integer of 1 to 3;
d3 is an integer of 1 to 6;
d4 is an integer of 1 to 8;
d5 is an integer of 1 or 2;
d6 is an integer of 1 to 5; and
* and *' are binding sites to neighboring atoms.

4. The condensed cyclic compound as claimed in claim 1, wherein $L_1$ to $L_4$ are each independently selected from groups represented by Formulae 4-1 to 4-21 below:

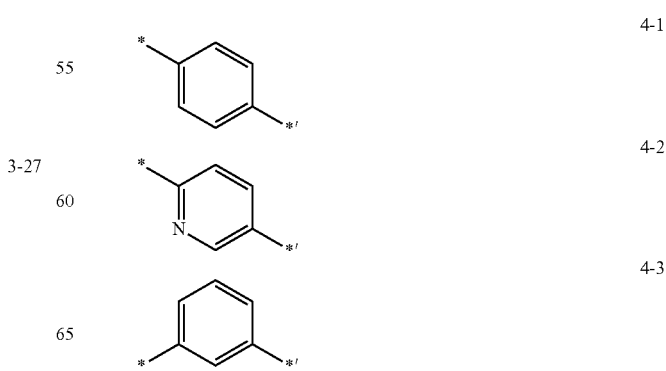

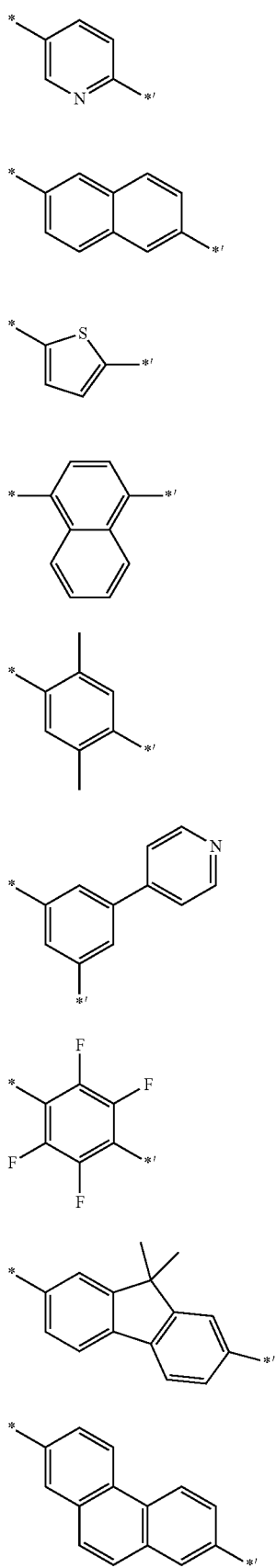
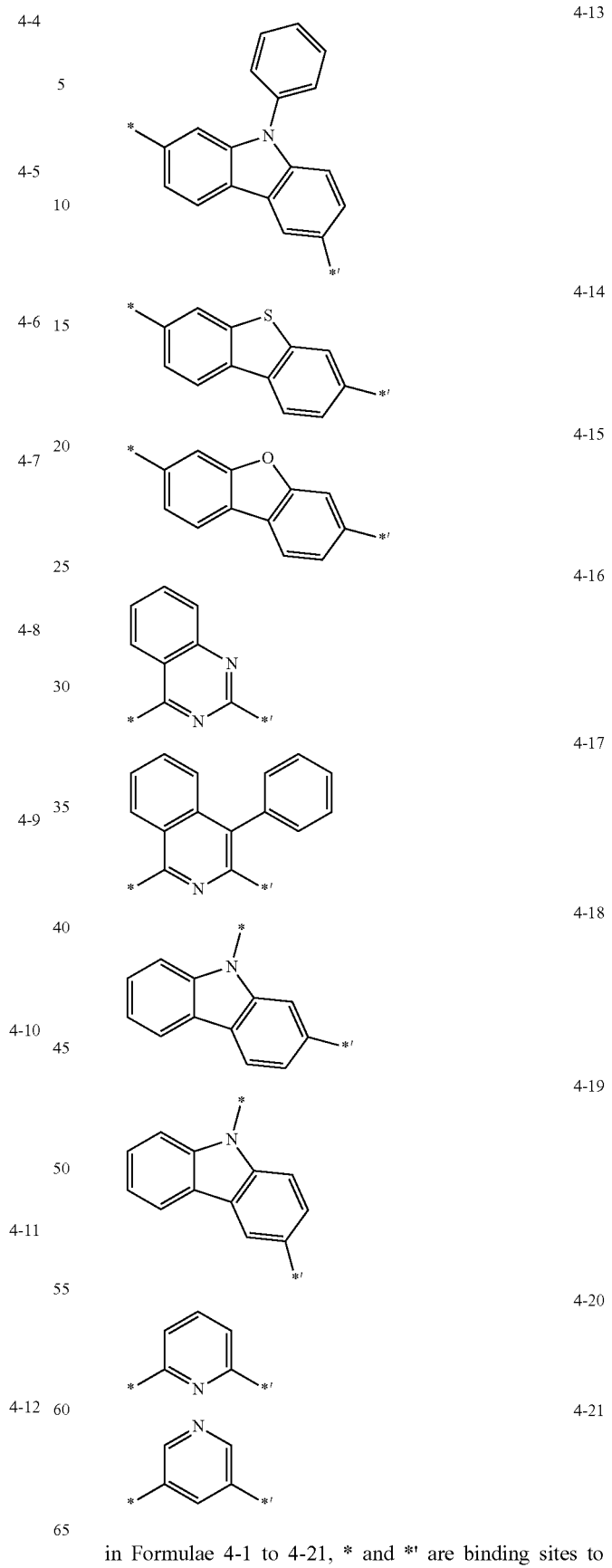
in Formulae 4-1 to 4-21, * and *' are binding sites to neighboring atoms.

5. The condensed cyclic compound as claimed in claim 1, wherein a1 to a4 are each independently selected from 0, 1, and 2.

6. The condensed cyclic compound as claimed in claim 1, wherein a2 to a4 are 0.

7. The condensed cyclic compound as claimed in claim 1, wherein $R_1$ to $R_4$ are each independently groups selected from:

hydrogen, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyi, benzooxazolyl, isobenzooxazolyl, triazolyl, tetrazolyl, oxadiazolyl, triazinyl, dibenzofuranyl, dibenzothiophenyl, a dibenzosilolyl group, benzocarbazolyl, dibenzocarbazolyl, benzoxanthenyl, —P(=O)($Q_1$)($Q_2$), and —S(=O)$_2$ ($Q_1$), in which $Q_1$ and $Q_2$ are each independently a $C_6$-$C_{60}$ aryl group; and phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, a dibenzosilolyl group, benzocarbazolyl, dibenzocarbazolyl and benzoxanthenyl, each substituted with at least one group selected from deuterium, —F, —Cl, —Br, —I, a hydroxyl group, a cyano group, a nitro group, a $C_1$-$C_{20}$ alkyl, a $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxazolyl, oxadiazolyl, triazinyl, dibenzofuranyl, dibenzothiophenyl, benzocarbazolyl, and dibenzocarbazolyl.

8. The condensed cyclic compound as claimed in claim 1, wherein $R_1$ to $R_4$ are each independently groups selected from:

hydrogen, phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl, benzoxanthenyl, —P(=O)($Q_1$)($Q_2$), and —S(=O)$_2$($Q_1$), in which $Q_1$ and $Q_2$ are each independently selected from a phenyl group and a naphthyl group; and phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl and benzoxanthenyl, each substituted with at least one selected from deuterium, —F, —Cl, —Br, —I, a cyano group, a nitro group, methyl, ethyl, n-propyl, tert-butyl, methoxy, ethoxy, tert-butoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl.

9. The condensed cyclic compound as claimed in claim 1, wherein $R_1$ to $R_4$ are each independently selected from hydrogen, —P(=O)(Ph)$_2$, —S(=O)$_2$(Ph) and a group represented by any one of Formulae 5-1 to 5-44:

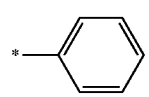

5-1

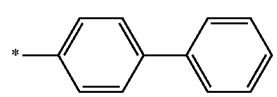

5-2

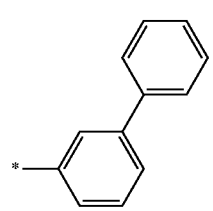

5-3

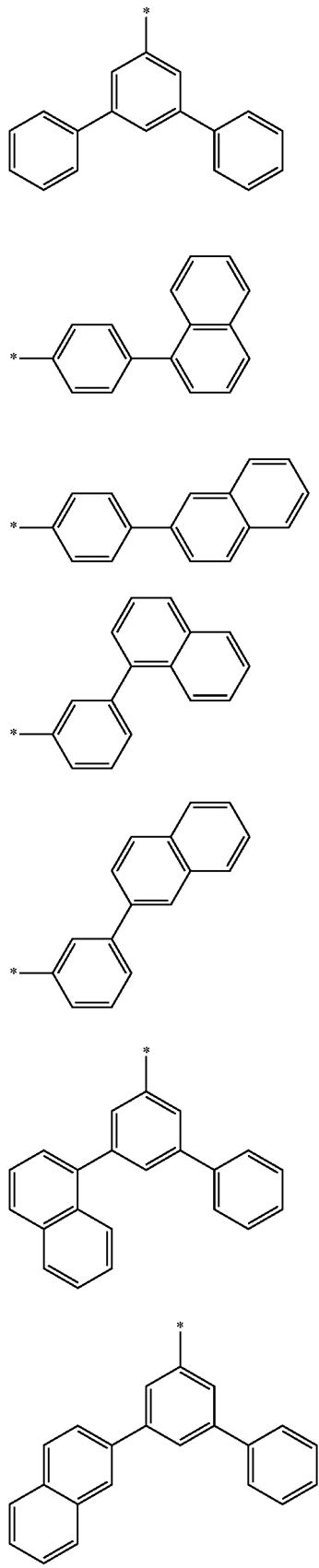
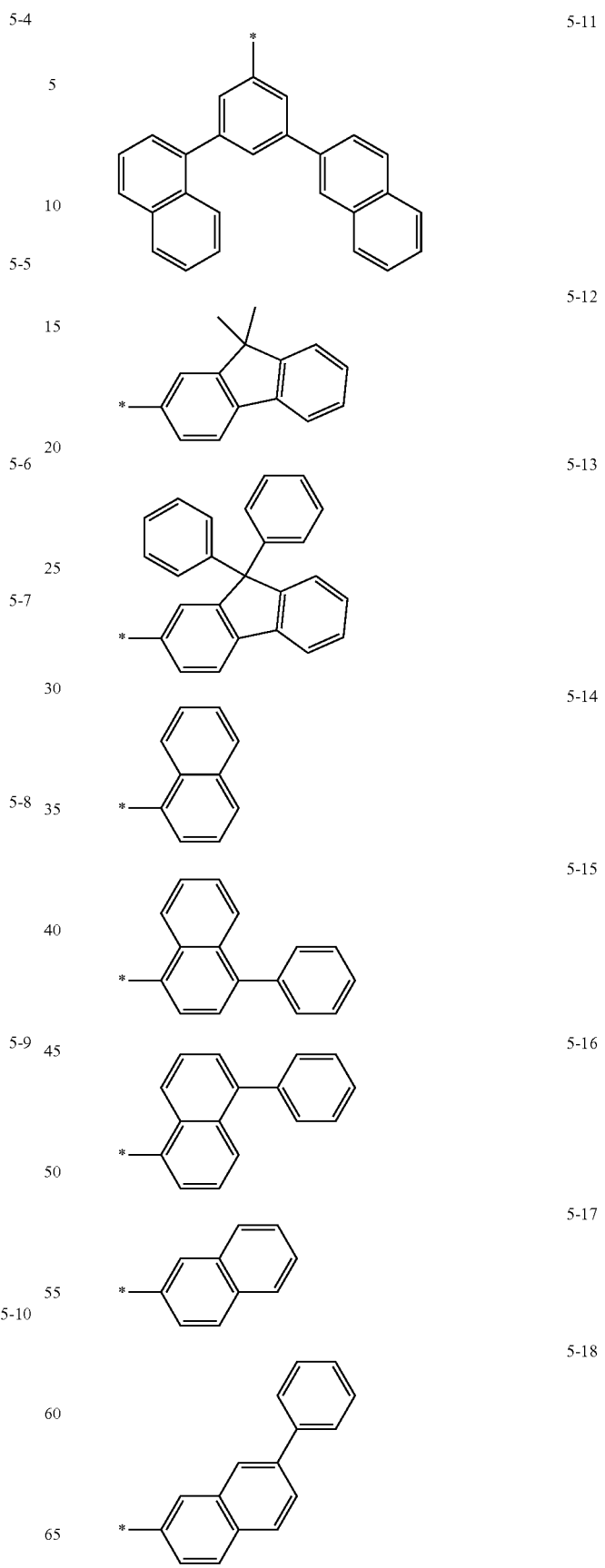

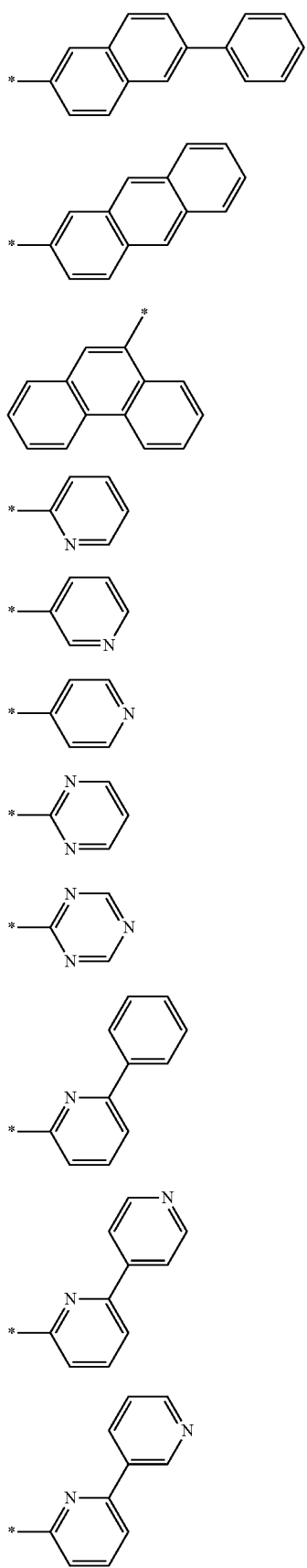
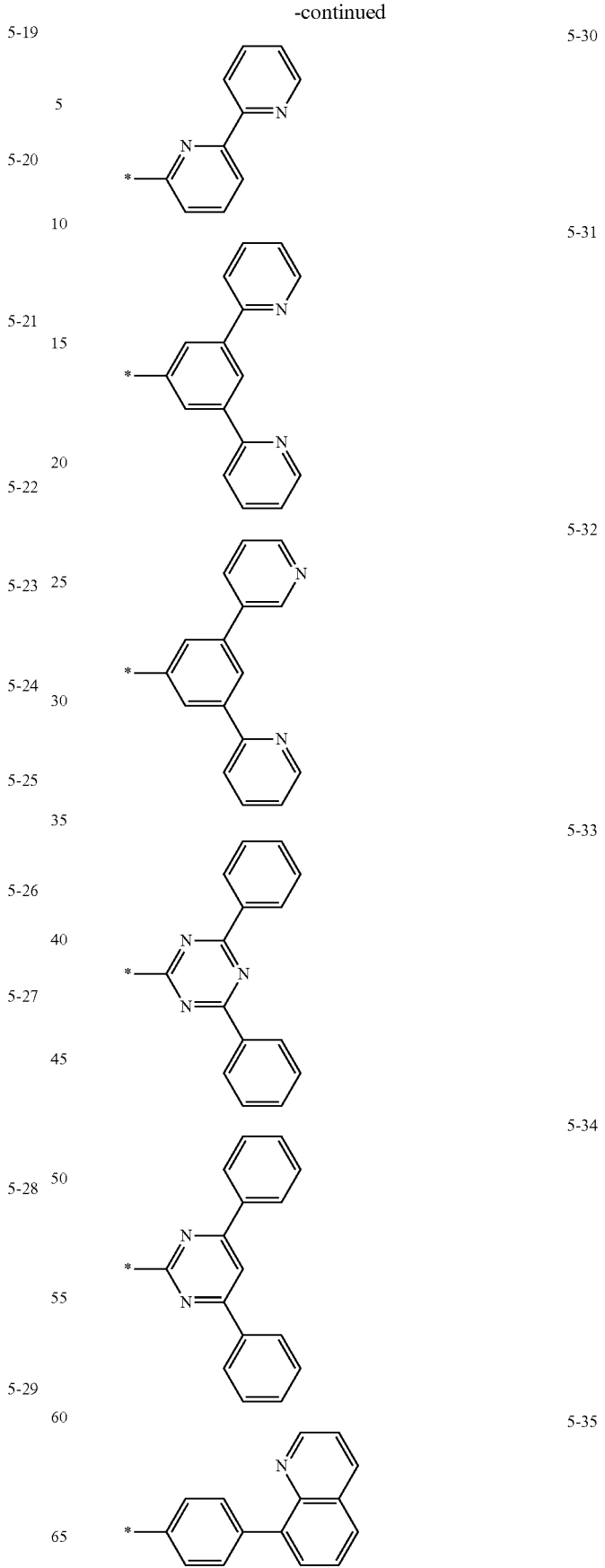

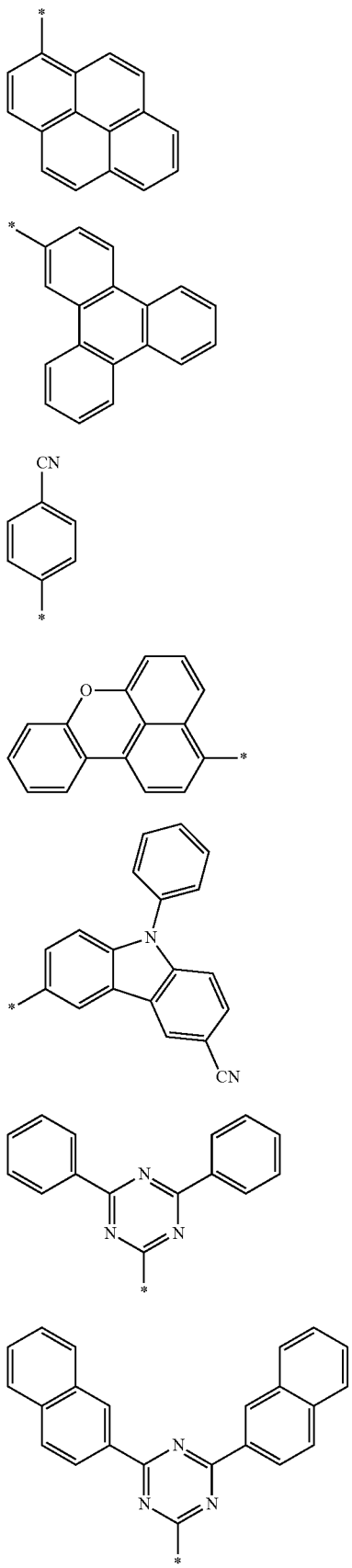

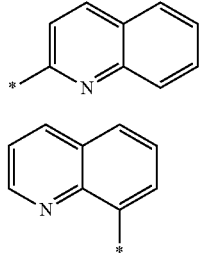

in Formulae 5-1 to 5-44, * is a binding site to a neighboring atom.

10. The condensed cyclic compound as claimed in claim 1, wherein $R_5$ to $R_7$ are each independently groups selected from:

hydrogen, deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, $C_1$-$C_{20}$ alkyl, $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, a dibenzosilolyl group, benzocarbazolyl, dibenzocarbazolyl, and benzoxanthenyl; and phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, a dibenzosilolyl group, benzocarbazolyl, dibenzocarbazolyl and benzoxanthenyl, each substituted with at least one group selected from deuterium, —F, —Cl, —Br, —I, a hydroxyl group, a cyano group, a nitro group, $C_1$-$C_{20}$ alkyl, $C_1$-$C_{20}$ alkoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl.

11. The condensed cyclic compound as claimed in claim 1, wherein $R_5$ to $R_7$ are each independently groups selected from:

hydrogen, deuterium, —F, —Cl, —Br, —I, a hydroxyl group, a cyano group, a nitro group, methyl, ethyl, n-propyl, tert-butyl, methoxy, ethoxy, phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl, and benzoxanthenyl; and phenyl, naphthyl, fluorenyl, phenanthrenyl, anthracenyl, triphenylenyl, pyrenyl, chrysenyl, pyrrolyl, thiophenyl, furanyl, imidazolyl, pyridinyl, pyrazinyl, pyrimidinyl, pyridazinyl, indolyl quinolinyl, isoquinolinyl, carbazolyl, phenanthrolinyl, benzoimidazolyl, triazinyl and benzoxanthenyl, each substituted with at least one group selected from deuterium, —F, —Cl, —Br, —I, a cyano group, a nitro group, methyl, ethyl, n-propyl, tert-butyl, methoxy, ethoxy, tert-butoxy, phenyl, pentalenyl, indenyl, naphthyl, azulenyl, heptalenyl, indacenyl, acenaphthyl, fluorenyl, spiro-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, pyrrolyl, thiophenyl, furanyl, imidazolyl, pyrazolyl, thiazolyl, isothiazolyl, oxazolyl, isooxazolyl, pyridinyl, pyrazinyl, pyrimidinyl, pyridazinyl, isoindolyl, indolyl, indazolyl, purinyl, quinolinyl, isoquinolinyl, carbazolyl, benzoquinolinyl, phthalazinyl, naphthyridinyl, quinoxalinyl, quinazolinyl, cinnolinyl, phenanthridinyl, acridinyl, phenanthrolinyl, phenazinyl, benzoimidazolyl, benzofuranyl, benzothiophenyl, isobenzothiazolyl, benzooxazolyl, isobenzooxazolyl, triazolyl, tetrazolyl, oxadiazolyl, triazinyl, dibenzofuranyl, dibenzothiophenyl, benzocarbazolyl, and dibenzocarbazolyl.

12. The condensed cyclic compound as claimed in claim 1, wherein $R_5$ to $R_7$ are each independently selected from hydrogen, deuterium, a cyano group, a nitro group and a group represented by any one of Formulae 5-1 to 5-44:

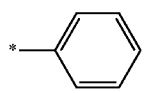
5-1

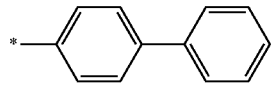
5-2

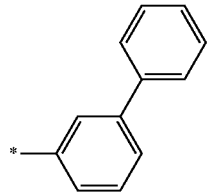
5-3

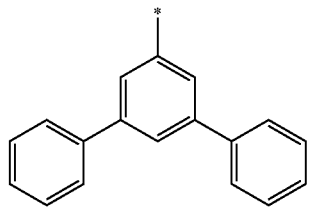
5-4

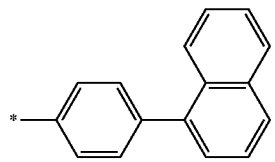
5-5

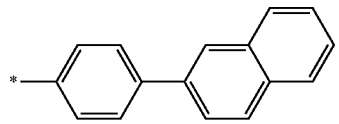
5-6

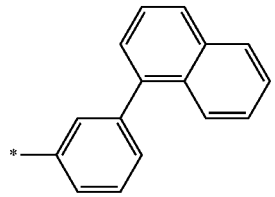
5-7

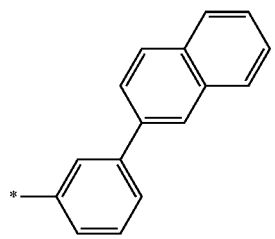
5-8

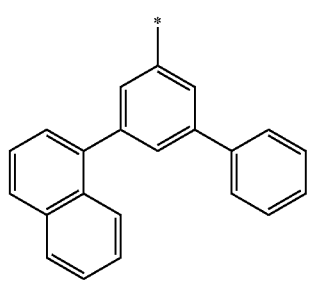
5-9

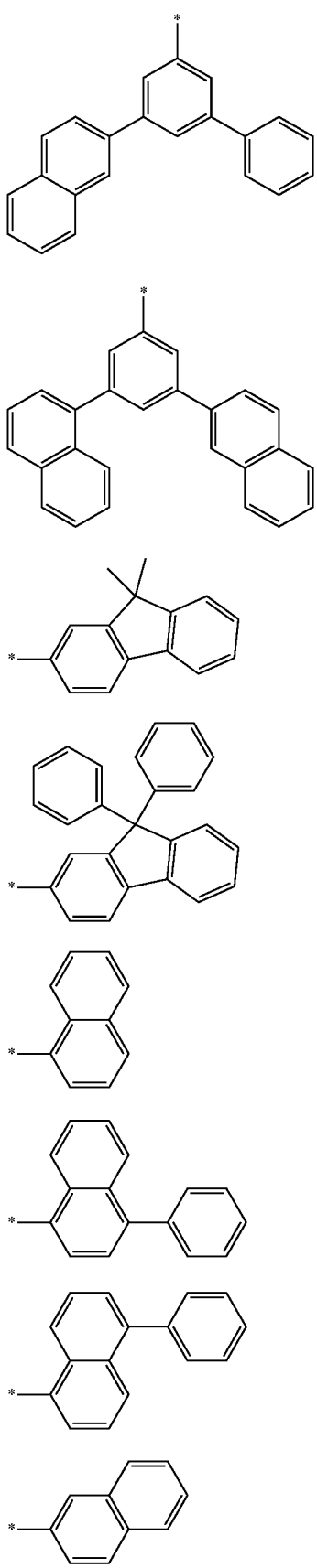
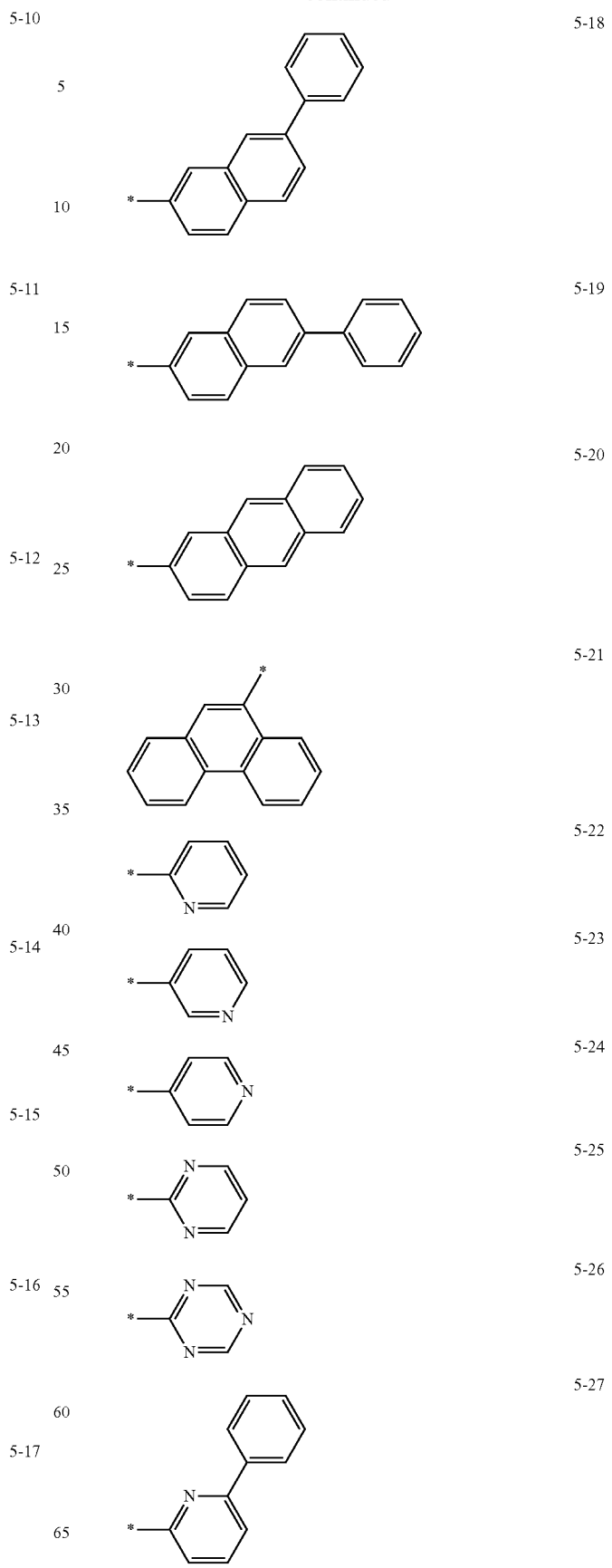

165
-continued
5-28
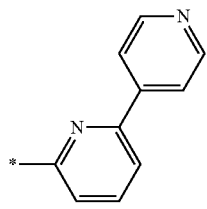
5-29
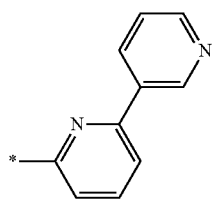
5-30
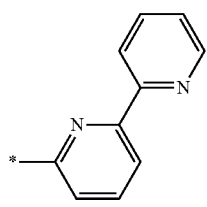
5-31
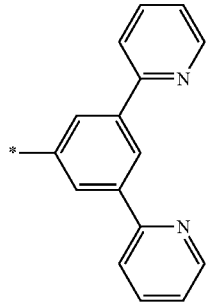
5-32
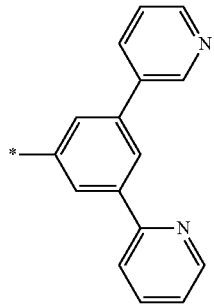
5-33
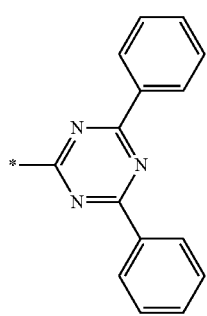
166
-continued
5-34
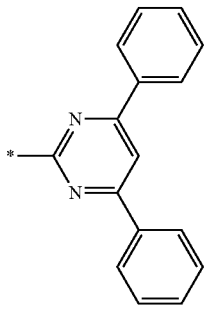
5-35
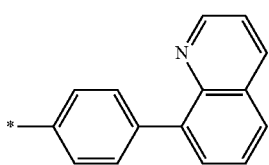
5-36
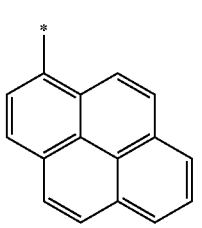
5-37
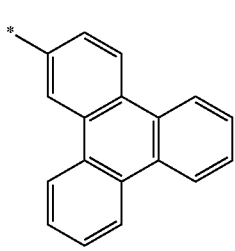
5-38
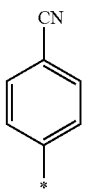
5-39
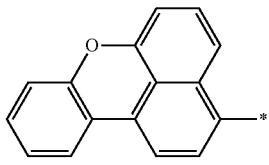
5-40
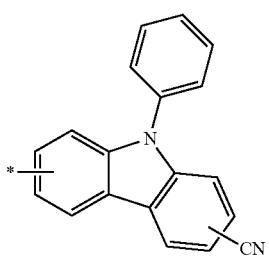

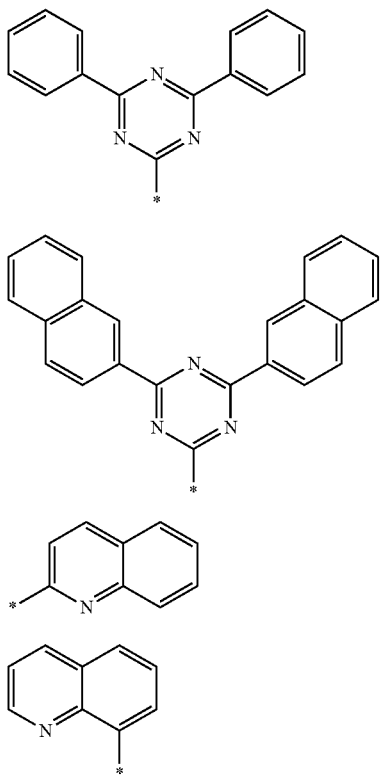

in Formulae 5-1 to 5-44, * is a binding site to a neighboring atom.

13. The condensed cyclic compound as claimed in claim 1, wherein the condensed cyclic compound represented by Formula 1 is represented by any one of Formulae 1A to 1D:

<Formula 1A>

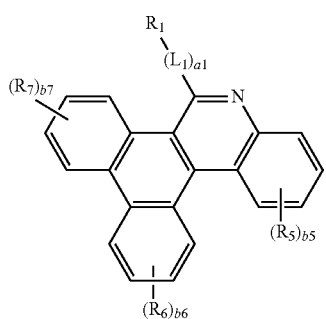

<Formula 1B>

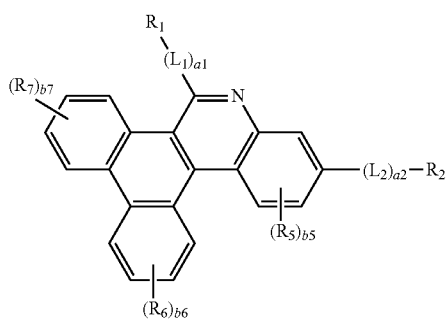

<Formula 1C>

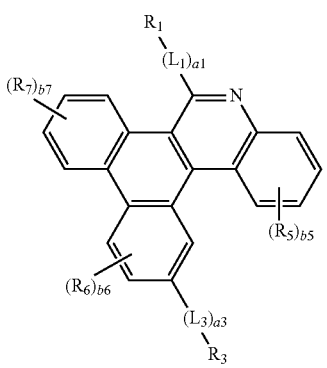

<Formula 1D>

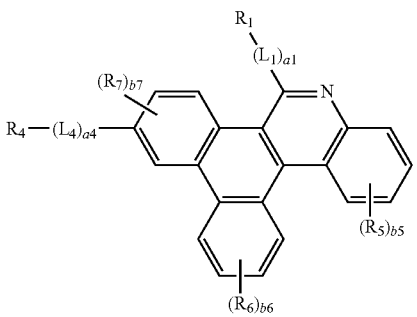

in Formulae 1A to 1D, $L_1$ to $L_4$, a1 to a4, $R_1$ to $R_7$, and b5 to b7 are the same as defined with respect to Formula 1, provided that i) when *-$(L_1)a_1$-$R_1$ in Formula 1A to 1D is a phenyl group, $R_2$ and $R_5$ are not a methyl group, ii) when *-$(L_1)a_1$-$R_1$ in Formula 1A to 1D is not a phenyl group, at least one of $R_1$ and is to $R_7$ in Formula 1A, at least one of $R_1$, $R_2$, and $R_5$ to $R_7$ in Formula 1B, at least one of $R_1$, $R_3$, and $R_5$ to $R_7$ in Formula 1C and at least one of $R_1$ and $R_4$ to $R_6$ in Formula 1D are not hydrogen, iii) when *-$(L_1)_{a1}$-$R_1$ in Formulae 1A to 1 D is —P(=O)($Q_1$)($Q_2$), and $Q_1$ and $Q_2$ are phenyl groups, $R_5$ is not a methyl group, and iv) when *-$(L_1)_{a1}$-$R_1$ in Formula 1 is a phenyl group, at least one of $R_2$, $R_3$, and $R_4$ is not hydrogen.

14. The condensed cyclic compound as claimed in claim 1, wherein the condensed cyclic compound represented by Formula 1 is represented by any one of Formulae 1E to 1H:

<Formula 1E>

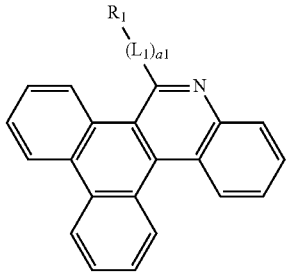

<Formula 1F>

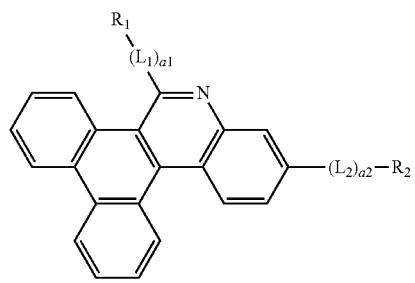

<Formula 1G>

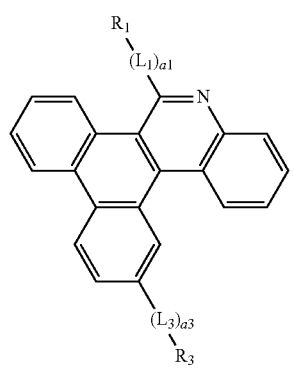

<Formula 1H>

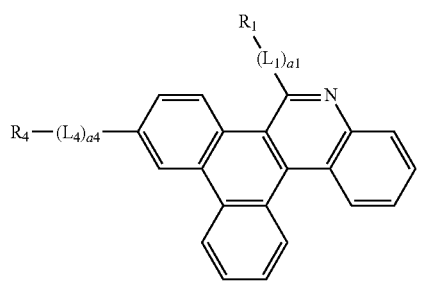

in Formulae 1E to 1H, $L_1$ to $L_4$, a1 to a4, and $R_1$ to $R_4$ are the same as defined with respect to Formula 1, provided that i) when *-$(L_1)a_1$-$R_1$ in Formula 1F is a phenyl group, $R_2$ is not a methyl group, ii) when *-$(L_1)a_1$-$R_1$ in Formula 1E to 1H is not a phenyl group, $R_1$ in Formula 1E, at least one of $R_1$ and $R_2$ in Formula 1F, at least one of $R_1$ and $R_3$ in Formula 1 G and at least one of $R_1$ and $R_4$ in Formula 1H are not hydrogen, iii) when *-$(L_1)_{a1}$-$R_1$ in Formulae 1E to 1H is —P(=O)($Q_1$)($Q_2$), and $Q_1$ and $Q_2$ are phenyl groups, $R_5$ is not a methyl group, and iv) when *-$(L_1)_{a1}$-$R_1$ in Formula 1 is a phenyl group, at least one of $R_2$, $R_3$, and $R_4$ is not hydrogen.

15. The condensed cyclic compound as claimed in claim 14, wherein:

a1 is selected from 0, 1, and 2, and $L_1$ to $L_4$ are each independently selected from a group represented by any one of Formulae 4-1 to 4-21:

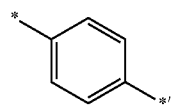
4-1

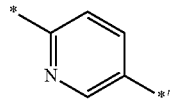
4-2

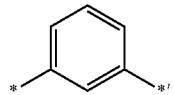
4-3

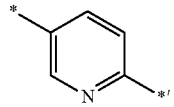
4-4

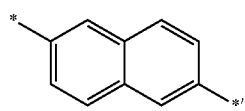
4-5

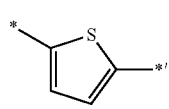
4-6

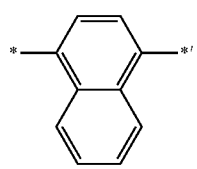
4-7

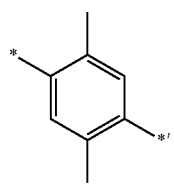
4-8

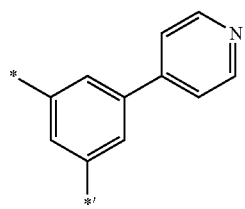
4-9

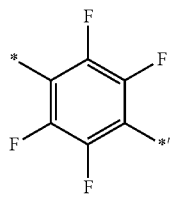
4-10

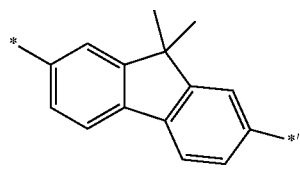
4-11

-continued
4-12 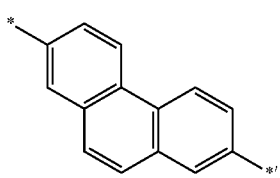
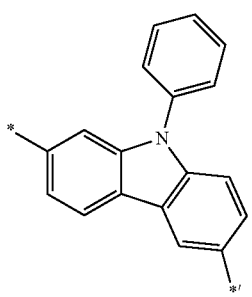
4-13
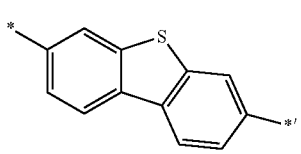
4-14
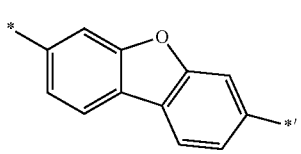
4-15
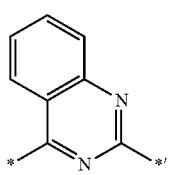
4-16
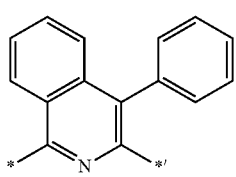
4-17
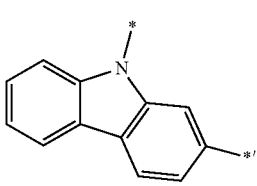
4-18
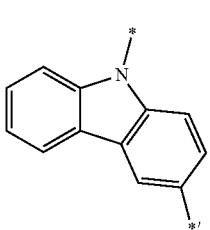
4-19
-continued
4-20 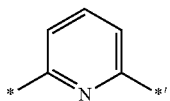
4-21 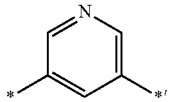
in Formulae 4-1 to 4-21, * and *' are binding sites to neighboring atoms.
16. The condensed cyclic compound as claimed in claim 14, wherein R₁ to R₄ are each independently selected from hydrogen and a group represented by any one of Formulae 5-1 to 5-44, provided that at least one of R₁ to R₄ is not hydrogen:
5-1 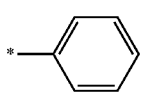
5-2 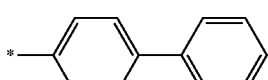
5-3 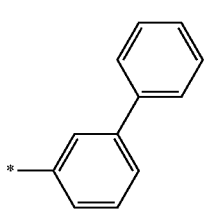
5-4 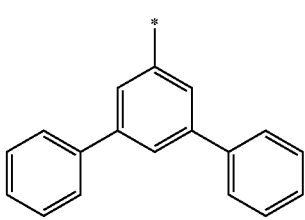
5-5 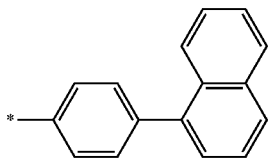
5-6 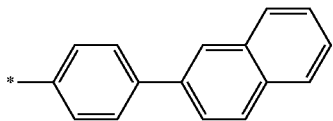
5-7 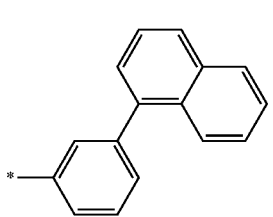

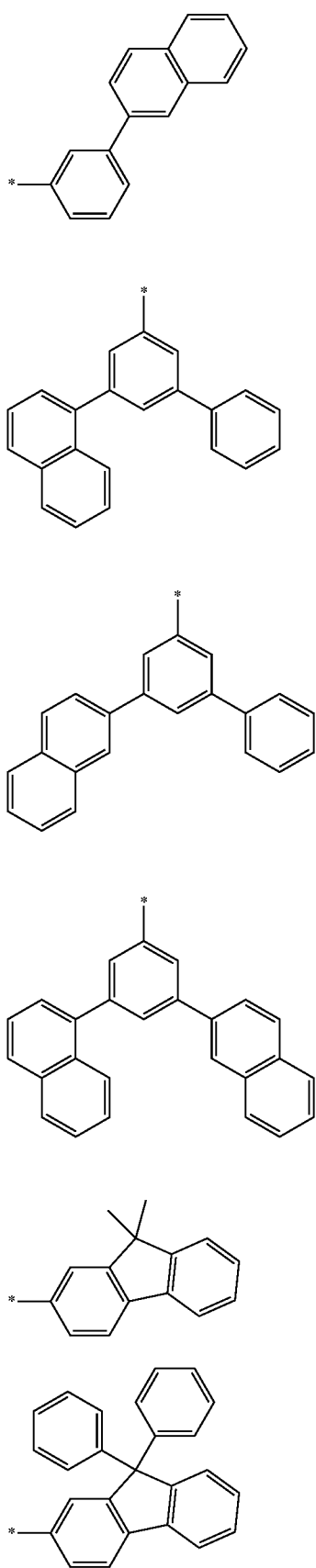
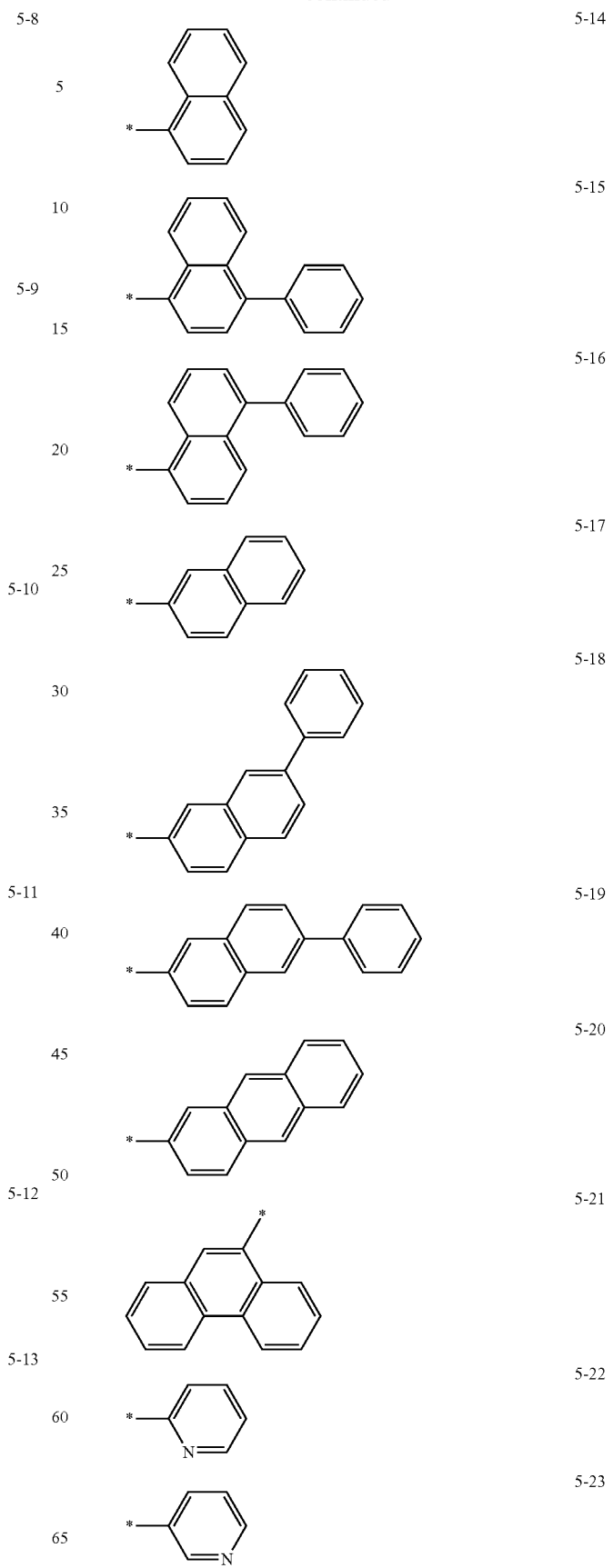

-continued
5-24 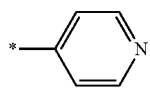
5-25 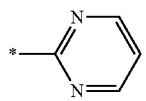
5-26 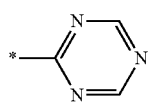
5-27 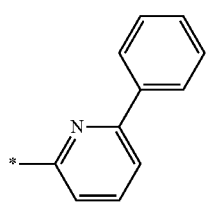
5-28 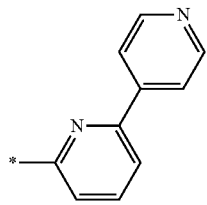
5-29 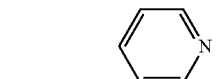
5-30 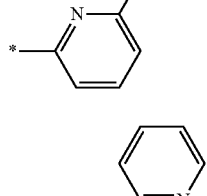
5-31 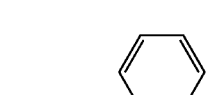
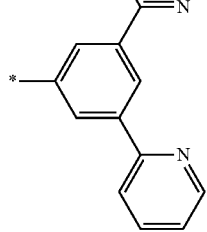
-continued
5-32 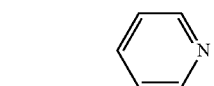
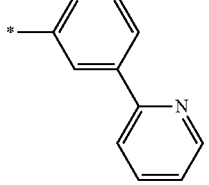
5-33 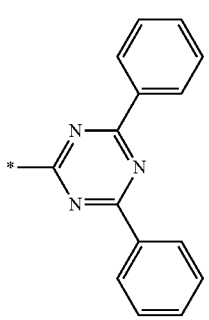
5-34 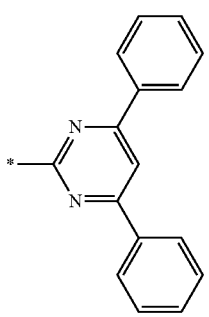
5-35 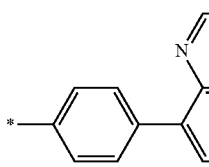
5-36 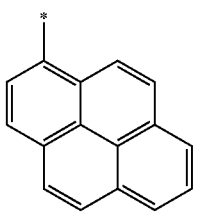
5-37 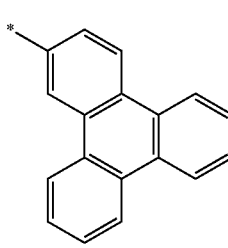

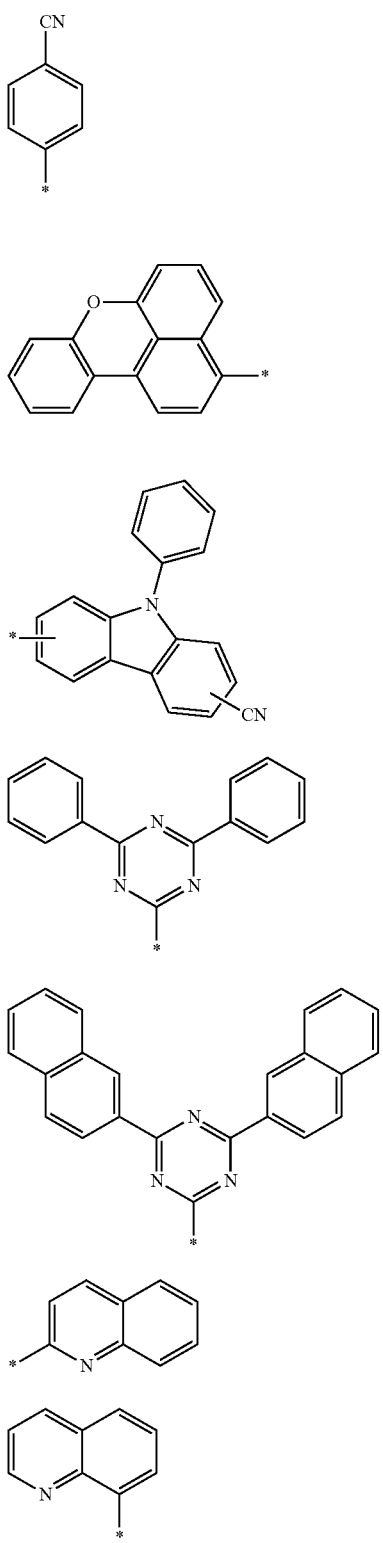
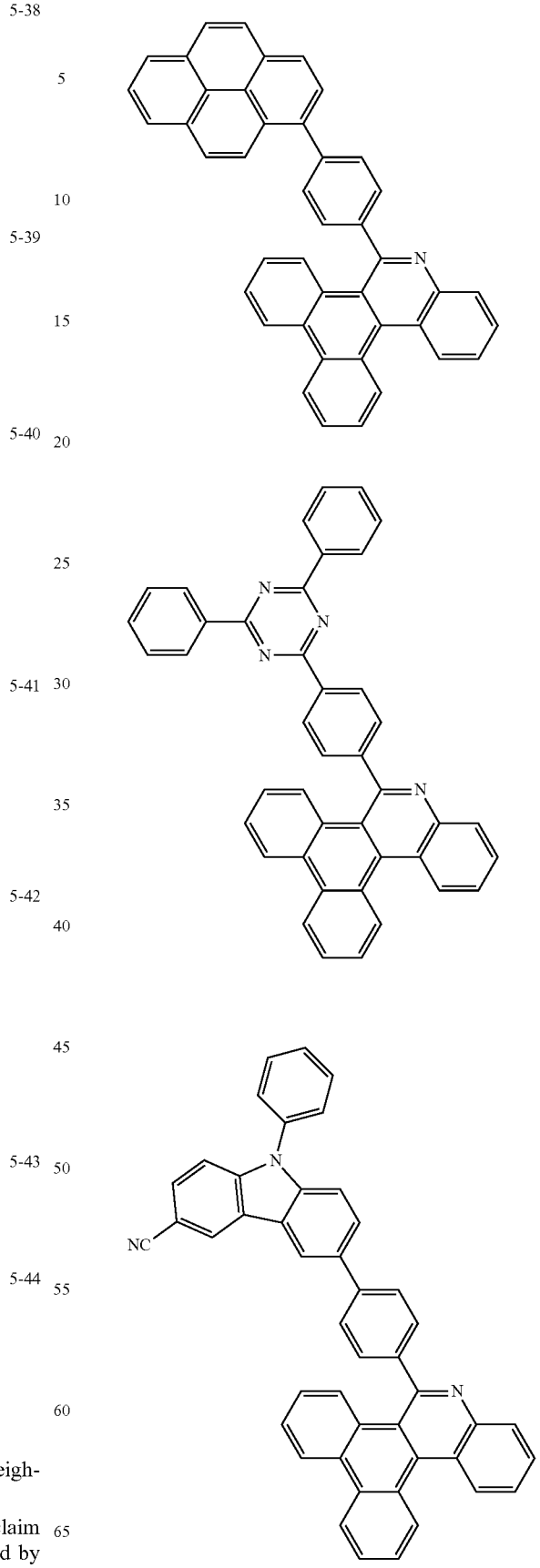
in Formulae 5-1 to 5-44, * is a binding site to a neighboring atom.
17. The condensed cyclic compound as claimed in claim 1, wherein the condensed cyclic compound represented by Formula 1 is selected from Compounds 1 to 82:

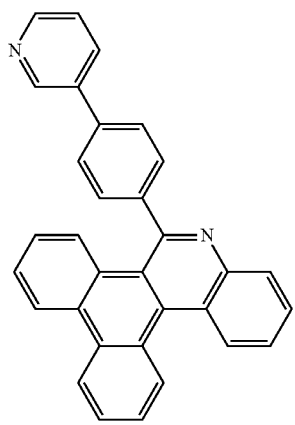
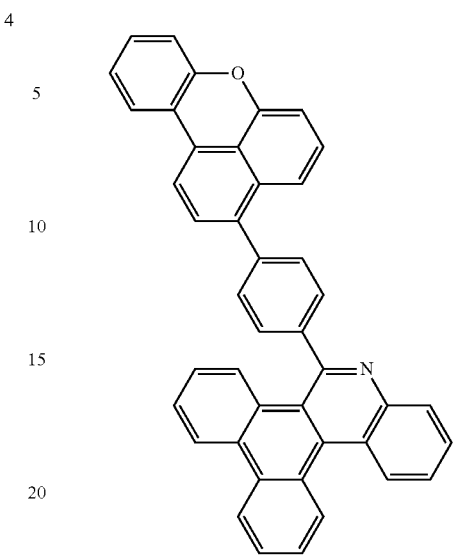
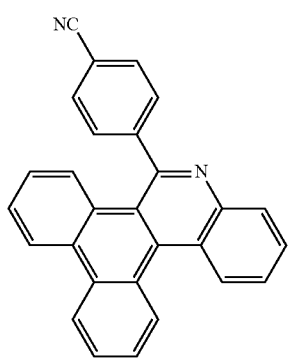
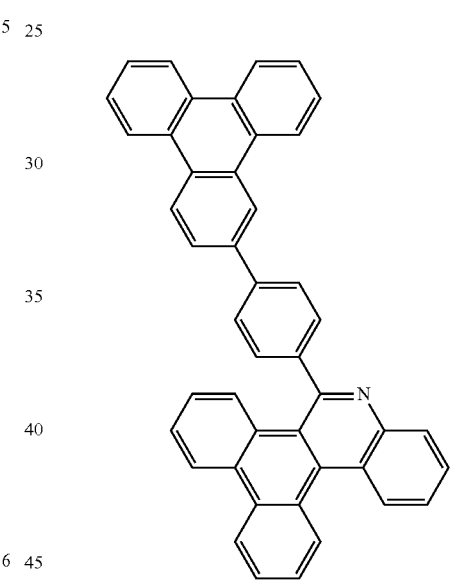
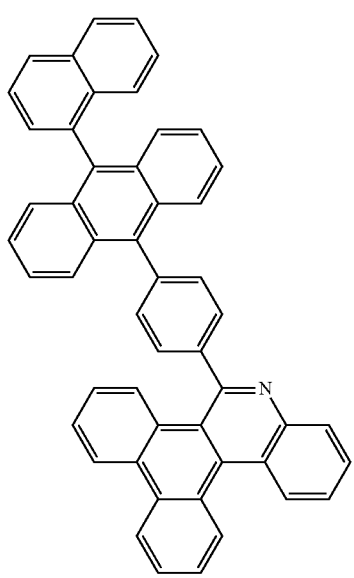
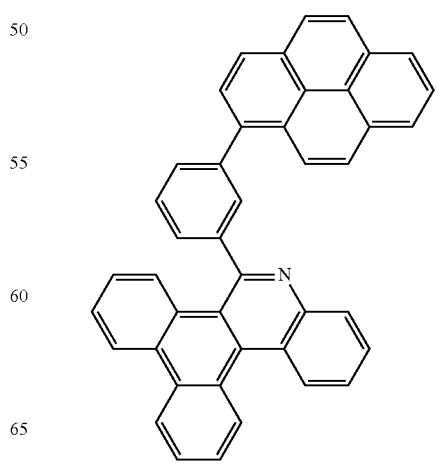

181
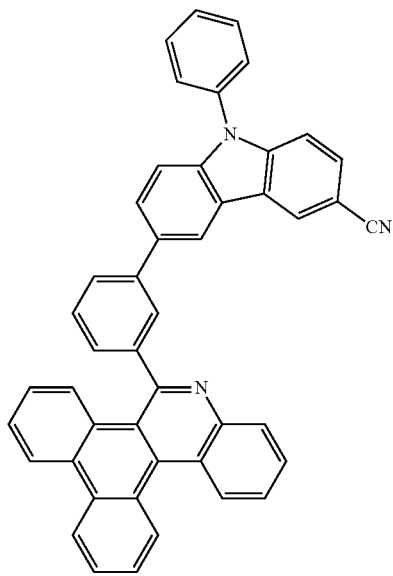
10
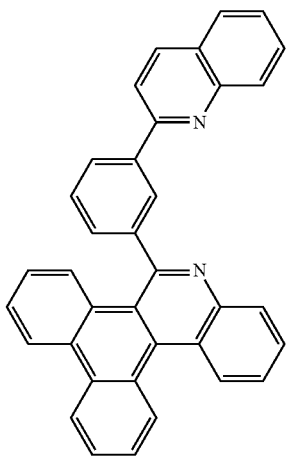
11
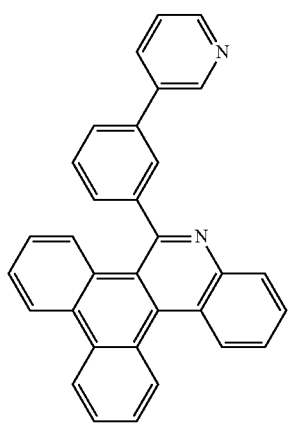
12
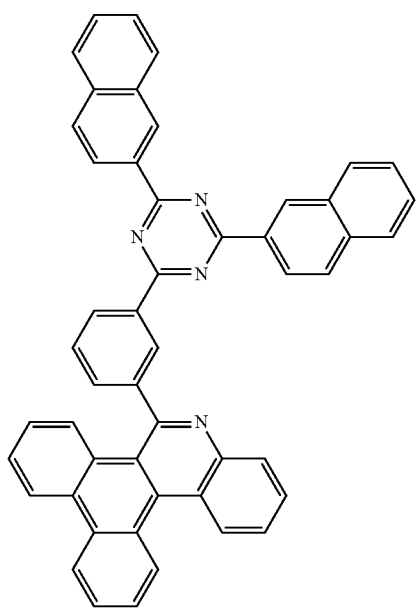
182
13
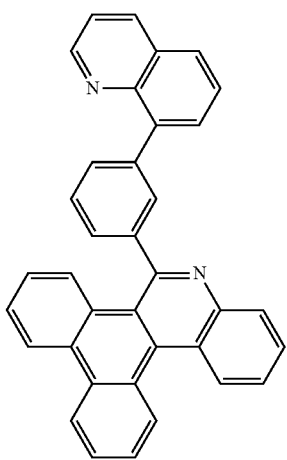
14
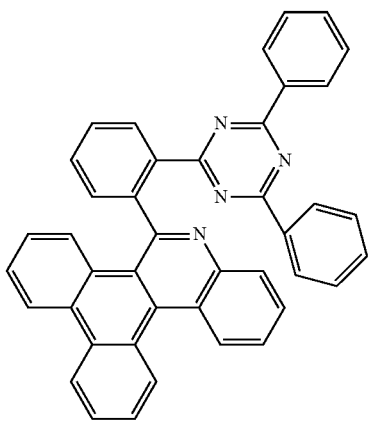
15

16
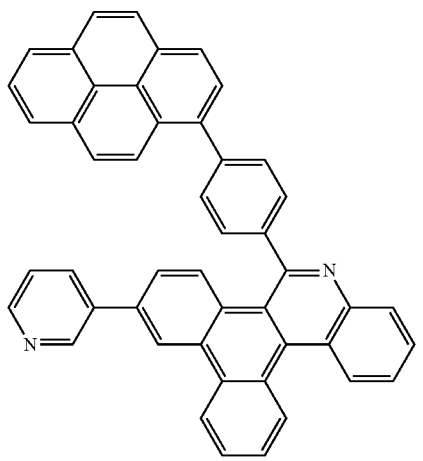
17
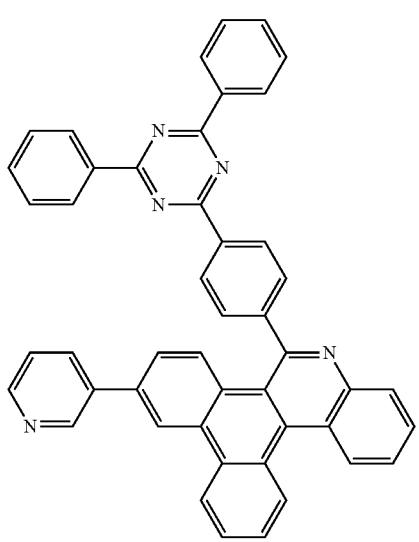
18
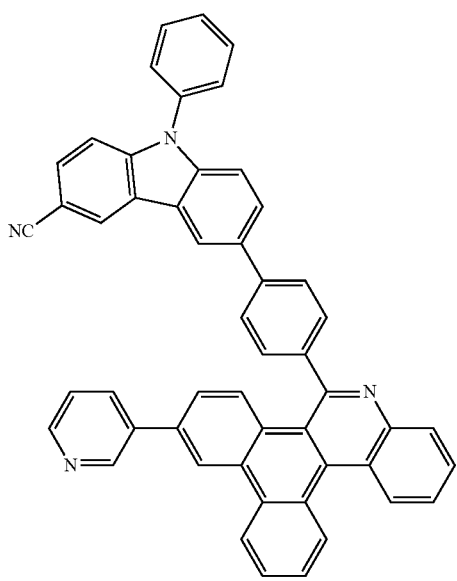
19
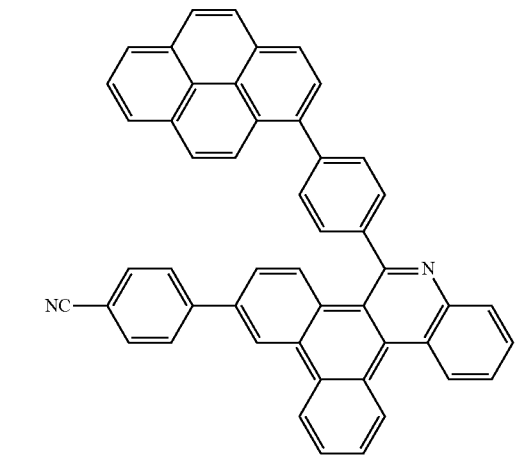
20
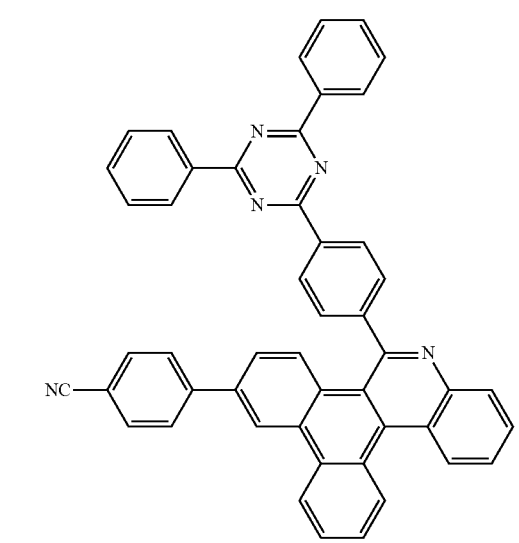
21
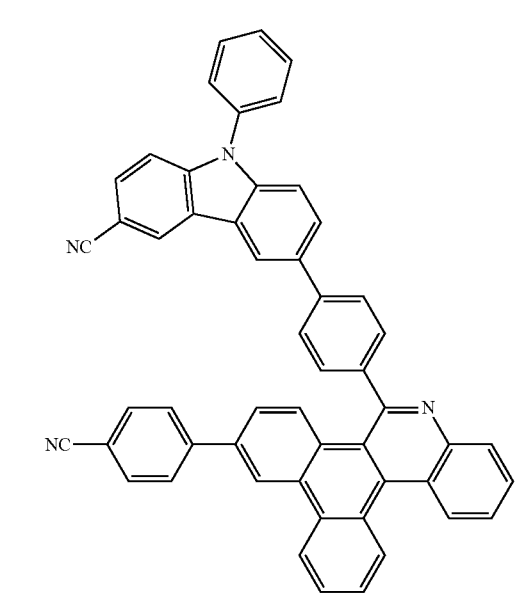

22
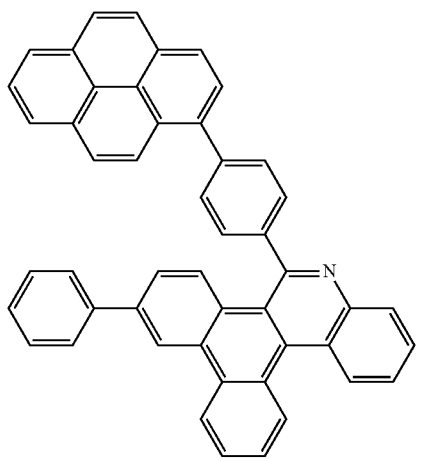
23
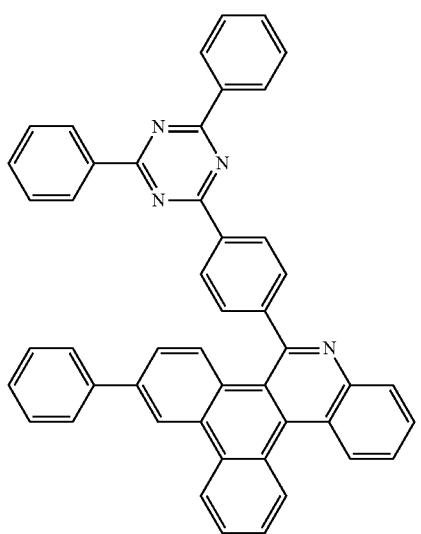
24
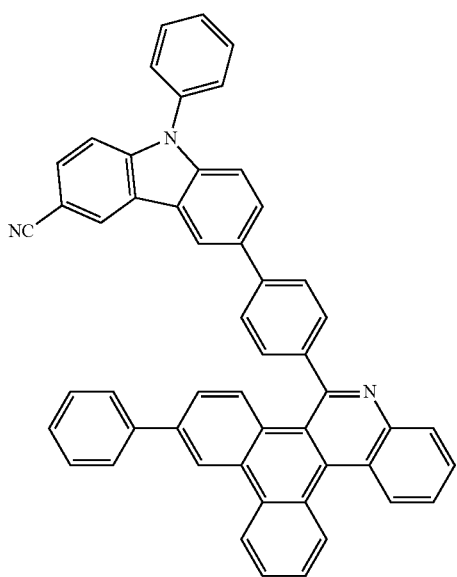
25
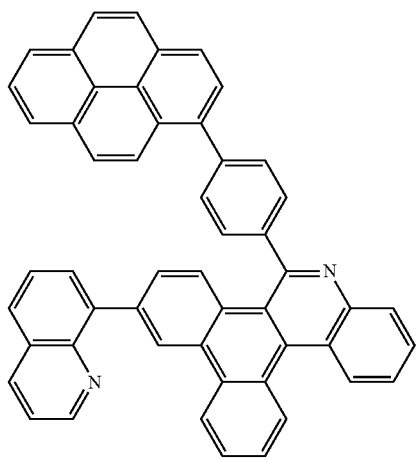
26
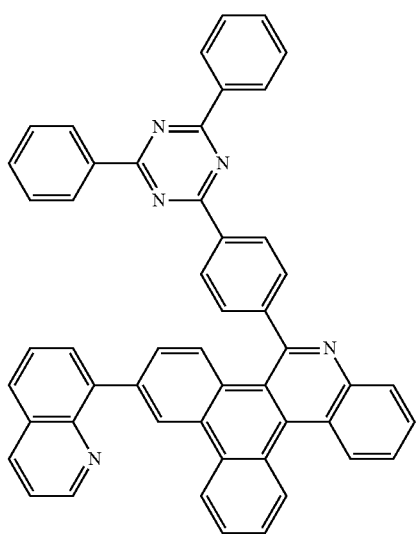
27
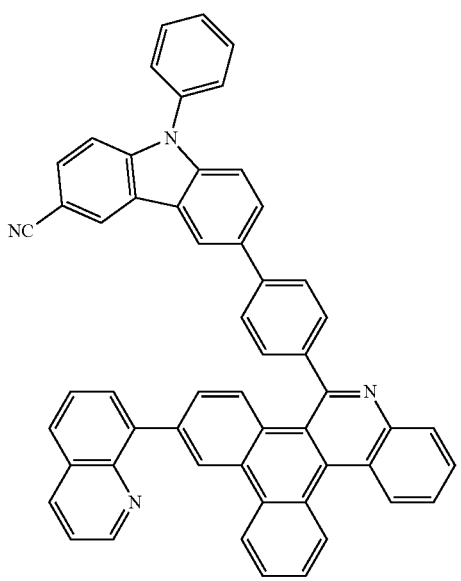

28
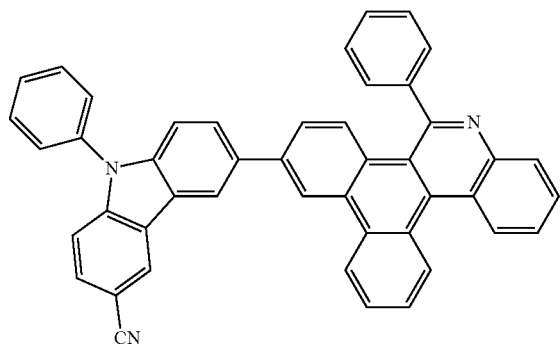
29
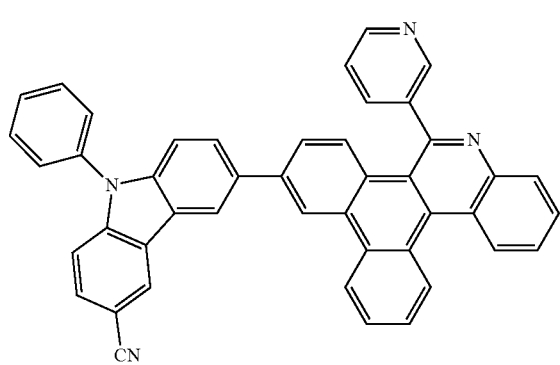
30
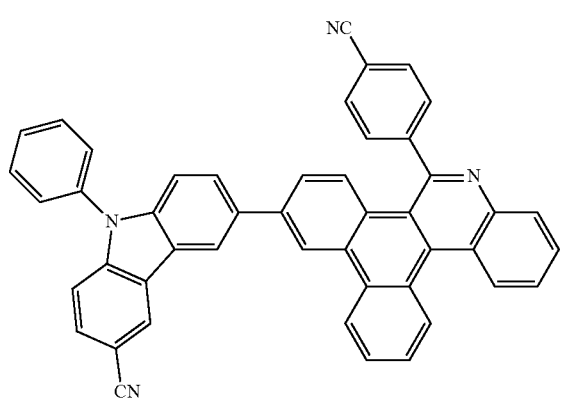
31
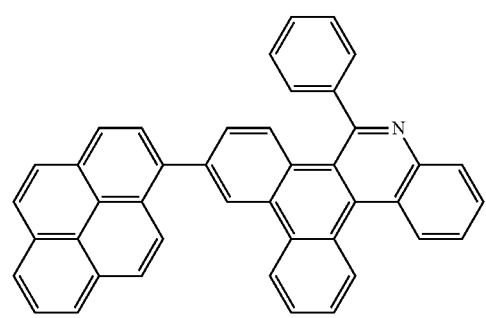
32
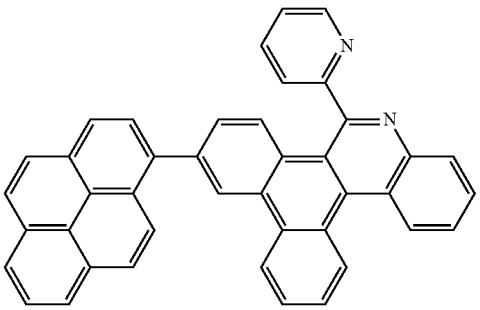
33
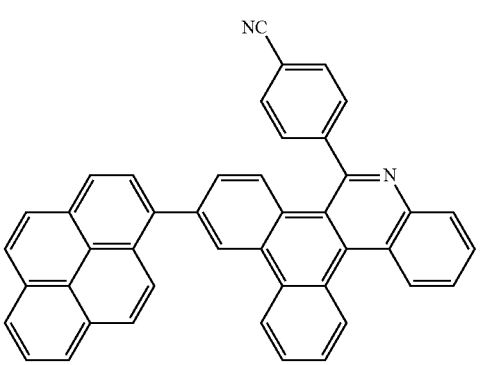
34
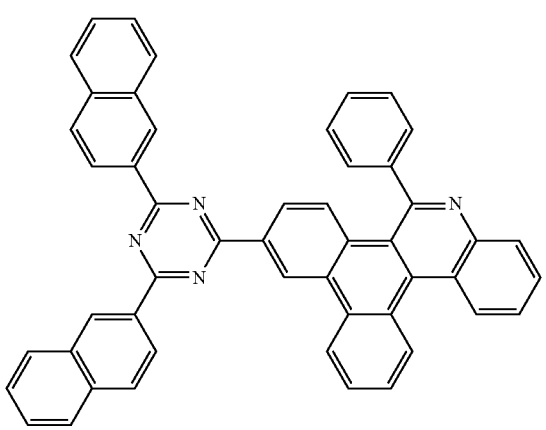
35
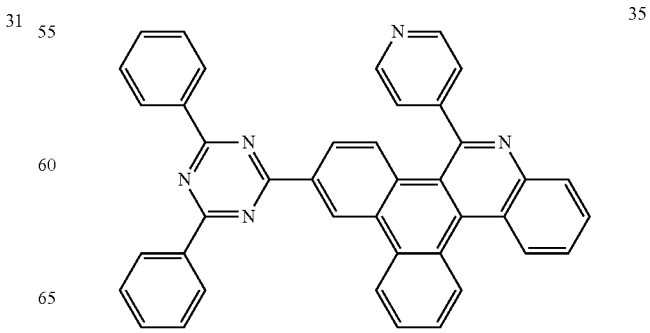

36
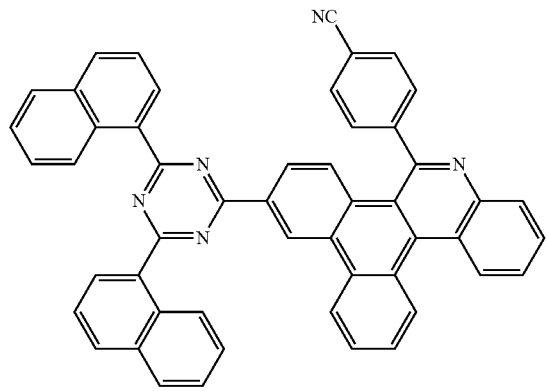
37
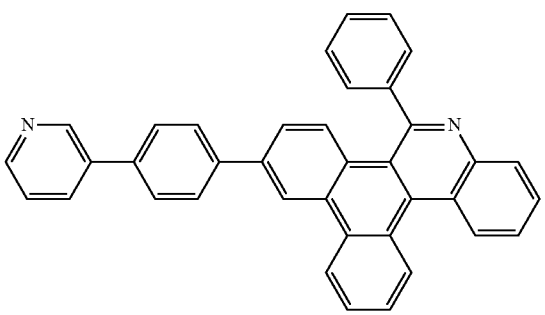
38
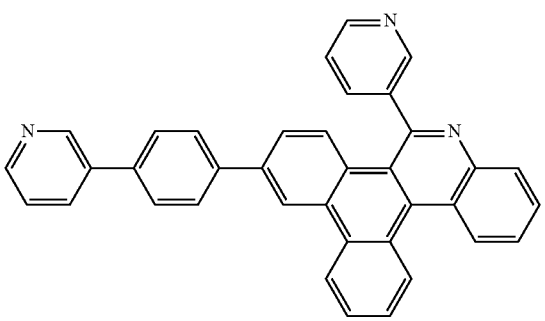
39
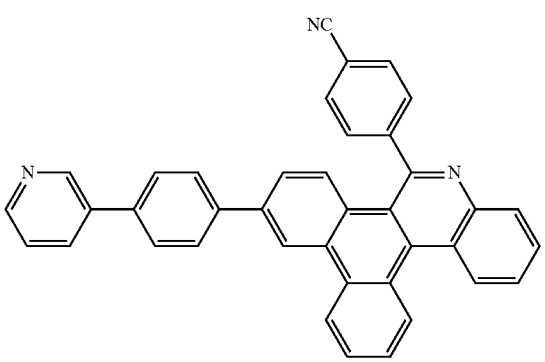
40
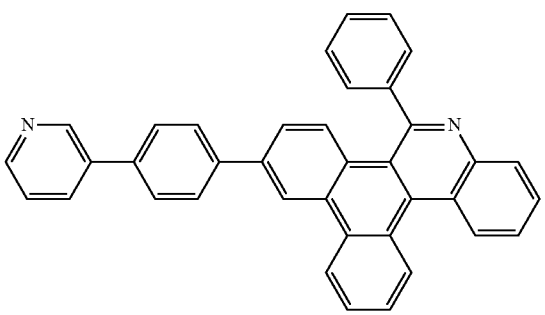
41
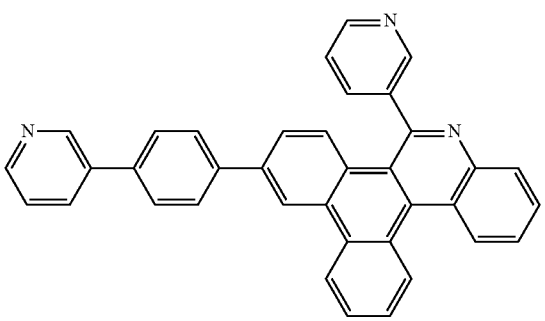
42
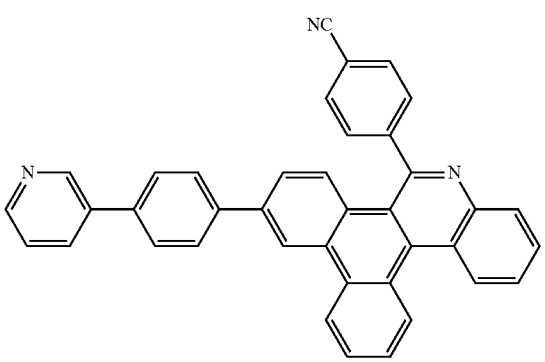
43
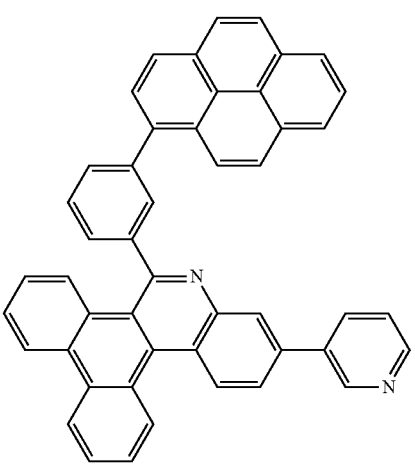

191
-continued
44
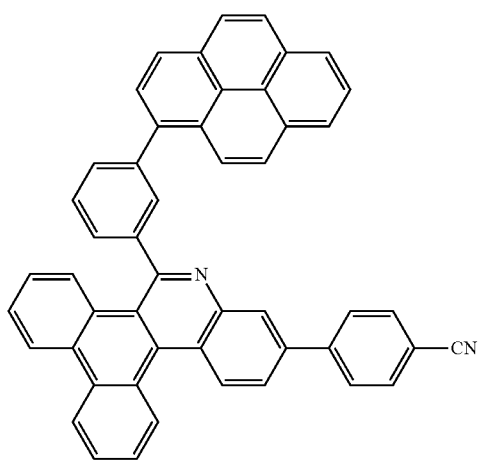
45
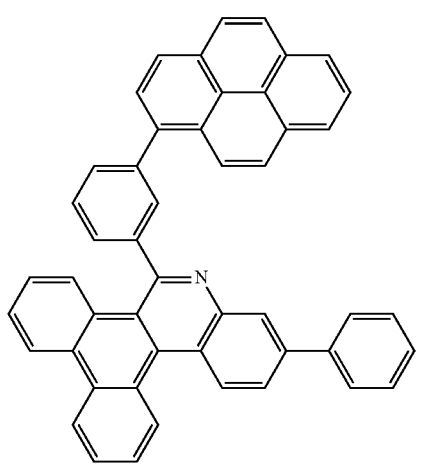
46
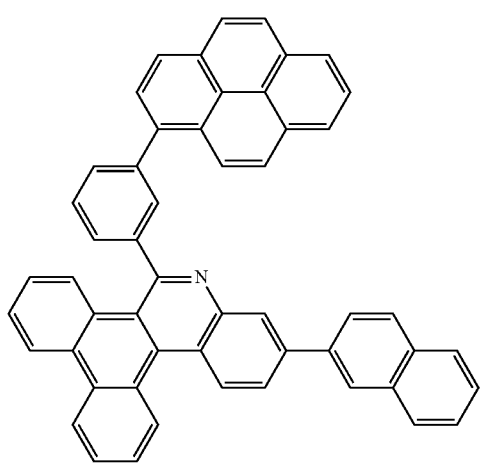
192
-continued
47
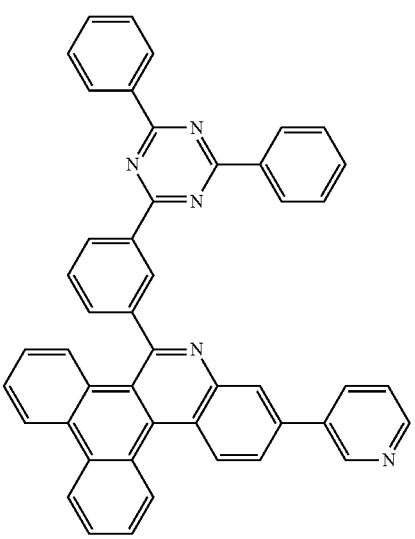
48
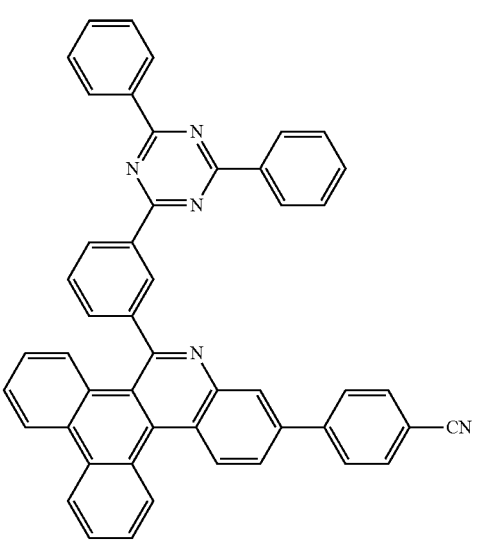
49
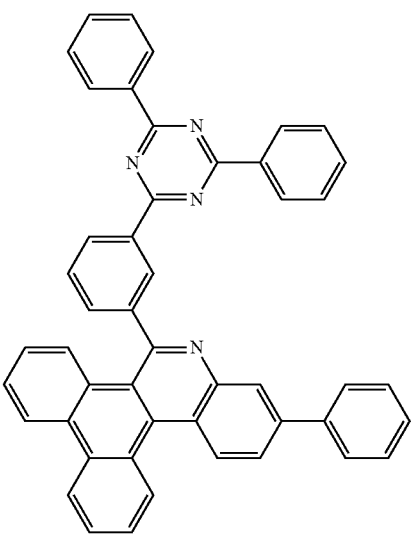

50
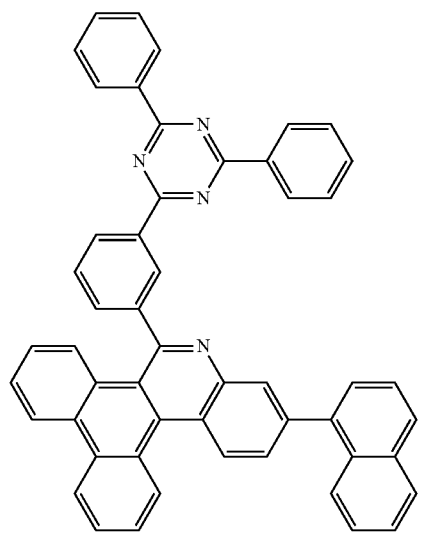
51
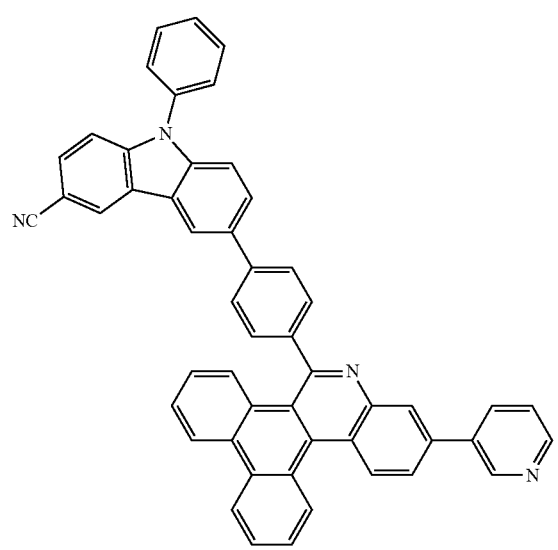
52
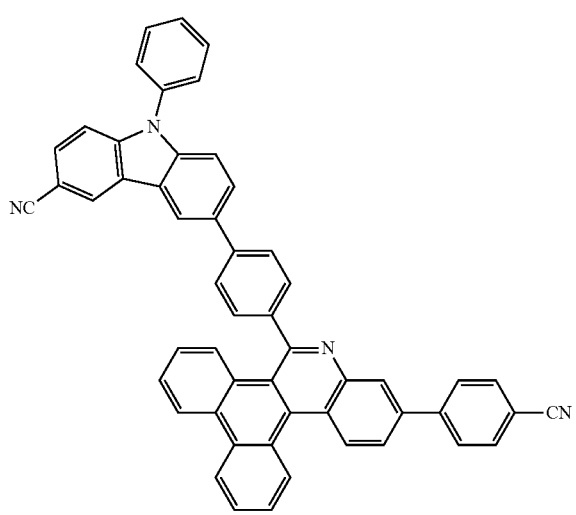
53
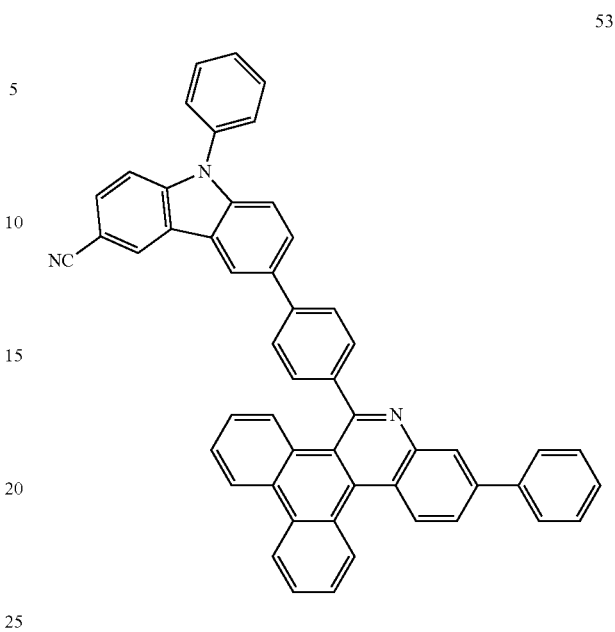
54
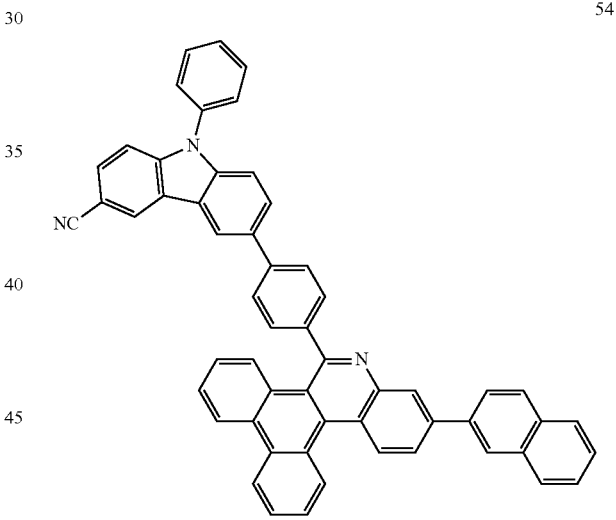
55
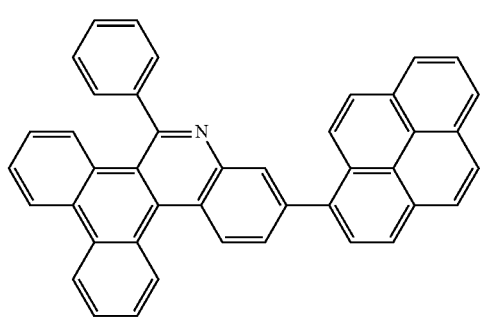

-continued
56
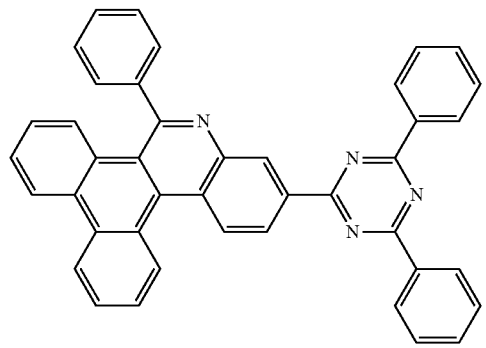
57
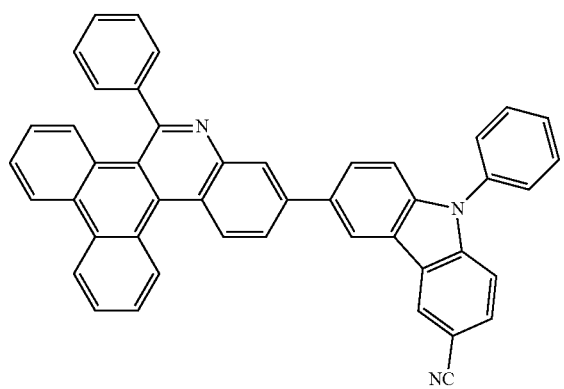
58
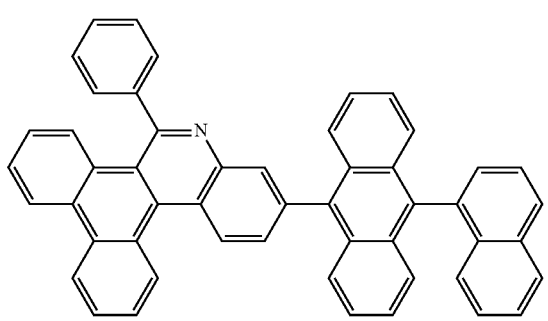
59
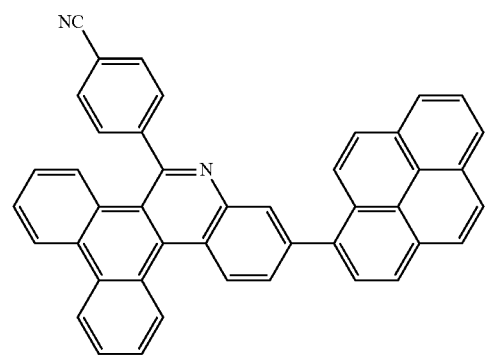
-continued
60
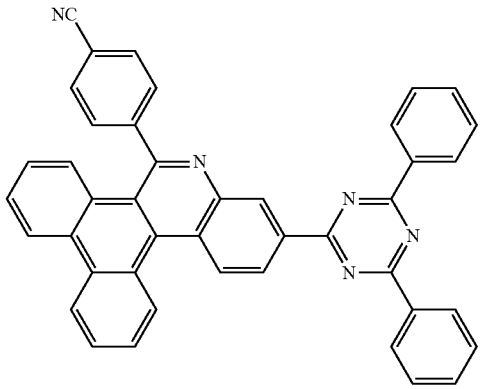
61
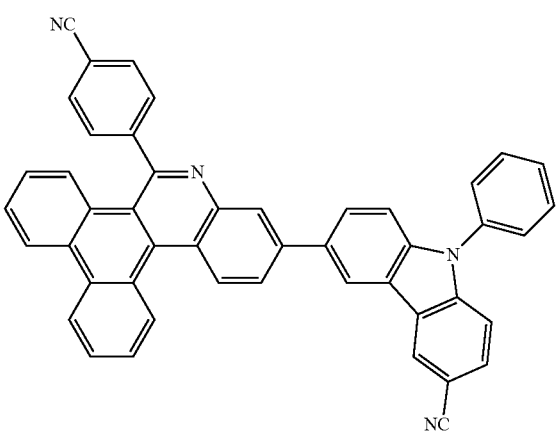
62
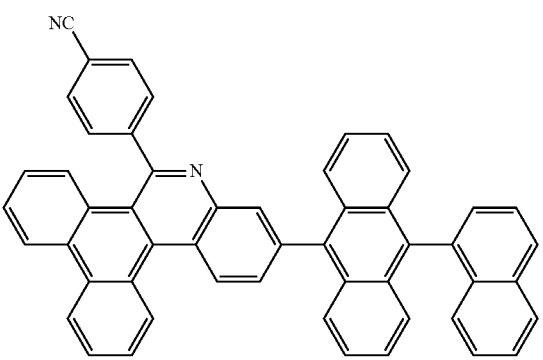
63
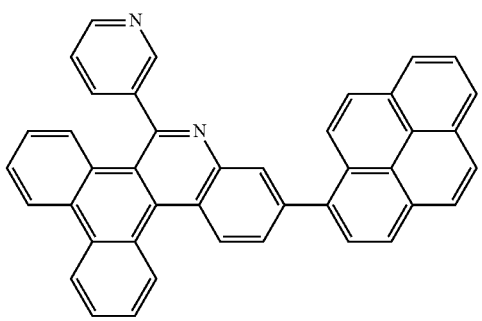

197
-continued
64
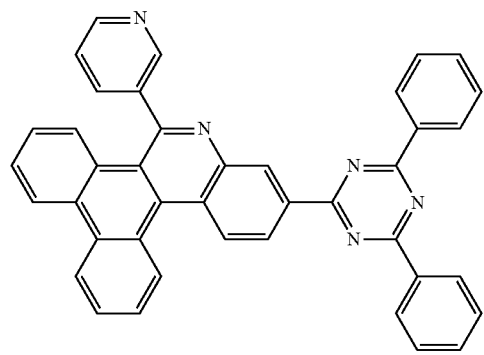
65
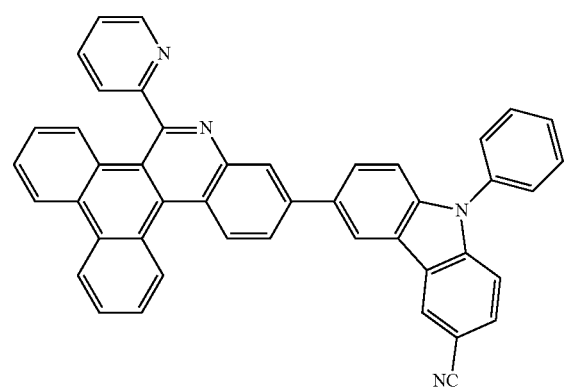
66
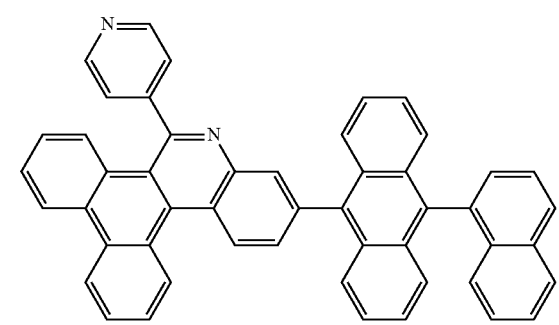
67
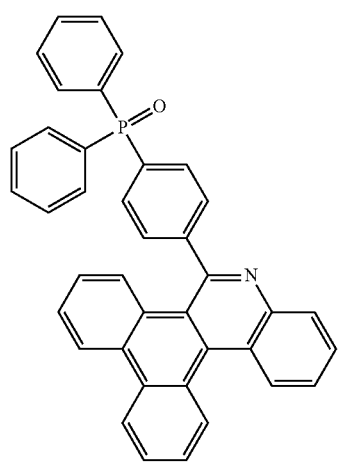
198
-continued
68
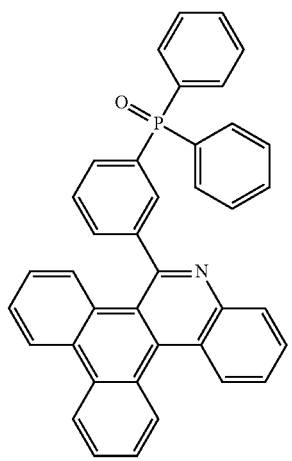
69
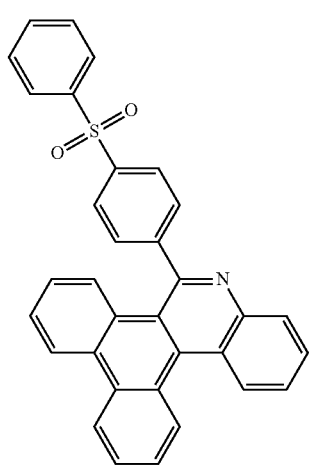
70
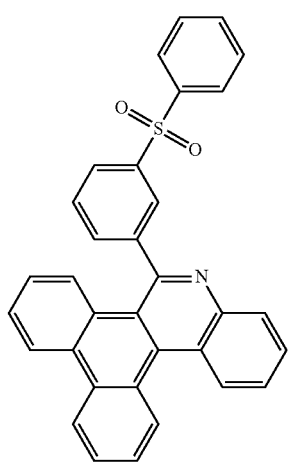

-continued
71
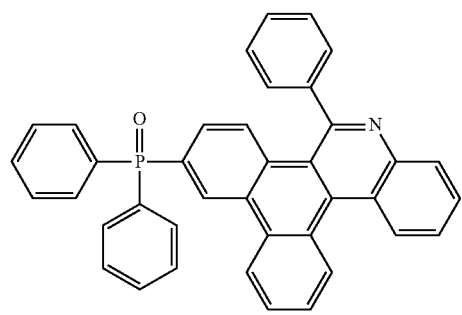
72
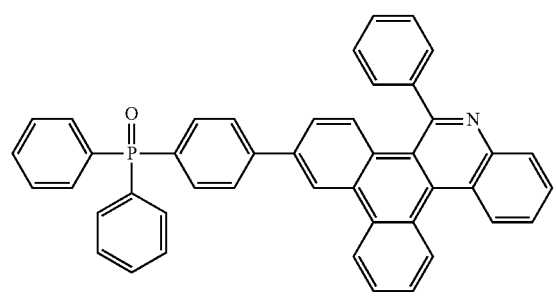
73
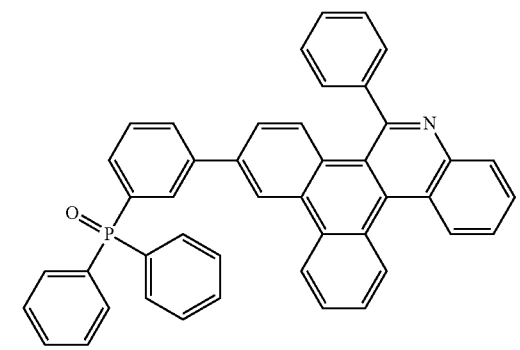
74
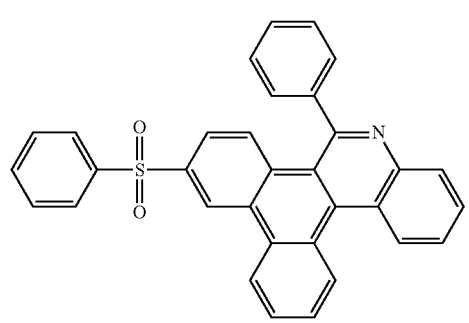
75
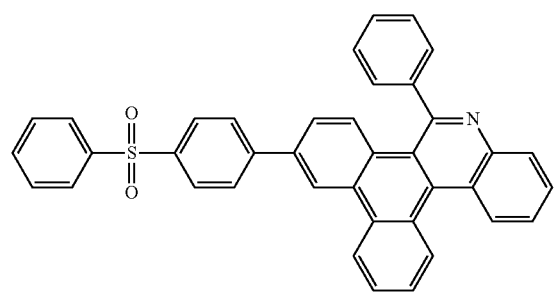
-continued
76
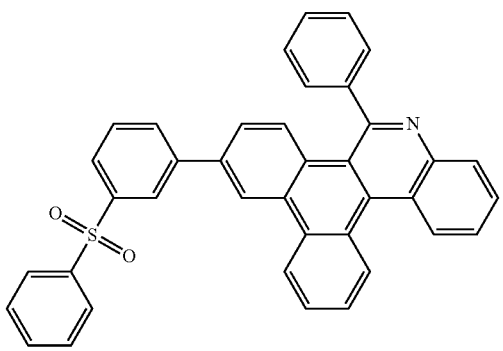
77
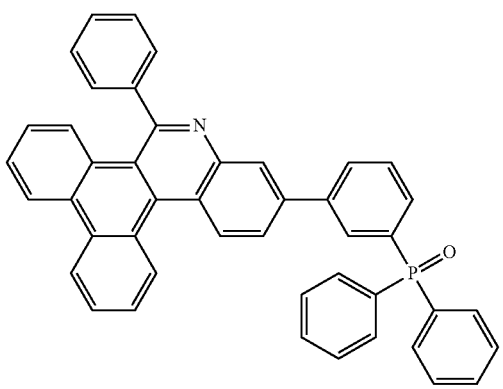
78
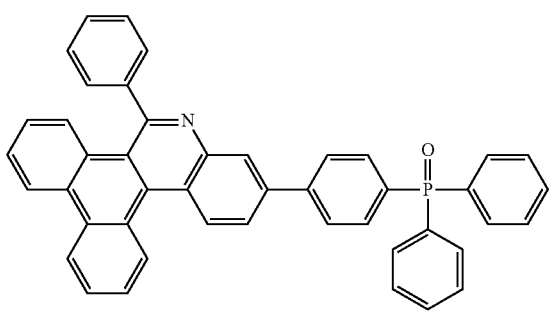
79
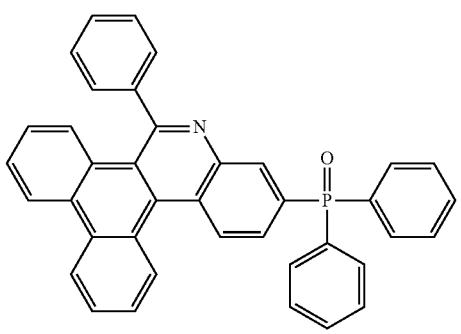

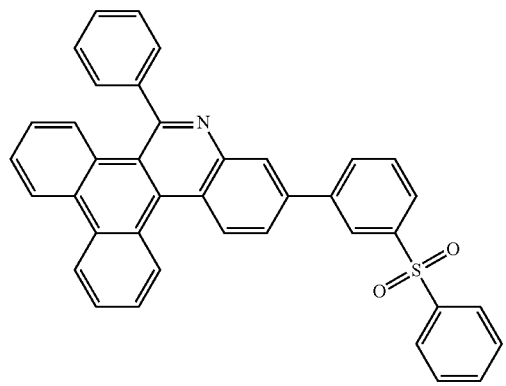

80

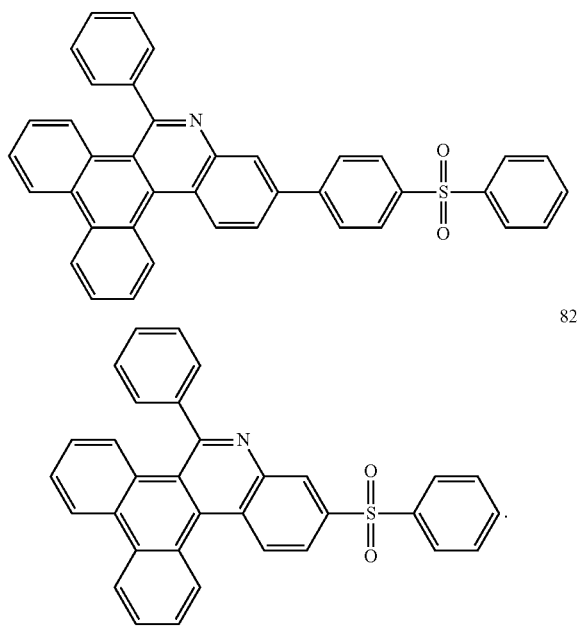

81

82

18. An organic light-emitting device, comprising:
a first electrode;
a second electrode; and
an organic layer between the first electrode and the second electrode, the organic layer including an emission layer,
wherein the organic layer includes the condensed cyclic compound as claimed in claim 1.

19. The organic light-emitting device as claimed in claim 18, wherein the organic layer further includes an electron transport region between the emission layer and the second electrode, the electron transport region including the condensed cyclic compound.

20. The organic light-emitting device as claimed in claim 19, wherein the electron transport region includes an electron transport layer, the electron transport layer including the condensed cyclic compound.

21. The condensed cyclic compound as claimed in claim 1, wherein:
at least one of $R_1$ to $R_4$ are each independently selected from a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{10}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed hetero-polycyclic group, —P(=O)(Q$_1$)(Q$_2$), and —S(=O)$_2$(Q$_1$); or
at least one of $R_5$ to $R_7$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_1$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed hetero-polycyclic group.

22. The condensed cyclic compound as claimed in claim 1, wherein:
a1 is selected from 1, 2, and 3; or
$R_1$ is selected from a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —P(=O)(Q$_1$)(Q$_2$), and —S(=O)$_2$(Q$_1$).

* * * * *